United States Patent
Wallach et al.

(10) Patent No.: US 7,429,648 B1
(45) Date of Patent: Sep. 30, 2008

(54) IREN PROTEIN, ITS PREPARATION AND USE

(75) Inventors: David Wallach, Rehovot (IL); Nikolay Malinin, Brookline, MA (US); Indranil Sinha, Rehovot (IL); Stefan Leu, Maslul (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 489 days.

(21) Appl. No.: 10/070,255

(22) PCT Filed: Aug. 31, 2000

(86) PCT No.: PCT/IL00/00517

§ 371 (c)(1),
(2), (4) Date: Aug. 20, 2002

(87) PCT Pub. No.: WO01/16314

PCT Pub. Date: Mar. 8, 2001

(30) Foreign Application Priority Data

Sep. 2, 1999 (IL) .................................... 131719

(51) Int. Cl.
*C07H 21/04* (2006.01)
*C12N 15/63* (2006.01)

(52) U.S. Cl. .................. 536/23.1; 536/23.5; 435/320.1; 435/325

(58) Field of Classification Search ................. 536/23.1
See application file for complete search history.

(56) References Cited

FOREIGN PATENT DOCUMENTS

WO          WO 97/37016         * 10/1997

* cited by examiner

*Primary Examiner*—Sean McGarry
*Assistant Examiner*—Kimberly Chong
(74) *Attorney, Agent, or Firm*—Browdy and Neimark, P.L.L.C.

(57) ABSTRACT

There are provided DNA sequences encoding TRAF binding proteins, proteins encoded thereby, and their use in the treatment or prevention of pathological conditions associated with NF-κB induction, or an activity mediated by a TRAF.

5 Claims, 25 Drawing Sheets

```
GGTACCGAGCTCGGATCCACTAGTAACGGCCGCCAGTGTGCTGGAATTCTG
CGGATGTACCCATACGATGTTCCAGATACGCTGAATTTCGAGGCCACGAAG
GCCGGCGGCGCGGCGCAGGCACCGGCCCGGGGAGAGGCACC
```

Figure 3A

```
    ATG AGC GGA TCA CAG AAC AAT GAC AAA AGA CAA TTT CTG CTG GAG CGA CTG CTG GAT GCA
61                                            91
GTG AAA CAG TGC CAG ATC CGC TTT GGA GGG AGA AAG GAG ATT GCC TCG GAT TCC GAC AGC
121                                           151
AGG GTC ACC TGT CTG TGT GCC CAG TTT GAA GCC GTC CTG CAG CAT GGC TTG AAG AGG AGT
181                                           211
CGA GGA TTG GCA CTC ACA GCG GCA GCG ATC AAG CAG GCA GCG GGC TTT GCC AGC AAA ACC
241                                           271
GAA ACA GAG CCC GTG TTC TGG TAC TAC GTG AAG GAG GTC CTC AAC AAG CAC GAG CTG CAG
301                                           331
CGC TTC TAC TCC CTG CGC CAC ATC GCC TCA GAC GTG GGC CGG GGT CGC GCC TGG CTG CGC
361                                           391
TGT GCC CTC AAC GAA CAC TCC CTG GAG CGC TAC CTG CAC ATG CTC CTG GCC GAC CGC TGC
421                                           451
AGG CTG AGC ACT TTT TAT GAA GAC TGG TCT TTT GTG ATG GAT GAA GAA AGG TCC AGT ATG
481                                           511
CTT CCT ACC ATG GCA GCA GGT CTG AAC TCC ATA CTC TTT GCG ATT AAC ATC GAC AAC AAG
541                                           571
GAT TTG AAC GGG CAG AGT AAG TTT GCT CCC ACC GTT TCA GAC CTC TTA AAG GAG TCA ACG
601                                           631
CAG AAC GTG ACC TCC TTG CTG AAG GAG TCC ACG CAA GGA GTG AGC AGC CTG TTC AGG GAG
661                                           691
ATC ACA GCC TCC TCT GCC GTC TCC ATC CTC ATC AAA CCT GAA CAG GAG ACC GAC CCC TTG
721                                           751
CCT GTC GTG TCC AGG AAT GTC AGT GCT GAT GCC AAA TGC AAA AAG GAG CGG AAG AAG AAA
781                                           811
AAG AAA GTG ACC AAC ATA ATC TCA TTT GAT GAT GAG GAA GAT GAG CAG AAC TCT GGG GAC
841                                           871
GTG TTT AAA AAG ACA CCT GGG GCA GGG GAG AGC TCA GAG GAC AAC TCC GAC CGC TCC TCT
901                                           931
GTC AAT ATC ATG TCC GCC TTT GAA AGC CCC TTC GGG CCT AAC TCC AAT GGA AGT CAG AGC
961                                           991
AGC AAC TCA TGG AAA ATT GAT TCC CTG TCT TTG AAC GGG GAG TTT GGG TAC CAG AAG CTT
1021                                          1051
GAT GTG AAA AGC ATC GAT GAT GAA GAT GTG GAT GAA AAC GAA GAT GAC GTG TAT GGA AAC
1081                                          1111
TCA TCA GGA AGG AAG CAC AGG GGC CAC TCG GAG TCG CCC GAG AAG CCA CTG GAA GGG AAC
1141                                          1171
ACC TGC CTC TCC CAG ATG CAC AGC TGG GCT CCG CTG AAG GTG CTG CAC AAT GAC TCC GAC
1201                                          1231
ATC CTC TTC CCT GTC AGT GGC GTG GGC TCC TAC AGC CCA GCA GAT GCC CCC CTC GGA AGC
1261                                          1291
CTG GAG AAC GGG ACA GGA CCA GAG GAC CAC GTT CTC CCG GAT CCT GGA CTT CGG TAC AGT
1321                                          1351
GTG GAA GCC AGC TCT CCA GGC CAC GGA AGT CCT CTG AGC AGC CTG TTA CCT TCT GCC TCA
1381                                          1411
GTG CCA GAG TCC ATG ACA ATT AGT GAA CTG CGC CAG GCC ACT GTG GCC ATG ATG AAC AGG
1441                                          1471
AAG GAT GAG CTG GAG GAG GAG AAC AGA TCA CTG CGA AAC CTG CTC GAC GGT GAG ATG GAG
1501/501                                      1531
CAC TCA GCC GCG CTC CGG CAA GAG GTG GAC ACC TTG AAA AGG AAG GTG GCT GAA CAG GAG
1561                                          1591
GAG CGG CAG GGC ATG AAG GTC CAG GCG CTG GCC AGC TAT CTT TGC TAT TTT GTG AGG AGA
1621                                          1651
TTC TAA CCC CAC GTG AGA ACC ATG TGG TGG AGA AAT GGA GGG AGA GAG AAA TCC AAC AGT
1681                                          1711
TCC TGA TAG TCT CAT TTG AGC TCC TGG ATC CAG TCT TTC CTG AAG CTG TGT TTC CTC TGG
1741                                          1771
ACT TTT CAT GTA TGT GAG CCA ATA AAT GCT TTT CAT TCC TTG
```

Figure 3B

```
    ATG AGC GGA TCA CAG AAC AAT GAC AAA AGA CAA TTT CTG CTG GAG CGA CTG CTG GAT GCA
61                                          91
    GTG AAA CAG TGC CAG ATC CGC TTT GGA GGG AGA AAG GAG ATT GCC TCG GAT TCC GAC AGC
121                                         151
    AGG GTC ACC TGT CTG TGT GCC CAG TTT GAA GCC GTC CTG CAG CAT GGC TTG AAG AGG AGT
181                                         211
    CGA GGA TTG GCA CTC ACA GCG GCA GCG ATC AAG CAG GCA GCG GGC TTT GCC AGC AAA ACC
241                                         271
    GAA ACA GAG CCC GTG TTC TGG TAC TAC GTG AAG GAG GTC CTC AAC AAG CAC GAG CTG CAG
301                                         331
    CGC TTC TAC TCC CTG CGC CAC ATC GCC TCA GAC GTG GGC CGG GGT CGC GCC TGG CTG CGC
361                                         391
    TGT GCC CTC AAC GAA CAC TCC CTG GAG CGC TAC CTG CAC ATG CTC CTG GCC GAC CGC TGC
421                                         451
    AGG CTG AGC ACT TTT TAT GAA GAC TGG TCT TTT GTG ATG GAT GAA GAA AGG TCC AGT ATG
481                                         511
    CTT CCT ACC ATG GCA GCA GGT CTG AAC TCC ATA CTC TTT GCG ATT AAC ATC GAC AAC AAG
541                                         571
    GAT TTG AAC GGG CAG AGT AAG TTT GCT CCC ACC GTT TCA GAC CTC TTA AAG GAG TCA ACG
601                                         631
    CAG AAC GTG ACC TCC TTG CTG AAG GAG TCC ACG CAA GGA GTG AGC AGC CTG TTC AGG GAG
661                                         691
    ATC ACA GCC TCC TCT GCC GTC TCC ATC CTC ATC AAA CCT GAA CAG GAG ACC GAC CCC TTG
721                                         751
    CCT GTC GTG TCC AGG AAT GTC AGT GCT GAT GCC AAA TGC AAA AAG GAG CGG AAG AAG AAA
781                                         811
    AAG AAA GTG ACC AAC ATA ATC TCA TTT GAT GAT GAG GAA GAT GAG CAG AAC TCT GGG GAC
841                                         871
    GTG TTT AAA AAG ACA CCT GGG GCA GGG GAG AGC TCA GAG GAC AAC TCC GAC CGC TCC TCT
901                                         931
    GTC AAT ATC ATG TCC GCC TTT GAA AGC CCC TTC GGG CCT AAC TCC AAT GGA AGT CAG AGC
961                                         991
    AGC AAC TCA TGG AAA ATT GAT TCC CTG TCT TTG AAC GGG GAG TTT GGG TAC CAG AAG CTT
1021                                        1051
    GAT GTG AAA AGC ATC GAT GAT GAA GAT GTG GAT GAA AAC GAA GAT GAC GTG TAT GGA AAC
1081                                        1111
    TCA TCA GGA AGG AAG CAC AGG GGC CAC TCG GAG TCG CCC GAG AAG CCA CTG GAA GGG AAC
1141                                        1171
    ACC TGC CTC TCC CAG ATG CAC AGC TGG GCT CCG CTG AAG GTG CTG CAC AAT GAC TCC GAC
1201                                        1231
    ATC CTC TTC CCT GTC AGT GGC GTG GGC TCC TAC AGC CCA GCA GAT GCC CCC CTC GGA AGC
1261                                        1291
    CTG GAG AAC GGG ACA GGA CCA GAG GAC CAC GTT CTC CCG GAT CCT GGA CTT CGG TAC AGT
1321                                        1351
    GTG GAA GCC AGC TCT CCA GGC CAC GGA AGT CCT CTG AGC AGC CTG TTA CCT TCT GCC TCA
1381                                        1411
    GTG CCA GAG TCC ATG ACA ATT AGT GAA CTG CGC CAG GCC ACT GTG GCC ATG ATG AAC AGG
1441                                        1471
    AAG GAT GAG CTG GAG GAG GAG AAC AGA TCA CTG CGA AAC CTG CTC GAC GGT GAG ATG GAG
1501                                        1531
    CAC TCA GCC GCG CTC CGG CAA GAG GTG GAC ACC TTG AAA AGG AAG GTG CTG AAG CAG GAG
1561                                        1591
    GAG CGG CAG GGC ATG AAG GTC CAG GCG CTG GCC AGA GAG AAC GAG GTG CTC AAA GTC CAA
1621                                        1651
    CTG AAG AAA TAT GTA GGA GCT GTC CAG ATG CTG AAA AGA GAA GGT CAA ACA GCT GAA GTG
1681                                        1711
    CCA AAT CTT TGG AGT GTT GAT GGA GAA GTT ACA GTA GCT GAA CAG AAG CCG GGA GAA ATT
1741                                        1771
    GCT GAA GAA CTC GCA AGC TCC TAC GAA AGA AAG CTC ATC GAG GTG GCA GAG ATG CAT GGC
1801                                        1831
    GAG CTG ATT GAG TTC AAC GAG CGC CTG CAC AGG GCC CTG GTA GCC AAG GAA GCC CTC GTG
```

Figure 4

```
1861                              1891
TCC CAG ATG AGG CAG GAG CTC ATC GAT CTC CGG GGA CCG GTG CCT GGA GAT TTG AGT CAA
1921                              1951
ACG TCC GAA GAC CAG AGT TTG TCG GAT TTT GAA ATA TCA AAC CGG GCG CTG ATC AAC GTC
1981                              2011
TGG ATC CCC TCA GTG TTT CTC CGG GGC AAA GCA GCA AAT GCA TTC CAC GTG TAT CAG GTC
2041                              2071
TAC ATC CGG ATA AAA GAC GAT GAA TGG AAT ATT TAT CGC CGG TAT ACA GAG TTC AGG AGT
2101                              2131
TTG CAC CAC AAG TTA CAA AAC AAG TAC CCT CAA GTG AGG GCC TAC AAC TTC CCA CCC AAA
2161                              2191
AAG GCC ATT GGA AAC AAG GAT GCC AAG TTT GTG GAG GAA CGG AGA AAG CAG CTC CAG AAT
2221                              2251
TAC CTG CGC AGC GTC ATG AAC AAA GTC ATC CAG ATG GTC CCC GAG TTC GCT GCC AGC CCC
2281                              2311
AAG AAG GAG ACC CTC ATC CAG CTG ATG CCC TTC TTC GTC GAC ATC ACC CGG CCC GGA GAG
2341                              2371
CCT GTG AAC AGC CGG CCC AAA GCA GCT TCC CGC TTT CCC AAA CTG TCC CGG GGT CAG CCC
2401                              2431
CGG GAG ACC CGC AAC GTG GAG CCC CAG AGC GGT GAC CTC TGA CCT CGA CAA AAC CGC AGC
2461                              2491
CAC GGG CCC TGT GCG TGG CAC CAG CTG CGT CCA CCC CAG CCA CTG CCG CTG GCC CCT CAC
2521                              2551
CTC AGC GTG ACA ACC ACG TCC CAC TGG TGA TCC TGA GAG CAC ACG ATT CCC AAC AGT TAC
2581                              2611
ACA ACA CCC CGA TTA AAC TAA TCA GTC TTC GAG CCG CAT GAT ACC GTG ACC CGA GAG ACC
2641                              2671
AAG GCA GCA CCT CGC TGG AGA GAC TGG GAC ACA CAG TCC TTC TGC TTC TGG GGT CTA CCC
2701                              2731
TGG GCT GCA AGG GCT GTT CCT CCA CCT TCC TAT AGT TCA GGG CTG GCA GGA GGG TGG GCA
2761                              2791
CCA GGT CAG GCT GGG TGC GCC ATG GTT GAG AGG CAA AGG TGA TCC CCT ATA TAG GAA GGT
2821                              2851
TCA TGC AGA GCC AGC CTC TCC ACT CTT TCC CAT GTG GGG ACT AGA ATG ACT ATT AGC CTC
2881                              2911
TTC CTT TGC TTT TTA AGG TTA TTA CCT GGC CTA ACC TAG GGA TGG CTG GCT GTG GGG GGG
2941                              2971
GGG GGT GGG CAT GGT TCC TTT CAC TGC ATT TTC CAC CAA CAG TCA TTA GAC ACC TGG CAC
3001                              3031
TGT CAC AGC TCA CTT TTC CAG AGG GAT ATT CCT GTG GCT TTG GCA AGG AGC CAT TAG TGA
3061                              3091
TGT GCA ACT TGA GTT CAG AGA ACT TCC CCT ACC TCC CCC ATG GCT GGC TTC AGG AAG GAC
3121
CAG TGC CCT CCA TAG CCT G
```

Figure 4 (cont.)

```
ATG AGC GGA TCA CAG AAC AAT GAC AAA AGA CAA TTT CTG CTG GAG CGA CTG CTG GAT GCA
61                                        91
GTG AAA CAG TGC CAG ATC CGC TTT GGA GGG AGA AAG GAG ATT GCC TCG GAT TCC GAC AGC
121                                       151
AGG GTC ACC TGT CTG TGT GCC CAG TTT GAA GCC GTC CTG CAG CAT GGC TTG AAG AGG AGT
181                                       211
CGA GGA TTG GCA CTC ACA GCG GCA GCG ATC AAG CAG GCA GCG GGC TTT GCC AGC AAA ACC
241                                       271
GAA ACA GAG CCC GTG TTC TGG TAC TAC GTG AAG GAG GTC CTC AAC AAG CAC GAG CTG CAG
301                                       331
CGC TTC TAC TCC CTG CGC CAC ATC GCC TCA GAC GTG GGC CGG GGT CGC GCC TGG CTG CGC
361                                       391
TGT GCC CTC AAC GAA CAC TCC CTG GAG CGC TAC CTG CAC ATG CTC CTG GCC GAC CGC TGC
421                                       451
AGG CTG AGC ACT TTT TAT GAA GAC TGG TCT TTT GTG ATG GAT GAA GAA AGG TCC AGT ATG
481                                       511
CTT CCT ACC ATG GCA GCA GGT CTG AAC TCC ATA CTC TTT GCG ATT AAC ATC GAC AAC AAG
541                                       571
GAT TTG AAC GGG CAG AGT AAG TTT GCT CCC ACC GTT TCA GAC CTC TTA AAG GAG TCA ACG
601                                       631
CAG AAC GTG ACC TCC TTG CTG AAG GAG TCC ACG CAA GGA GTG AGC AGC CTG TTC AGG GAG
661                                       691
ATC ACA GCC TCC TCT GCC GTC TCC ATC CTC ATC AAA CCT GAA CAG GAG ACC GAC CCC TTG
721                                       751
CCT GTC GTG TCC AGG AAT GTC AGT GCT GAT GCC AAA TGC AAA AAG GAG CGG AAG AAG AAA
781                                       811
AAG AAA GTG ACC AAC ATA ATC TCA TTT GAT GAT GAG GAA GAT GAG CAG AAC TCT GGG GAC
841                                       871
GTG TTT AAA AAG ACA CCT GGG GCA GGG GAG AGC TCA GAG GAC AAC TCC GAC CGC TCC TCT
901                                       931
GTC AAT ATC ATG TCC GCC TTT GAA AGC CCC TTC GGG CCT AAC TCC AAT GGA AGT CAG AGC
961                                       991
AGC AAC TCA TGG AAA ATT GAT TCC CTG TCT TTG AAC GGG GAG TTT GGG TAC CAG AAG CTT
1021                                      1051
GAT GTG AAA AGC ATC GAT GAT GAA GAT GTG GAT GAA AAC GAA GAT GAC GTG TAT GGA AAC
1081                                      1111
TCA TCA GGA AGG AAG CAC AGG GGC CAC TCG GAG TCG CCC GAG AAG CCA CTG GAA GGG AAC
1141                                      1171
ACC TGC CTC TCC CAG ATG CAC AGC TGG GCT CCG CTG AAG GTG CTG CAC AAT GAC TCC GAC
1201                                      1231
ATC CTC TTC CCT GTC AGT GGC GTG GGC TCC TAC AGC CCA GCA GAT GCC CCC CTC GGA AGC
1261                                      1291
CTG GAG AAC GGG ACA GGA CCA GAG GAC CAC GTT CTC CCG GAT CCT GGA CTT CGG TAC AGT
1321                                      1351
GTG GAA GCC AGC TCT CCA GGC ACC GGA AGT CCT CTG AGC AGC CTG TTA CCT TCT GCC TCA
1381                                      1411
GTG CCA GAG TCC ATG ACA ATT AGT GAA CTG CGC CAG GCC ACT GTG GCC ATG ATG AAC AGG
1441                                      1471
AAG GAT GAG CTG GAG GAG GAG AAC AGA TCA CTG CGA AAC CTG CTC GAC GGT GAG ATG GAG
1501                                      1531
CAC TCA GCC GCG CTC GGG CAA GAG GTG GAC ACC TTG AAA AGG AAG GTG GCT GAA CAG GAG
1561                                      1591
GAG CGG CAG GGC ATG AAG GTC CAG GCG CTG GCC AGA GAG AAC GAG GTG CTC AAA GTC CAA
```

Figure 5

```
1621                                         1651
CTG AAG AAA TAT GTA GGA GCT GTC CAG ATG CTG AAA AGA GAA GGT CAA ACA GCT GAA GTG
1681                                         1711
CCA AAT CTT TGG AGT GTT GAT GGA GAA GTT ACA GTA GCT GAA CAG AAG CCG GGA GAA ATT
1741                                         1771
GCT GAA GAA CTC GCA AGC TCC TAC GAA AGA AAG CTC ATC GAG GTG GCA GAG ATG CAT GGC
1801                                         1831
GAG CTG ATT GAG TTC AAC GAG CGC CTG CAC AGG GCC CTG GTA GCC AAG GAA GCC CTC GTG
1861                                         1891
TCC CAG ATG AGG CAG GAG CTC ATC GAT CTC CGG GGA CCG GTG CCT GGA GAT TTG AGT CAA
1921                                         1951
ACG TCC GAA GAC CAG AGT TTG TCG GAT TTT GAA ATA TCA AAC CGG GCG CTG ATC AAC GTC
1981                                         2011
TGG ATC CCC TCA GTG TTT CTC CGG GGC AAA GCA GCA AAT GCA TTC CAC GTG TAT CAG GTC
2041                                         2071
TAC ATC CGG ATA AAA GAC GAT GAA TGG AAT ATT TAT CGC GGG TAT ACA GAG TTC AGG AGT
2101                                         2131
TTG CAC CAC AAG TTA CAA AAC AAG TAC CCT CAA GTG AGG GCC TAC AAC TTC CCA CCC AAA
2161                                         2191
AAG GCC ATT GGA AAC AAG GAT GCC AAG TTT GTG GAG GAA CGG AGA AAG CAG CTC CAG AAT
2221                                         2251
TAC CTG CGC AGC GTC ATG AAC AAA GTC ATC CAG ATG GTC CCC GAG TTC GCT GCC AGC CCC
2281                                         2311
AAG AAG GAG ACC CTC ATC CAG CTG ATG CCC TTC TTC GTC GAC TGG ATC TCA CTT GTT TGG
2341                                         2371
AAA TGG CCG CGA TAG TTC ACG TGA GGA GTT CTC ATC CTC TTA GCG GCA TCC CCA TGG CCC
2401                                         2431
AGG GTG CAC GGG GGA ATT AGC CTC TCG CGG AGT CAT CAC GCA TCG ACT GAA TTC CCT GGT
2461                                         2491
GAA AAC TGA GTT AGC CAG TTG TTC CTA AGA TAC TCC TGA TGC TGA GAG TGT GAG CAG GAG
2521                                         2551
GCG CTG CCC CAT CCG CAA GTC AGT GTC CCC CAC CCC CTG CGG GGT CCA CAG CCC AGG CAT
2581                                         2611
CTC CGG TCC AGT GTT TCC CAA ACA TTC GCG TGC CGA ATT GTA AAA AGT GCA CGT TAA TGC
2641                                         2671
GAG CCT GTC GGT GTG ACA TGA ATC TCA GCC ATG CTG GTT GCC ATC AGT CAG CAC GGA GAG
2701                                         2731
AGA AAC CTT TTG TGC CTA ATT AGC ACG CAG AAC AGA ACA CAG GGT TCG ATT TAT GGA CTT
2761                                         2791
TTC AAA ACG AGA ATT TCA GTG GGA GAC TGT GGC AAA TGA CAC AGT GTT GAC ACT GGA ATT
2821                                         2851
TTG ACT ACA TGT TGG TCT AGA GCG GCC GCC ACC GCG GTG GAG CTC CAA TTC GT
```

| M | S | G | S | Q | N | N | D | K | R | Q | F | L | L | E |
|---|---|---|---|---|---|---|---|---|---|---|---|---|---|---|
| R | L | L | D | A | V | K | Q | C | Q | I | R | F | G | G |
| R | K | E | I | A | S | D | S | D | S | R | V | T | C | L |
| C | A | Q | F | A | A | V | L | Q | H | G | L | K | R | S |
| R | G | L | A | L | T | A | A | A | I | K | Q | A | A | G |
| F | A | S | K | T | E | T | E | P | V | F | W | Y | Y | V |
| K | E | V | L | N | K | H | E | L | Q | R | F | Y | S | L |
| R | H | I | A | S | D | V | G | R | G | R | A | W | L | R |
| C | A | L | N | E | H | S | L | E | R | Y | L | H | M | L |
| L | A | D | R | C | R | L | S | T | F | Y | E | D | W | S |
| F | V | M | D | E | E | R | S | S | M | L | P | T | M | A |
| A | G | L | N | S | I | L | F | A | I | N | I | D | N | K |
| D | L | N | G | Q | S | K | F | A | P | T | V | S | D | L |
| L | K | E | S | T | Q | N | V | T | S | L | L | K | E | S |
| T | Q | G | V | S | S | L | F | R | E | I | T | A | S | S |
| A | V | S | I | L | I | K | P | E | Q | E | T | D | P | L |
| P | V | V | S | R | N | V | S | A | D | A | K | C | K | K |
| E | R | K | K | K | K | K | V | G | N | I | I | S | F | D |
| D | E | E | D | E | Q | N | S | D | N | V | F | K | K | T |
| P | G | A | G | E | S | S | E | D | P | S | D | R | S | S |
| V | N | I | M | S | A | F | E | S | F | I | G | P | N | S |
| N | G | S | Q | S | S | N | S | W | K | I | D | P | L | I |
| L | N | G | E | F | G | Y | Q | K | L | D | V | K | S | N |
| D | D | E | D | V | D | E | N | E | D | D | V | Y | G | N |

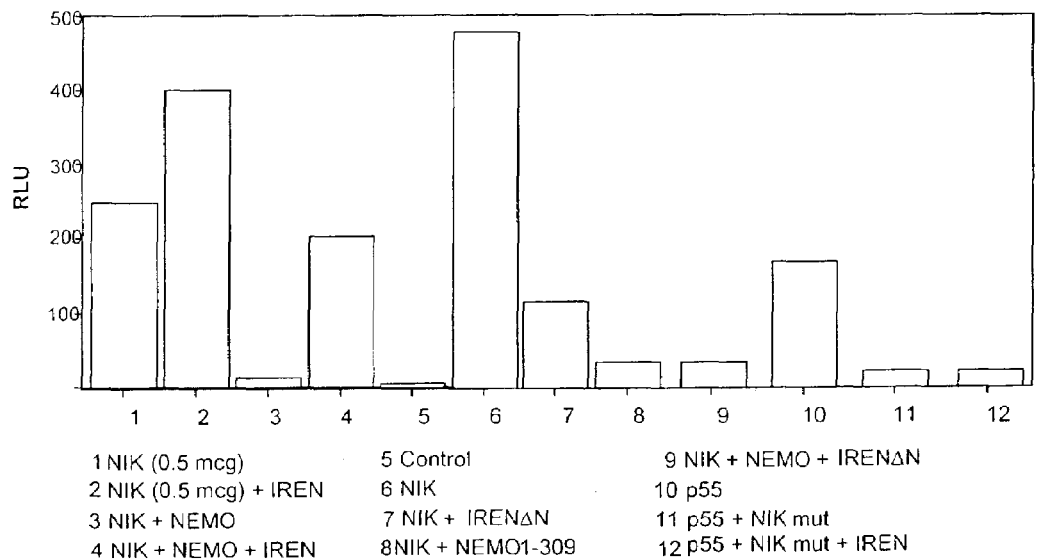
1 NIK (0.5 mcg)
2 NIK (0.5 mcg) + IREN
3 NIK + NEMO
4 NIK + NEMO + IREN
5 Control
6 NIK
7 NIK + IRENΔN
8 NIK + NEMO1-309
9 NIK + NEMO + IRENΔN
10 p55
11 p55 + NIK mut
12 p55 + NIK mut + IREN
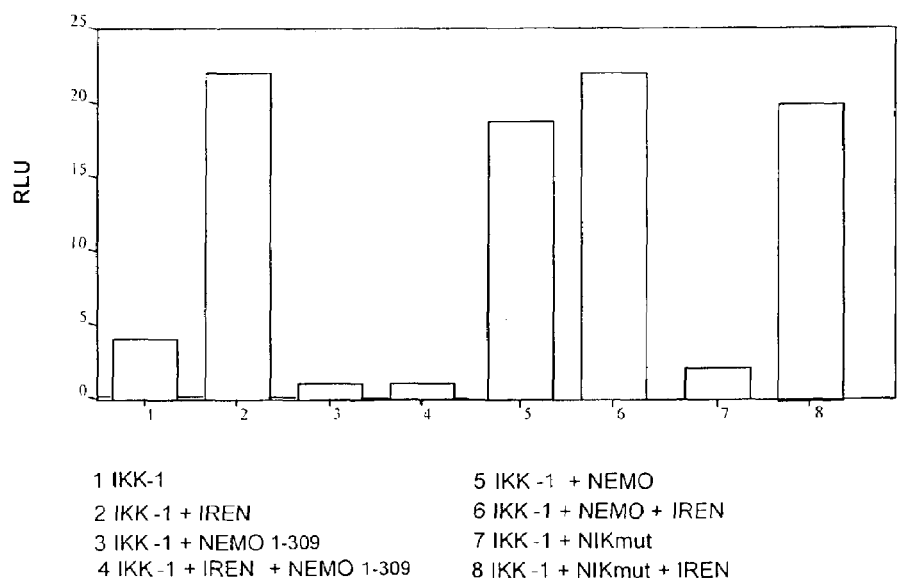
1 IKK-1
2 IKK-1 + IREN
3 IKK-1 + NEMO 1-309
4 IKK-1 + IREN + NEMO 1-309
5 IKK-1 + NEMO
6 IKK-1 + NEMO + IREN
7 IKK-1 + NIKmut
8 IKK-1 + NIKmut + IREN
Figure 10

BLAST results of bases 498 – 699 of 10B open reading frame (parts of putative exon 6 of the 10B gene) against htgs databank

```
>gb|AC007601.3|AC007601 Homo sapiens chromosome 16 clone RP11-276H1, WORKING
DRAFT SEQUENCE, 58
              unordered pieces
          Length = 238514

Score =  398 bits (201), Expect = e-109
 Identities = 201/201 (100%)
 Strand = Plus / Plus Query: 1        ggtctgaactccatactctttgcgattaacatcgacaacaaggatttgaacgggcagagt 60
                ||||||||||||||||||||||||||||| |||||||||||| |||||||||||||||||
Sbjct: 128380   ggtctgaactccatactctttgcgattaacatcgacaacaaggatttgaacgggcagagt
       128439

Query: 61       aagtttgctcccaccgtttcagacctcttaaaggagtcaacgcagaacgtgacctccttg 120
                ||||||:|||||||||||||||||||||||||||||||||||||||||||||||||||||
Sbjct: 128440   aagtttgctcccaccgtttcagacctcttaaaggagtcaacgcagaacgtgacctccttg
       128499

Query: 121      ctgaaggagtccacgcaaggagtgagcagcctgttcagggagatcacagcctcctctgcc 180
                ||||||||||||||||||||||||||||||||||||||||||||||||||||||||||||
Sbjct: 128500   ctgaaggagtccacgcaaggagtgagcagcctgttcagggagatcacagcctcctctgcc
       128559

Query: 181      gtctccatcctcatcaaacct 201
                |||||||||||||||||||||
Sbjct: 128560   gtctccatcctcatcaaacct 128580

>gb|AC034281.2|AC034281 Homo sapiens chromosome 4 clone RP11-656O6 map 4,
WORKING DRAFT SEQUENCE,
             32 unordered pieces
          Length = 205309

Score =  398 bits (201), Expect = e-109
 Identities = 201/201 (100%)
 Strand = Plus / Minus Query: 1        ggtctgaactccatactctttgcgattaacatcgacaacaaggatttgaacgggcagagt 60
                ||||||||||||||||||||||||||||||||||||||||||||||||||||||||||||
Sbjct: 119945   ggtctgaactccatactctttgcgattaacatcgacaacaaggatttgaacgggcagagt
       119886

Query: 61       aagtttgctcccaccgtttcagacctcttaaaggagtcaacgcagaacgtgacctccttg 120
                ||||||||||||||||||||||||||||||||||||||||||||||||||||||||||||
Sbjct: 119885   aagtttgctcccaccgtttcagacctcttaaaggagtcaacgcagaacgtgacctccttg
       119826

Query: 121      ctgaaggagtccacgcaaggagtgagcagcctgttcagggagatcacagcctcctctgcc 180
                ||||||||||||||||||||||||||||||||||||||||||||||||||||||||||||
Sbjct: 119825   ctgaaggagtccacgcaaggagtgagcagcctgttcagggagatcacagcctcctctgcc
       119766
```

Figure 13A

```
Query: 181      gtctccatcctcatcaaacct 201
                |||||||||||||||||||||
Sbjct: 119765   gtctccatcctcatcaaacct 119745
```

>gb|AC008864.6|AC008864 Homo sapiens chromosome 16 clone CTD-2192M20, WORKING
DRAFT SEQUENCE, 9
          ordered pieces
        Length = 140011

Score =  331 bits (167), Expect = 1e-88
 Identities = 193/201 (96%), Gaps = 3/201 (1%)
 Strand = Plus / Plus

```
Query: 1        ggtctgaactccatactctttgcgattaacatcgacaacaaggatttgaacgggcagagt 60
                ||||  ||||||||||||||||||||||||| |||||||||||||||||||||||||||
Sbjct: 86177    ggtccgaactccatactctttgcgattaacattgacaacaaggatttgaacgggcagagt 86236

Query: 61       aagtttgctcccaccgtttcagacctcttaaaggagtcaacgcagaacgtgacctccttg 120
                |||||||||||||||||||||||||||||||||||||||||||||||| ||||   |||||
Sbjct: 86237    aagtttgctcccaccgtttcagacctcttaaaggagtcaacgcagaatgtga---ccttg 86293

Query: 121      ctgaaggagtccacgcaaggagtgagcagcctgttcagggagatcacagcctcctctgcc 180
                |||||||||||||||||||||||||||||||| |||||||||||||||||||||||||||
Sbjct: 86294    ctgaaggagtccacgcaaggagtgagcagcgtgttcagggagatcacagcctcctctgcc 86353

Query: 181      gtctccatcctcatcaaacct 201
                 ||||||||||||||| |||
Sbjct: 86354    atctccatcctcatcaaacct 86374
```

>gb|AC008740.5|AC008740 Homo sapiens chromosome 16 clone CTD-2547E10, WORKING
DRAFT SEQUENCE, 4
          ordered pieces
        Length = 157848

Score =  331 bits (167), Expect = 1e-88
 Identities = 193/201 (96%), Gaps = 3/201 (1%)
 Strand = Plus / Plus

```
Query: 1        ggtctgaactccatactctttgcgattaacatcgacaacaaggatttgaacgggcagagt 60
                ||||  ||||||||||||||||||||||||| |||||||||||||||||||||||||||
Sbjct: 90259    ggtccgaactccatactctttgcgattaacattgacaacaaggatttgaacgggcagagt 90318

Query: 61       aagtttgctcccaccgtttcagacctcttaaaggagtcaacgcagaacgtgacctccttg 120
                ||||||||||||||||||||||||||||||||||||||||||||||| ||||   |||||
Sbjct: 90319    aagtttgctcccaccgtttcagacctcttaaaggagtcaacgcagaatgtga---ccttg 90375

Query: 121      ctgaaggagtccacgcaaggagtgagcagcctgttcagggagatcacagcctcctctgcc 180
                |||||||||||||||||||||||||||||||| |||||||||||||||||||||||||||
Sbjct: 90376    ctgaaggagtccacgcaaggagtgagcagcgtgttcagggagatcacagcctcctctgcc 90435

Query: 181      gtctccatcctcatcaaacct 201
                 ||||||||||||||||||||
Sbjct: 90436    atctccatcctcatcaaacct 90456
```

Figure 13A (cont.)

```
>gb|AC025279.2|ACC25279 Homo sapiens chromosome 16 clone RP11-231C14, WORKING
DRAFT SEQUENCE, 25
          unordered pieces
       Length = 183752

Score =  331 bits (167), Expect = 1e-88
 Identities = 193/201 (96%), Gaps = 3/201 (1%)
 Strand = Plus / Plus Query: 1       ggtctgaactccatactctttgcgattaacatcgacaacaaggatttgaacgggcagagt 60
               |||| |||||||||||||||||||||||||| |||||||||||||||||||||||||||
Sbjct: 156098  ggtccgaactccatactctttgcgattaacattgacaacaaggatttgaacgggcagagt
156157

Query: 61      aagtttgctcccaccgtttcagacctcttaaaggagtcaacgcagaacgtgacctccttg 120
               |||||||||||||||||||||||||||||||||||||||||||||||  ||||   ||||
Sbjct: 156158  aagtttgctcccaccgtttcagacctcttaaaggagtcaacgcagaatgtga---ccttg
156214

Query: 121     ctgaaggagtccacgcaaggagtgagcagcctgttcagggagatcacagcctcctctgcc 180
               ||||||||||||||||||||||||||||||| ||||||||||||||||||||||||||||
Sbjct: 156215  ctgaaggagtccacgcaaggagtgagcagcgtgttcagggagatcacagcctcctctgcc
156274

Query: 181     gtctccatcctcatcaaacct 201
               ||||||||||||||||||| |
Sbjct: 156275  atctccatcctcatcaaacct 156295

>gb|AC023814.3|AC023814 Homo sapiens chromosome 16 clone CTD-2159J19, WORKING
DRAFT SEQUENCE,
          19 unordered pieces
       Length = 181463

Score =  331 bits (167), Expect = 1e-88
 Identities = 193/201 (96%), Gaps = 3/201 (1%)
 Strand = Plus / Plus Query: 1       ggtctgaactccatactctttgcgattaacatcgacaacaaggatttgaacgggcagagt 60
               |||| |||||||||||||||||||||||||| |||||||||||||||||||||||||||
Sbjct: 55839   ggtccgaactccatactctttgcgattaacattgacaacaaggatttgaacgggcagagt 55898

Query: 61      aagtttgctcccaccgtttcagacctcttaaaggagtcaacgcagaacgtgacctccttg 120
               |||||||||||||||||||||||||||||||||||||||||||||||  ||||   ||||
Sbjct: 55899   aagtttgctcccaccgtttcagacctcttaaaggagtcaacgcagaatgtga---ccttg 55955

Query: 121     ctgaaggagtccacgcaaggagtgagcagcctgttcagggagatcacagcctcctctgcc 180
               ||||||||||||||||||||||||||||||| ||||||||||||||||||||||||||||
Sbjct: 55956   ctgaaggagtccacgcaaggagtgagcagcgtgttcagggagatcacagcctcctctgcc 56015

Query: 181     gtctccatcctcatcaaacct 201
               |||||||||||||||||||||
Sbjct: 56016   atctccatcctcatcaaacct 56036
```

Figure 13A (cont.)

```
>gb|AC069176.3|AC069176 Homo sapiens chromosome 11 clone RP11-1122L9 map 11,
WORKING DRAFT
            SEQUENCE, 23 unordered pieces
         Length = 155414

Score =  331 bits (167), Expect = 1e-88
 Identities = 193/201 (96%), Gaps = 3/201 (1%)
 Strand = Plus / Minus Query: 1      ggtctgaactccatactctttgcgattaacatcgacaacaaggatttgaacgggcagagt 60
              ||||  ||||| ||||||||||||||||||||| |||||||||||||||||||||||||
Sbjct: 10308  ggtccgaactccatactctttgcgattaacattgacaacaaggatttgaacgggcagagt 10249

Query: 61     aagtttgctcccaccgtttcagacctcttaaaggagtcaacgcagaacgtgacctccttg 120
              |||||||||||||||||||||||||||||||||||||||||||||||| ||||   ||||
Sbjct: 10248  aagtttgctcccaccgtttcagacctcttaaaggagtcaacgcagaatgtgac---cttg 10192

Query: 121    ctgaaggagtccacgcaaggagtgagcagcctgttcagggagatcacagcctcctctgcc 180
              |||||||||||||||||||||||||||||| ||||||||||||||||||||||||||||
Sbjct: 10191  ctgaaggagtccacgcaaggagtgagcagcgtgttcagggagatcacagcctcctctgcc 10132

Query: 181    gtctccatcctcatcaaacct 201
               |||||||||||||||||||
Sbjct: 10131  atctccatcctcatcaaacct 10111

>gb|AC023463.2|AC023463 Homo sapiens chromosome 7 clone RP11-403M2 map 7,
WORKING DRAFT
            SEQUENCE, 33 unordered pieces
         Length = 178081

Score =  323 bits (163), Expect = 3e-86
 Identities = 192/201 (95%), Gaps = 3/201 (1%)
 Strand = Plus / Plus Query: 1      ggtctgaactccatactctttgcgattaacatcgacaacaaggatttgaacgggcagagt 60
              ||||  |||||||||||||||||||||||| ||||||||||||||||||||||||||||
Sbjct: 55935  ggtccgaactccatactctttgcgattaacattgacaacaaggatttgaacgggcagagt 55994

Query: 61     aagtttgctcccaccgtttcagacctcttaaaggagtcaacgcagaacgtgacctccttg 120
              |||||||||||||||||||||||||||||||||||||||||||||||| ||||   ||||
Sbjct: 55995  aagtttgctcccaccgtttcagacctcttaaaggagtcaacgcagaatgtga---acttg 56051

Query: 121    ctgaaggagtccacgcaaggagtgagcagcctgttcagggagatcacagcctcctctgcc 180
              |||||||||||||||||||||||||||||| ||||||||||||||||||||||||||||
Sbjct: 56052  ctgaaggagtccacgcaaggagtgagcagcgtgttcagggagatcacagcctcctctgcc 56111

Query: 181    gtctccatcctcatcaaacct 201
               |||||||||||||||||||
Sbjct: 56112  atctccatcctcatcaaacct 56132

>gb|AC073921.1|AC073921 Homo sapiens chromosome 11 clone RP11-509A19 map 11,
LOW-PASS SEQUENCE
            SAMPLING
         Length = 60516
```

Figure 13A (cont.)

```
Score =  228 bits (115), Expect = 1e-57
Identities = 143/152 (94%), Gaps = 3/152 (1%)
Strand = Plus / Plus Query: 50     acgggcagagtaagtttgctcccaccgtttcagacctcttaaagcagtcaacgcagaacg 109
              ||||||||  ||||||||||||||||||||||||||||||||||||||||||||||||| |
Sbjct: 59840  acgggcagnataagtttgctcccaccgtttcagacctcttaaaggagtcaacgcagaatg 59899

Query: 110    tgacctccttgctgaaggagtccacgcaaggagtgagcagcctgttcagggagatcacag 169
              ||| ||   |||||||||||||||||||||||||||||||| ||||||||||||||||||
Sbjct: 59900  tgaact---tgctgaaggagtccacgcaaggagtgagcagcgtgttcagggagatcacag 59956

Query: 170    cctcctctgccgtctccatcctcatcaaacct 201
              |||||||||||  |||||||||||||||||||
Sbjct: 59957  cctcctctgccatctccatcctcatcaaacct 59988
```

Figure 13A (cont.)

BLAST results of bases 498 – 699 of 10B open reading frame (parts of putative exon 6 of the 10B gene) against the est databank

```
>gb|AI369689.1|AI369689 qy71g08.x1 NCI_CGAP_Brn25 Homo sapiens cDNA clone
IMAGE:2017502 3'
          Length = 439

Score =  398 bits (201), Expect = e-109
 Identities = 201/201 (100%)
 Strand = Plus / Minus Query: 1    ggtctgaactccatactctttgcgattaacatcgacaacaaggatttgaacgggcagagt 60
            ||||||||||||||||||||||||||||||||||||||||||||||||||||||||||||
Sbjct: 276  ggtctgaactccatactctttgcgattaacatcgacaacaaggatttgaacgggcagagt 217

Query: 61   aagtttgctcccaccgtttcagacctcttaaaggagtcaacgcagaacgtgacctccttg 120
            ||||||||||||||||||||||||||||||||||||||||||||||||||||||||||||
Sbjct: 216  aagtttgctcccaccgtttcagacctcttaaaggagtcaacgcagaacgtgacctccttg 157

Query: 121  ctgaaggagtccacgcaaggagtgagcagcctgttcagggagatcacagcctcctctgcc 180
            ||||||||||||||||||||||||||||||||||||||||||||||||||||||||||||
Sbjct: 156  ctgaaggagtccacgcaaggagtgagcagcctgttcagggagatcacagcctcctctgcc 97

Query: 181  gtctccatcctcatcaaacct 201
            |||||||||||||||||||||
Sbjct: 96   gtctccatcctcatcaaacct 76

>gb|AW503340.1|AW503340 UI-HF-BN0-akx-f-06-0-UI.r1 NIH_MGC_50 Homo sapiens cDNA
clone
          IMAGE:3078682 5'.
          Length = 520

Score =  331 bits (167), Expect = 6e-89
 Identities = 193/201 (96%), Gaps = 3/201 (1%)
 Strand = Plus / Plus Query: 1    ggtctgaactccatactctttgcgattaacatcgacaacaaggatttgaacgggcagagt 60
            |||| ||||||||||||||||||||||||| |||||||||||||||||||||||||||||
Sbjct: 190  ggtccgaactccatactctttgcgattaacattgacaacaaggatttgaacgggcagagt 249

Query: 61   aagtttgctcccaccgtttcagacctcttaaaggagtcaacgcagaacgtgacctccttg 120
            |||||||||||||||||||||||||||||||||||||||||||||||||| ||||  ||||
Sbjct: 250  aagtttgctcccaccgtttcagacctcttaaaggagtcaacgcagaatgta---ccttg 306

Query: 121  ctgaaggagtccacgcaaggagtgagcagcctgttcagggagatcacagcctcctctgcc 180
            ||||||||||||||||||||||||||||| ||||||||||||||||||||||||||||||
Sbjct: 307  ctgaaggagtccacgcaaggagtgagcagcgtgttcagggagatcacagcctcctctgcc 366

Query: 181  gtctccatcctcatcaaacct 201
            ||||||||||||||||||||
Sbjct: 367  atctccatcctcatcaaacct 387
```

Figure 13B

```
>gb|AW403206.1|AW403206 UI-HF-BK0-aay-f-08-0-UI.r1 NIH_MGC_36 Homo sapiens cDNA
clone
          IMAGE:3055622 5'.
          Length = 430

Score =  331 bits (167), Expect = 6e-89
 Identities = 193/201 (96%), Gaps = 3/201 (1%)
 Strand = Plus / Plus Query: 1    ggtctgaactccatactctttgcgattaacatcgacaacaaggatttgaacgggcagagt 60
            |||| ||||||||||||||||||||||||| |||||||||||||||||||||||||||||
Sbjct: 86   ggtccgaactccatactctttgcgattaacattgacaacaaggatttgaacgggcagagt 145

Query: 61   aagtttgctcccaccgtttcagacctcttaaaggagtcaacgcagaacgtgacctccttg 120
            ||||||||||||||||||||||||||||||||||||||||||||||||||| |||  |||||
Sbjct: 146  aagtttgctcccaccgtttcagacctcttaaaggagtcaacgcagaatgtga---ccttg 202

Query: 121  ctgaaggagtccacgcaaggagtgagcagcctgttcagggagatcacagcctcctctgcc 180
            |||||||||||||||||||||||||||||||| |||||||||||||||||||||||||||
Sbjct: 203  ctgaaggagtccacgcaaggagtgagcagcgtgttcagggagatcacagcctcctctgcc 262

Query: 181  gtctccatcctcatcaaacct 201
            |||||||||||||||||||||
Sbjct: 263  atctccatcctcatcaaacct 283

>gb|AW206027.1|AW206027 UI-H-BI1-afy-h-03-0-UI.s1 NCI_CGAP_Sub3 Homo sapiens
cDNA clone
          IMAGE:2723572 3'.
          Length = 332

Score =  331 bits (167), Expect = 6e-89
 Identities = 193/201 (96%), Gaps = 3/201 (1%)
 Strand = Plus / Minus Query: 1    ggtctgaactccatactctttgcgattaacatcgacaacaaggatttgaacgggcagagt 60
            |||| ||||||||||||||||||||||||| |||||||||||||||||||||||||||||
Sbjct: 275  ggtccgaactccatactctttgcgattaacattgacaacaaggatttgaacgggcagagt 216

Query: 61   aagtttgctcccaccgtttcagacctcttaaaggagtcaacgcagaacgtgacctccttg 120
            ||||||||||||||||||||||||||||||||||||||||||||||||||| |||  |||
Sbjct: 215  aagtttgctcccaccgtttcagacctcttaaaggagtcaacgcagaatgtgac---cttg 159

Query: 121  ctgaaggagtccacgcaaggagtgagcagcctgttcagggagatcacagcctcctctgcc 180
            |||||||||||||||||||||||||||||||| |||||||||||||||||||||||||||
Sbjct: 158  ctgaaggagtccacgcaaggagtgagcagcgtgttcagggagatcacagcctcctctgcc 99

Query: 181  gtctccatcctcatcaaacct 201
            |||||||||||||||||||||
Sbjct: 98   atctccatcctcatcaaacct 78

>gb|AA584128.1|AA584128 no10g11.s1 NCI_CGAP_Phe1 Homo sapiens cDNA clone
IMAGE:1100324 3'
          similar to contains element XTR repetitive element ;.
          Length = 414
```

Figure 13B (cont.)

```
Score =  331 bits (167), Expect = 6e-89
Identities = 193/201 (96%), Gaps = 3/201 (1%)
Strand = Plus / Minus Query: 1    ggtctgaactccatactctttgcgattaacatcgacaacaaggatttgaacgggcagagt 60
            ||||  |||||||||||||||||||||||||| ||||||||||| ||||||||||||||
Sbjct: 217  ggtccgaactccatactctttgcgattaacattgacaacaaggatttgaacgggcagagt 158

Query: 61   aagtttgctcccaccgtttcagacctcttaaaggagtcaacgcagaacgtgacctccttg 120
            ||||||||||||||||||||||||||||||||||||||||||||||| ||||   ||||
Sbjct: 157  aagtttgctcccaccgtttcagacctcttaaaggagtcaacgcagaatgtgac---cttg 101

Query: 121  ctgaaggagtccacgcaaggagtgagcagcctgttcagggagatcacagcctcctctgcc 180
            ||||||||||||||||||||||||||||||  ||||||||||||||||||||||||||||
Sbjct: 100  ctgaaggagtccacgcaaggagtgagcagcgtgttcagggagatcacagcctcctctgcc 41

Query: 181  gtctccatcctcatcaaacct 201
            |||||||||||||||||||||
Sbjct: 40   atctccatcctcatcaaacct 20
```

Figure 13B (cont.)

```
                        SEQUENCE LISTING

<160> NUMBER OF SEQ ID NOS: 14

<210> SEQ ID NO 1
<211> LENGTH: 30
<212> TYPE: DNA
<213> ORGANISM: Artificial sequence
<220> FEATURE:
<223> OTHER INFORMATION: synthetic

<400> SEQUENCE: 1
caggatcctc atggctgcag ctagcgtgac                                      30

<210> SEQ ID NO 2
<211> LENGTH: 32
<212> TYPE: DNA
<213> ORGANISM: Artificial sequence
<220> FEATURE:
<223> OTHER INFORMATION: synthetic

<400> SEQUENCE: 2
ggtcgactta gagccctgtc aggtccacaa tg                                   32

<210> SEQ ID NO 3
<211> LENGTH: 143
<212> TYPE: DNA
<213> ORGANISM: Homo sapiens

<400> SEQUENCE: 3
ggtaccgagc tcggatccac tagtaacggc cgccagtgtg ctggaattct gcggatgtac     60
ccatacgatg ttccagatac gctgaatttc gaggccacga aggccggcgg cgcggcgcag    120
gcaccggccc ggggagaggc acc                                            143

<210> SEQ ID NO 4
<211> LENGTH: 1782
```

```
<212> TYPE: DNA
<213> ORGANISM: Homo sapiens

<400> SEQUENCE: 4
atgagcggat cacagaacaa tgacaaaaga caatttctgc tggagcgact gctggatgca      60
gtgaaacagt gccagatccg ctttggaggg agaaaggaga ttgcctcgga ttccgacagc     120
agggtcacct gtctgtgtgc ccagtttgaa gccgtcctgc agcatggctt gaagaggagt     180
cgaggattgg cactcacagc ggcagcgatc aagcaggcag cgggctttgc cagcaaaacc     240
gaaacagagc ccgtgttctg gtactacgtg aaggaggtcc tcaacaagca cgagctgcag     300
cgcttctact ccctgcgcca catcgcctca gacgtgggcc ggggtcgcgc ctggctgcgc     360
tgtgccctca cgaacactc cctggagcgc tacctgcaca tgctcctggc cgaccgctgc     420
aggctgagca cttttttatga agactggtct tttgtgatgg atgaagaaag gtccagtatg     480
cttcctacca tggcagcagg tctgaactcc atactctttg cgattaacat cgacaacaag     540
gatttgaacg ggcagagtaa gtttgctccc accgtttcag acctcttaaa ggagtcaacg     600
cagaacgtga cctccttgct gaaggagtcc acgcaaggag tgagcagcct gttcagggag     660
atcacagcct cctctgccgt ctccatcctc atcaaacctg aacaggagac cgacccctg     720
cctgtcgtgt ccaggaatgt cagtgctgat gccaaatgca aaaaggagcg gaagaagaaa     780
aagaaagtga ccaacataat ctcatttgat gatgaggaag atgagcagaa ctctggggac     840
gtgtttaaaa agacacctgg ggcaggggag agctcagagg acaactccga ccgctcctct     900
gtcaatatca tgtccgcctt tgaaagcccc ttcgggccta actccaatgg aagtcagagc     960
agcaactcat ggaaaattga ttccctgtct ttgaacgggg agtttgggta ccagaagctt    1020
gatgtgaaaa gcatcgatga tgaagatgtg atgaaaacg aagatgacgt gtatggaaac    1080
tcatcaggaa ggaagcacag gggccactcg gagtcgcccg agaagccact ggaagggaac    1140
acctgcctct cccagatgca cagctgggct ccgctgaagg tgctgcacaa tgactccgac    1200
atcctcttcc ctgtcagtgg cgtgggctcc tacagcccag cagatgcccc cctcggaagc    1260
ctggagaacg ggacaggacc agaggaccac gttctcccgg atcctggact cggtacagt    1320
gtggaagcca gctctccagg ccacggaagt cctctgagca gcctgttacc ttctgcctca    1380
gtgccagagt ccatgacaat tagtgaactg cgccaggcca ctgtggccat gatgaacagg    1440
aaggatgagc tggaggagga aacagatca ctgcgaaacc tgctcgacgg tgagatggag    1500
cactcagccg cgctccggca agaggtggac accttgaaaa ggaaggtggc tgaacaggag    1560
gagcggcagg gcatgaaggt ccaggcgctg ccagctatc tttgctattt tgtgaggaga    1620
ttctaacccc acgtgagaac catgtggtgg agaaatggag ggagagagaa atccaacagt    1680
tcctgatagt ctcatttgag ctcctggatc cagtctttcc tgaagctgtg tttcctctgg    1740
acttttcatg tatgtgagcc aataaattgc tttcattcct tg                       1782

<210> SEQ ID NO 5
<211> LENGTH: 3139
<212> TYPE: DNA
<213> ORGANISM: Homo sapiens

<400> SEQUENCE: 5
atgagcggat cacagaacaa tgacaaaaga caatttctgc tggagcgact gctggatgca      60
gtgaaacagt gccagatccg ctttggaggg agaaaggaga ttgcctcgga ttccgacagc     120
agggtcacct gtctgtgtgc ccagtttgaa gccgtcctgc agcatggctt gaagaggagt     180
```

```
cgaggattgg cactcacagc ggcagcgatc aagcaggcag cgggcttttgc cagcaaaacc    240 gaaacagagc ccgtgttctg gtactacgtg aaggaggtcc tcaacaagca cgagctgcag    300
cgcttctact ccctgcgcca catcgcctca gacgtgggcc ggggtcgcgc ctggctgcgc    360
tgtgccctca acgaacactc cctggagcgc tacctgcaca tgctcctggc cgaccgctgc    420
aggctgagca cttttttatga agactggtct tttgtgatgg atgaagaaag gtccagtatg    480
cttcctacca tggcagcagg tctgaactcc atactctttg cgattaacat cgacaacaag    540
gatttgaacg ggcagagtaa gtttgctccc accgtttcag acctcttaaa ggagtcaacg    600
cagaacgtga cctccttgct gaaggagtcc acgcaaggag tgagcagcct gttcagggag    660
atcacagcct cctctgccgt ctccatcctc atcaaacctg aacaggagac cgaccccttg    720
cctgtcgtgt ccaggaatgt cagtgctgat gccaaatgca aaaaggagcg gaagaagaaa    780
aagaaagtga ccaacataat ctcatttgat gatgaggaag atgagcagaa ctctggggac    840
gtgtttaaaa agacacctgg ggcaggggag agctcagagg acaactccga ccgctcctct    900
gtcaatatca tgtccgcctt tgaaagcccc ttcgggccta actccaatgg aagtcagagc    960
agcaactcat ggaaaattga ttccctgtct ttgaacgggg agtttgggta ccagaagctt   1020
gatgtgaaaa gcatcgatga tgaagatgtg gatgaaaacg aagatgacgt gtatggaaac   1080
tcatcaggaa ggaagcacag gggccactcg gagtcgcccg agaagccact ggaagggaac   1140
acctgcctct cccagatgca cagctgggct ccgctgaagg tgctgcacaa tgactccgac   1200
atcctcttcc ctgtcagtgg cgtgggctcc tacagcccag cagatgcccc cctcggaagc   1260
ctggagaacg ggacaggacc agaggaccac gttctcccgg atcctggact tcggtacagt   1320
gtggaagcca gctctccagg ccacggaagt cctctgagca gcctgttacc ttctgcctca   1380
gtgccagagt ccatgacaat tagtgaactg cgccaggcca ctgtggccat gatgaacagg   1440
aaggatgagc tggaggagga gaacagatca ctgcgaaacc tgctcgacgg tgagatggag   1500
cactcagccg cgctccggca agaggtggac accttgaaaa ggaaggtggc tgaacaggag   1560
gagcggcagg gcatgaaggt ccaggcgctg ccagagaga acgaggtgct caaagtccaa   1620
ctgaagaaat atgtaggagc tgtccagatg ctgaaaagag aaggtcaaac agctgaagtg   1680
ccaaatcttt ggagtgttga tggagaagtt acagtagctg aacagaagcc gggagaaatt   1740
gctgaagaac tcgcaagctc ctacgaaaga aagctcatcg aggtggcaga gatgcatggc   1800
gagctgattg agttcaacga gcgcctgcac agggccctgg tagccaagga agccctcgtg   1860
tcccagatga ggcaggagct catcgatctc cggggaccgg tgcctggaga tttgagtcaa   1920
acgtccgaag accagagttt gtcggatttt gaaatatcaa accgggcgct gatcaacgtc   1980
tggatcccct cagtgtttct ccggggcaaa gcagcaaatg cattccacgt gtatcaggtc   2040
tacatccgga taaaagacga tgaatggaat atttatcgcc ggtatacaga gttcaggagt   2100
ttgcaccaca agttacaaaa caagtaccct caagtgaggg cctacaactt cccacccaaa   2160
aaggccattg gaaacaagga tgccaagttt gtggaggaac ggagaaagca gctccagaat   2220
tacctgcgca gcgtcatgaa caaagtcatc cagatggtcc ccgagttcgc tgccagcccc   2280
aagaaggaga ccctcatcca gctgatgccc ttcttcgtcg acatcacccc gcccggagag   2340
cctgtgaaca gccggcccaa agcagcttcc cgctttccca actgtcccg gggtcagccc   2400 cgggagaccc gcaacgtgga gccccagagc ggtgacctct gacctcgaca aaaccgcagc   2460
cacgggccct gtgcgtggca ccagctgcgt ccaccccagc cactgccgct ggcccctcac   2520
ctcagcgtga caaccacgtc ccactggtga tcctgagagc acacgattcc caacagttac   2580
```

```
acaacacccc gattaaacta atcagtcttc gagccgcatg ataccgtgac ccgagagacc    2640
aaggcagcac ctcgctggag agactgggac acacagtcct tctgcttctg gggtctaccc    2700
tgggctgcaa gggctgttcc tccaccttcc tatagttcag ggctggcagg agggtgggca    2760
ccaggtcagg ctgggtgcgc catggttgag aggcaaaggt gatccctat ataggaaggt     2820 tcatgcagag ccagcctctc cactctttcc catgtgggga ctagaatgac tattagcctc    2880
ttcctttgct ttttaaggtt attacctggc ctaacctagg gatggctggc tgtgggggg     2940 gggggtgggc atggttcctt tcactgcatt ttccaccaac agtcattaga cacctggcac    3000
tgtcacagct cacttttcca gagggatatt cctgtggctt tggcaaggag ccattagtga    3060
tgtgcaactt gagttcagag aacttcccct acctccccca tggctggctt caggaaggac    3120
cagtgccctc catagcctg                                                 3139
```

<210> SEQ ID NO 6
<211> LENGTH: 2873
<212> TYPE: DNA
<213> ORGANISM: Homo sapiens

<400> SEQUENCE: 6

```
atgagcggat cacagaacaa tgacaaaaga caatttctgc tggagcgact gctggatgca     60
gtgaaacagt gccagatccg ctttggaggg agaaaggaga ttgcctcgga ttccgacagc    120
agggtcacct gtctgtgtgc ccagtttgaa gccgtcctgc agcatggctt gaagaggagt    180
cgaggattgg cactcacagc ggcagcgatc aagcaggcag cgggctttgc cagcaaaacc    240
gaaacagagc ccgtgttctg gtactacgtg aaggaggtcc tcaacaagca cgagctgcag    300
cgcttctact ccctgcgcca catcgcctca gacgtgggcc ggggtcgcgc ctggctgcgc    360
tgtgccctca cgaacacactc cctggagcgc tacctgcaca tgctcctggc cgaccgctgc    420
aggctgagca ctttttatga agactggtct tttgtgatgg atgaagaaag gtccagtatg    480
cttcctacca tggcagcagg tctgaactcc atactctttg cgattaacat cgacaacaag    540
gatttgaacg ggcagagtaa gtttgctccc accgtttcag acctcttaaa ggagtcaacg    600
cagaacgtga cctccttgct gaaggagtcc acgcaaggag tgagcagcct gttcagggag    660
atcacagcct cctctgccgt ctccatcctc atcaaacctg aacaggagac cgacccttg    720 cctgtcgtgt ccaggaatgt cagtgctgat gccaaatgca aaaggagcg gaagaagaaa    780 aagaaagtga ccaacataat ctcatttgat gatgaggaag atgagcagaa ctctggggac    840
gtgtttaaaa agacacctgg ggcaggggag agctcagagg acaactccga ccgctcctct    900
gtcaatatca tgtccgcctt tgaaagcccc ttcgggccta actccaatgg aagtcagagc    960
agcaactcat ggaaaattga ttccctgtct ttgaacgggg agtttgggta ccagaagctt   1020
gatgtgaaaa gcatcgatga tgaagatgtg atgaaaacg aagatgacgt gtatggaaac    1080
tcatcaggaa ggaagcacag gggccactcg gagtcgcccg agaagccact ggaagggaac    1140
acctgcctct cccagatgca cagctgggct ccgctgaagg tgctgcacaa tgactccgac    1200
atcctcttcc ctgtcagtgg cgtgggctcc tacagcccag cagatgcccc cctcggaagc    1260
ctggagaacg ggacaggacc agaggaccac gttctcccgg atcctggact tcggtacagt    1320
gtggaagcca gctctccagg ccacggaagt cctctgagca gcctgttacc ttctgcctca    1380
gtgccagagt ccatgacaat tagtgaactg cgccaggcca ctgtggccat gatgaacagg    1440
aaggatgagc tggaggagga gaacagatca ctgcgaaacc tgctcgacgg tgagatggag    1500
```

```
cactcagccg cgctccggca agaggtggac accttgaaaa ggaaggtggc tgaacaggag    1560
gagcggcagg gcatgaaggt ccaggcgctg gccagagaga cgaggtgct caaagtccaa     1620 ctgaagaaat atgtaggagc tgtccagatg ctgaaaagag aaggtcaaac agctgaagtg    1680 ccaaatctt  ggagtgttga tggagaagtt acagtagctg aacagaagcc gggagaaatt    1740
gctgaagaac tcgcaagctc ctacgaaaga aagctcatcg aggtggcaga gatgcatggc    1800
gagctgattg agttcaacga gcgcctgcac agggccctgg tagccaagga agccctcgtg    1860
tcccagatga ggcaggagct catcgatctc cggggaccgg tgcctggaga tttgagtcaa    1920
acgtccgaag accagagttt gtcggatttt gaaatatcaa accgggcgct gatcaacgtc    1980
tggatcccct cagtgtttct ccggggcaaa gcagcaaatg cattccacgt gtatcaggtc    2040
tacatccgga taaagacga tgaatggaat atttatcgcc ggtatacaga gttcaggagt     2100
ttgcaccaca agttacaaaa caagtaccct caagtgaggg cctacaactt cccacccaaa    2160
aaggccattg aaacaagga tgccaagttt gtggaggaac ggagaaagca gctccagaat     2220
tacctgcgca gcgtcatgaa caaagtcatc cagatggtcc ccgagttcgc tgccagcccc   2280
aagaaggaga ccctcatcca gctgatgccc ttcttcgtcg actggatctc acttgtttgg    2340
aaatggccgc gatagttcac gtgaggagtt ctcatcctct tagcggcatc cccatggccc    2400
agggtgcacg ggggaattag cctctcgcgg agtcatcacg catcgactga attccctggt    2460
gaaaactgag ttagccagtt gttcctaaga tactcctgat gctgagagtg tgagcaggag    2520
gcgctgcccc atccgcaagt cagtgtcccc caccccctgc ggggtccaca gcccaggcat   2580
ctccggtcca gtgtttccca acattcgcg tgccgaattg taaaaagtgc acgttaatgc     2640
gagcctgtcg gtgtgacatg aatctcagcc atgctggttg ccatcagtca gcacggagag   2700
agaaaccttt tgtgcctaat tagcacgcag aacagaacac agggttcgat ttatggactt    2760
ttcaaaacga gaatttcagt gggagactgt ggcaaatgac acagtgttga cactggaatt   2820
ttgactacat gttggtctag agcggccgcc accgcggtgg agctccaatt cgt            2873
```

<210> SEQ ID NO 7
<211> LENGTH: 541
<212> TYPE: PRT
<213> ORGANISM: Homo sapiens

<400> SEQUENCE: 7

```
Met Ser Gly Ser Gln Asn Asn Asp Lys Arg Gln Phe Leu Leu Glu Arg
1               5                   10                  15

Leu Leu Asp Ala Val Lys Gln Cys Gln Ile Arg Phe Gly Gly Arg Lys
                20                  25                  30

Glu Ile Ala Ser Asp Ser Asp Ser Arg Val Thr Cys Leu Cys Ala Gln
            35                  40                  45

Phe Glu Ala Val Leu Gln His Gly Leu Lys Arg Ser Arg Gly Leu Ala
        50                  55                  60

Leu Thr Ala Ala Ala Ile Lys Gln Ala Ala Gly Phe Ala Ser Lys Thr
65                  70                  75                  80

Glu Thr Glu Pro Val Phe Trp Tyr Tyr Val Lys Glu Val Leu Asn Lys
                85                  90                  95

His Glu Leu Gln Arg Phe Tyr Ser Leu Arg His Ile Ala Ser Asp Val
            100                 105                 110

Gly Arg Gly Arg Ala Trp Leu Arg Cys Ala Leu Asn Glu His Ser Leu
        115                 120                 125

Glu Arg Tyr Leu His Met Leu Leu Ala Asp Arg Cys Arg Leu Ser Thr
```

```
            130                 135                 140
Phe Tyr Glu Asp Trp Ser Phe Val Met Asp Glu Arg Ser Ser Met
145                 150                 155                 160

Leu Pro Thr Met Ala Ala Gly Leu Asn Ser Ile Leu Phe Ala Ile Asn
                165                 170                 175

Ile Asp Asn Lys Asp Leu Asn Gly Gln Ser Lys Phe Ala Pro Thr Val
            180                 185                 190

Ser Asp Leu Leu Lys Glu Ser Thr Gln Asn Val Thr Ser Leu Leu Lys
        195                 200                 205

Glu Ser Thr Gln Gly Val Ser Ser Leu Phe Arg Glu Ile Thr Ala Ser
210                 215                 220

Ser Ala Val Ser Ile Leu Ile Lys Pro Glu Gln Glu Thr Asp Pro Leu
225                 230                 235                 240

Pro Val Val Ser Arg Asn Val Ser Ala Asp Ala Lys Cys Lys Lys Glu
                245                 250                 255

Arg Lys Lys Lys Lys Val Thr Asn Ile Ile Ser Phe Asp Asp Glu
            260                 265                 270

Glu Asp Glu Gln Asn Ser Gly Asp Val Phe Lys Lys Thr Pro Gly Ala
        275                 280                 285

Gly Glu Ser Ser Glu Asp Asn Ser Asp Arg Ser Ser Val Asn Ile Met
290                 295                 300

Ser Ala Phe Glu Ser Pro Phe Gly Pro Asn Ser Asn Gly Ser Gln Ser
305                 310                 315                 320

Ser Asn Ser Trp Lys Ile Asp Ser Leu Ser Leu Asn Gly Glu Phe Gly
                325                 330                 335

Tyr Gln Lys Leu Asp Val Lys Ser Ile Asp Asp Glu Asp Val Asp Glu
            340                 345                 350

Asn Glu Asp Asp Val Tyr Gly Asn Ser Ser Gly Arg Lys His Arg Gly
        355                 360                 365

His Ser Glu Ser Pro Glu Lys Pro Leu Glu Gly Asn Thr Cys Leu Ser
370                 375                 380

Gln Met His Ser Trp Ala Pro Leu Lys Val Leu His Asn Asp Ser Asp
385                 390                 395                 400

Ile Leu Phe Pro Val Ser Gly Val Gly Ser Tyr Ser Pro Ala Asp Ala
                405                 410                 415

Pro Leu Gly Ser Leu Glu Asn Gly Thr Gly Pro Glu Asp His Val Leu
            420                 425                 430

Pro Asp Pro Gly Leu Arg Tyr Ser Val Glu Ala Ser Ser Pro Gly His
        435                 440                 445

Gly Ser Pro Leu Ser Ser Leu Leu Pro Ser Ala Ser Val Pro Glu Ser
450                 455                 460

Met Thr Ile Ser Glu Leu Arg Gln Ala Thr Val Ala Met Met Asn Arg
465                 470                 475                 480

Lys Asp Glu Leu Glu Glu Asn Arg Ser Leu Arg Asn Leu Leu Asp
                485                 490                 495

Gly Glu Met Glu His Ser Ala Ala Leu Arg Gln Glu Val Asp Thr Leu
            500                 505                 510

Lys Arg Lys Val Ala Glu Gln Glu Arg Gln Gly Met Lys Val Gln
        515                 520                 525

Ala Leu Ala Ser Tyr Leu Cys Tyr Phe Val Arg Arg Phe
530                 535                 540

<210> SEQ ID NO 8
```

<211> LENGTH: 813
<212> TYPE: PRT
<213> ORGANISM: Homo sapiens

<400> SEQUENCE: 8

```
Met Ser Gly Ser Gln Asn Asn Asp Lys Arg Gln Phe Leu Leu Glu Arg
1               5                   10                  15

Leu Leu Asp Ala Val Lys Gln Cys Gln Ile Arg Phe Gly Gly Arg Lys
            20                  25                  30

Glu Ile Ala Ser Asp Ser Asp Ser Arg Val Thr Cys Leu Cys Ala Gln
        35                  40                  45

Phe Glu Ala Val Leu Gln His Gly Leu Lys Arg Ser Arg Gly Leu Ala
    50                  55                  60

Leu Thr Ala Ala Ile Lys Gln Ala Ala Gly Phe Ala Ser Lys Thr
65                  70                  75                  80

Glu Thr Glu Pro Val Phe Trp Tyr Tyr Val Lys Glu Val Leu Asn Lys
                85                  90                  95

His Glu Leu Gln Arg Phe Tyr Ser Leu Arg His Ile Ala Ser Asp Val
            100                 105                 110

Gly Arg Gly Arg Ala Trp Leu Arg Cys Ala Leu Asn Glu His Ser Leu
        115                 120                 125

Glu Arg Tyr Leu His Met Leu Leu Ala Asp Arg Cys Arg Leu Ser Thr
    130                 135                 140

Phe Tyr Glu Asp Trp Ser Phe Val Met Asp Glu Arg Ser Ser Met
145                 150                 155                 160

Leu Pro Thr Met Ala Ala Gly Leu Asn Ser Ile Leu Phe Ala Ile Asn
                165                 170                 175

Ile Asp Asn Lys Asp Leu Asn Gly Gln Ser Lys Phe Ala Pro Thr Val
            180                 185                 190

Ser Asp Leu Leu Lys Glu Ser Thr Gln Asn Val Thr Ser Leu Leu Lys
        195                 200                 205

Glu Ser Thr Gln Gly Val Ser Ser Leu Phe Arg Glu Ile Thr Ala Ser
    210                 215                 220

Ser Ala Val Ser Ile Leu Ile Lys Pro Glu Gln Glu Thr Asp Pro Leu
225                 230                 235                 240

Pro Val Val Ser Arg Asn Val Ser Ala Asp Ala Lys Cys Lys Lys Glu
                245                 250                 255

Arg Lys Lys Lys Lys Lys Val Thr Asn Ile Ile Ser Phe Asp Asp Glu
            260                 265                 270

Glu Asp Glu Gln Asn Ser Gly Asp Val Phe Lys Lys Thr Pro Gly Ala
        275                 280                 285

Gly Glu Ser Ser Glu Asp Asn Ser Asp Arg Ser Ser Val Asn Ile Met
    290                 295                 300

Ser Ala Phe Glu Ser Pro Phe Gly Pro Asn Ser Asn Gly Ser Gln Ser
305                 310                 315                 320

Ser Asn Ser Trp Lys Ile Asp Ser Leu Ser Leu Asn Gly Glu Phe Gly
                325                 330                 335

Tyr Gln Lys Leu Asp Val Lys Ser Ile Asp Glu Asp Val Asp Glu
            340                 345                 350

Asn Glu Asp Asp Val Tyr Gly Asn Ser Ser Gly Arg Lys His Arg Gly
        355                 360                 365

His Ser Glu Ser Pro Glu Lys Pro Leu Glu Gly Asn Thr Cys Leu Ser
    370                 375                 380

Gln Met His Ser Trp Ala Pro Leu Lys Val Leu His Asn Asp Ser Asp
```

-continued

```
            385                 390                 395                 400
Ile Leu Phe Pro Val Ser Gly Val Gly Ser Tyr Ser Pro Ala Asp Ala
                405                 410                 415

Pro Leu Gly Ser Leu Glu Asn Gly Thr Gly Pro Glu Asp His Val Leu
                420                 425                 430

Pro Asp Pro Gly Leu Arg Tyr Ser Val Glu Ala Ser Ser Pro Gly His
                435                 440                 445

Gly Ser Pro Leu Ser Ser Leu Leu Pro Ser Ala Ser Val Pro Glu Ser
            450                 455                 460

Met Thr Ile Ser Glu Leu Arg Gln Ala Thr Val Ala Met Met Asn Arg
465                 470                 475                 480

Lys Asp Glu Leu Glu Glu Asn Arg Ser Leu Arg Asn Leu Leu Asp
                485                 490                 495

Gly Glu Met Glu His Ser Ala Ala Leu Arg Gln Glu Val Asp Thr Leu
                500                 505                 510

Lys Arg Lys Val Ala Glu Gln Glu Arg Gln Gly Met Lys Val Gln
                515                 520                 525

Ala Leu Ala Arg Glu Asn Glu Val Leu Lys Val Gln Leu Lys Lys Tyr
            530                 535                 540

Val Gly Ala Val Gln Met Leu Lys Arg Glu Gly Gln Thr Ala Glu Val
545                 550                 555                 560

Pro Asn Leu Trp Ser Val Asp Gly Glu Val Thr Val Ala Glu Gln Lys
                565                 570                 575

Pro Gly Glu Ile Ala Glu Glu Leu Ala Ser Ser Tyr Glu Arg Lys Leu
                580                 585                 590

Ile Glu Val Ala Glu Met His Gly Glu Leu Ile Glu Phe Asn Glu Arg
                595                 600                 605

Leu His Arg Ala Leu Val Ala Lys Glu Ala Leu Val Ser Gln Met Arg
            610                 615                 620

Gln Glu Leu Ile Asp Leu Arg Gly Pro Val Pro Gly Asp Leu Ser Gln
625                 630                 635                 640

Thr Ser Glu Asp Gln Ser Leu Ser Asp Phe Glu Ile Ser Asn Arg Ala
                645                 650                 655

Leu Ile Asn Val Trp Ile Pro Ser Val Phe Leu Arg Gly Lys Ala Ala
                660                 665                 670

Asn Ala Phe His Val Tyr Gln Val Tyr Ile Arg Ile Lys Asp Asp Glu
                675                 680                 685

Trp Asn Ile Tyr Arg Arg Tyr Thr Glu Phe Arg Ser Leu His His Lys
            690                 695                 700

Leu Gln Asn Lys Tyr Pro Gln Val Arg Ala Tyr Asn Phe Pro Pro Lys
705                 710                 715                 720

Lys Ala Ile Gly Asn Lys Asp Ala Lys Phe Val Glu Glu Arg Arg Lys
                725                 730                 735

Gln Leu Gln Asn Tyr Leu Arg Ser Val Met Asn Lys Val Ile Gln Met
                740                 745                 750

Val Pro Glu Phe Ala Ala Ser Pro Lys Lys Glu Thr Leu Ile Gln Leu
                755                 760                 765

Met Pro Phe Phe Val Asp Ile Thr Pro Pro Gly Glu Pro Val Asn Ser
                770                 775                 780

Arg Pro Lys Ala Ala Ser Arg Phe Pro Lys Leu Ser Arg Gly Gln Pro
785                 790                 795                 800

Arg Glu Thr Arg Asn Val Glu Pro Gln Ser Gly Asp Leu
                805                 810
```

<210> SEQ ID NO 9
<211> LENGTH: 784
<212> TYPE: PRT
<213> ORGANISM: Homo sapiens

<400> SEQUENCE: 9

Met Ser Gly Ser Gln Asn Asn Asp Lys Arg Gln Phe Leu Leu Glu Arg
1               5                   10                  15

Leu Leu Asp Ala Val Lys Gln Cys Gln Ile Arg Phe Gly Gly Arg Lys
            20                  25                  30

Glu Ile Ala Ser Asp Ser Asp Ser Arg Val Thr Cys Leu Cys Ala Gln
        35                  40                  45

Phe Glu Ala Val Leu Gln His Gly Leu Lys Arg Ser Arg Gly Leu Ala
    50                  55                  60

Leu Thr Ala Ala Ala Ile Lys Gln Ala Ala Gly Phe Ala Ser Lys Thr
65                  70                  75                  80

Glu Thr Glu Pro Val Phe Trp Tyr Tyr Val Lys Glu Val Leu Asn Lys
                85                  90                  95

His Glu Leu Gln Arg Phe Tyr Ser Leu Arg His Ile Ala Ser Asp Val
            100                 105                 110

Gly Arg Gly Arg Ala Trp Leu Arg Cys Ala Leu Asn Glu His Ser Leu
        115                 120                 125

Glu Arg Tyr Leu His Met Leu Leu Ala Asp Arg Cys Arg Leu Ser Thr
    130                 135                 140

Phe Tyr Glu Asp Trp Ser Phe Val Met Asp Glu Arg Ser Ser Met
145                 150                 155                 160

Leu Pro Thr Met Ala Ala Gly Leu Asn Ser Ile Leu Phe Ala Ile Asn
                165                 170                 175

Ile Asp Asn Lys Asp Leu Asn Gly Gln Ser Lys Phe Ala Pro Thr Val
            180                 185                 190

Ser Asp Leu Leu Lys Glu Ser Thr Gln Asn Val Thr Ser Leu Leu Lys
        195                 200                 205

Glu Ser Thr Gln Gly Val Ser Ser Leu Phe Arg Glu Ile Thr Ala Ser
    210                 215                 220

Ser Ala Val Ser Ile Leu Ile Lys Pro Glu Gln Glu Thr Asp Pro Leu
225                 230                 235                 240

Pro Val Val Ser Arg Asn Val Ser Ala Asp Ala Lys Cys Lys Lys Glu
                245                 250                 255

Arg Lys Lys Lys Lys Lys Val Thr Asn Ile Ile Ser Phe Asp Asp Glu
            260                 265                 270

Glu Asp Glu Gln Asn Ser Gly Asp Val Phe Lys Thr Pro Gly Ala
    275                 280                 285

Gly Glu Ser Ser Glu Asp Asn Ser Asp Arg Ser Ser Val Asn Ile Met
290                 295                 300

Ser Ala Phe Glu Ser Pro Phe Gly Pro Asn Ser Asn Gly Ser Gln Ser
305                 310                 315                 320

Ser Asn Ser Trp Lys Ile Asp Ser Leu Ser Leu Asn Gly Glu Phe Gly
                325                 330                 335

Tyr Gln Lys Leu Asp Val Lys Ser Ile Asp Asp Glu Asp Val Asp Glu
            340                 345                 350

Asn Glu Asp Asp Val Tyr Gly Asn Ser Ser Gly Arg Lys His Arg Gly
        355                 360                 365

His Ser Glu Ser Pro Glu Lys Pro Leu Glu Gly Asn Thr Cys Leu Ser

```
                370             375             380
Gln Met His Ser Trp Ala Pro Leu Lys Val Leu His Asn Asp Ser Asp
385             390             395             400

Ile Leu Phe Pro Val Ser Gly Val Gly Ser Tyr Ser Pro Ala Asp Ala
            405             410             415

Pro Leu Gly Ser Leu Glu Asn Gly Thr Gly Pro Glu Asp His Val Leu
            420             425             430

Pro Asp Pro Gly Leu Arg Tyr Ser Val Glu Ala Ser Ser Pro Gly His
            435             440             445

Gly Ser Pro Leu Ser Ser Leu Leu Pro Ser Ala Ser Val Pro Glu Ser
450             455             460

Met Thr Ile Ser Glu Leu Arg Gln Ala Thr Val Ala Met Met Asn Arg
465             470             475             480

Lys Asp Glu Leu Glu Glu Asn Arg Ser Leu Arg Asn Leu Leu Asp
            485             490             495

Gly Glu Met Glu His Ser Ala Ala Leu Arg Gln Glu Val Asp Thr Leu
            500             505             510

Lys Arg Lys Val Ala Glu Gln Glu Arg Gln Gly Met Lys Val Gln
            515             520             525

Ala Leu Ala Arg Glu Asn Glu Val Leu Lys Val Gln Leu Lys Lys Tyr
            530             535             540

Val Gly Ala Val Gln Met Leu Lys Arg Glu Gly Gln Thr Ala Glu Val
545             550             555             560

Pro Asn Leu Trp Ser Val Asp Gly Glu Val Thr Val Ala Glu Gln Lys
            565             570             575

Pro Gly Glu Ile Ala Glu Glu Leu Ala Ser Ser Tyr Glu Arg Lys Leu
            580             585             590

Ile Glu Val Ala Glu Met His Gly Glu Leu Ile Glu Phe Asn Glu Arg
            595             600             605

Leu His Arg Ala Leu Val Ala Lys Glu Ala Leu Val Ser Gln Met Arg
            610             615             620

Gln Glu Leu Ile Asp Leu Arg Gly Pro Val Pro Gly Asp Leu Ser Gln
625             630             635             640

Thr Ser Glu Asp Gln Ser Leu Ser Asp Phe Glu Ile Ser Asn Arg Ala
            645             650             655

Leu Ile Asn Val Trp Ile Pro Ser Val Phe Leu Arg Gly Lys Ala Ala
            660             665             670

Asn Ala Phe His Val Tyr Gln Val Tyr Ile Arg Ile Lys Asp Asp Glu
            675             680             685

Trp Asn Ile Tyr Arg Arg Tyr Thr Glu Phe Arg Ser Leu His His Lys
            690             695             700

Leu Gln Asn Lys Tyr Pro Gln Val Arg Ala Tyr Asn Phe Pro Pro Lys
705             710             715             720

Lys Ala Ile Gly Asn Lys Asp Ala Lys Phe Val Glu Arg Arg Lys
            725             730             735

Gln Leu Gln Asn Tyr Leu Arg Ser Val Met Asn Lys Val Ile Gln Met
            740             745             750

Val Pro Glu Phe Ala Ala Ser Pro Lys Lys Glu Thr Leu Ile Gln Leu
            755             760             765

Met Pro Phe Phe Val Asp Trp Ile Ser Leu Val Trp Lys Trp Pro Arg
            770             775             780

<210> SEQ ID NO 10
```

```
<211> LENGTH: 198
<212> TYPE: DNA
<213> ORGANISM: Homo sapiens

<400> SEQUENCE: 10
ggtccgaact ccatactctt tgcgattaac attgacaaca aggatttgaa cgggcagagt     60
aagtttgctc ccaccgtttc agacctctta aaggagtcaa cgcagaatgt gaccttgctg    120
aaggagtcca cgcaaggagt gagcagcgtg ttcagggaga tcacagcctc ctctgccatc    180
tccatcctca tcaaacct                                                  198

<210> SEQ ID NO 11
<211> LENGTH: 198
<212> TYPE: DNA
<213> ORGANISM: Homo sapiens

<400> SEQUENCE: 11
ggtccgaact ccatactctt tgcgattaac attgacaaca aggatttgaa cgggcagagt     60
aagtttgctc ccaccgtttc agacctctta aaggagtcaa cgcagaatgt gaacttgctg    120
aaggagtcca cgcaaggagt gagcagcgtg ttcagggaga tcacagcctc ctctgccatc    180
tccatcctca tcaaacct                                                  198

<210> SEQ ID NO 12
<211> LENGTH: 149
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is a, c, g or t

<400> SEQUENCE: 12
acgggcagna taagtttgct cccaccgttt cagacctctt aaaggagtca acgcagaatg     60
tgaacttgct gaaggagtcc acgcaaggag tgagcagcgt gttcagggag atcacagcct    120
cctctgccat ctccatcctc atcaaacct                                      149

<210> SEQ ID NO 13
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: residue 1 is modified with acetyl
<220> FEATURE:
<221> NAME/KEY: misc_feature
<222> LOCATION: (4)..(4)
<223> OTHER INFORMATION: residue 4 is modified with a-(4-methyl-
      coumaryl-7-amide)

<400> SEQUENCE: 13

Asp Glu Val Asp
1

<210> SEQ ID NO 14
<211> LENGTH: 4
<212> TYPE: PRT
<213> ORGANISM: Artificial
<220> FEATURE:
<223> OTHER INFORMATION: synthetic
<220> FEATURE:
<221> NAME/KEY: misc_feature
```

```
-continued

<222> LOCATION: (1)..(1)
<223> OTHER INFORMATION: residue 1 is modified with methyl ketone Ac
<220> FEATURE:
<221> NAME/KEY: misc_feature
<222> LOCATION: (4)..(4)
<223> OTHER INFORMATION: residue 4 is modified with CH2OC
      (O)-[2,6-(CF3)2]

<400> SEQUENCE: 14

Tyr Val Ala Asp
1
```

IREN PROTEIN, ITS PREPARATION AND USE

FIELD OF THE INVENTION

The present invention relates to DNA sequences encoding a TNF receptor associated factor (TRAF) binding protein. More specifically, it relates to cDNA sequences encoding a biologically active protein herein designated IREN and its isoforms capable of binding to TRAF2. The invention also relates to the proteins encoded by the above DNAs, and the use of said proteins and DNA sequences in the treatment or prevention of pathological conditions associated with NF-κB induction, or with any other activity mediated by TRAF2, or with other molecules to which said protein binds.

BACKGROUND OF THE INVENTION

The Tumor Necrosis Factor/Nerve Growth Factor (TNF/NGF) receptor superfamily represents a growing family with over 20 members identified so far in mammalian cells. Although the receptors of this superfamily differ in the primary sequence of their extracellular domains, the TNF/NGF receptor superfamily members share cysteine rich subdomains that are thought to adopt generally similar tertiary folds. (Bazan, 1993; Beutler and van Huffel, 1994; Smith et al., 1994). Except for two receptors, the p55 TNF receptor and Fas/APO1, the various members of this receptor family may have varying structural differences. Nevertheless, there is much similarity of function between the receptors, indicating that they share common signaling pathways. One example for this similarity is the ability of several receptors of the TNF/NGF family to activate the transcription factor NF-κB (see hereinbelow).

TRAF2 is a member of a recently described family of proteins designated TRAF (TNF Receptor Associated Factor) that includes several proteins identified as, for example, TRAF1, TRAF2 (Rothe, M., et al (1994); PCT published application WO 95/33051), TRAF3 (Cheng, G. et al. (1995), TRAF4 (CART1, C-rich motif associated with RING and TRAF domains, Regnier et al. 1995), TRAF5 (Ishida et al. 1996a, Nakano et al. 1996) and TRAF6 (see Cao et al. 1996a, Ishida et al. 1996b). All proteins belonging to the TRAF family share a high degree of amino acid identity in their C-terminal domains, while their N-terminal domains may be unrelated. As shown in a schematic illustration of TRAF2 (FIG. 1 herein), the molecule contains a ring finger motif and two TFIIIA-like zinc finger motifs at its N-terminal end. The C-terminal half of the molecule includes a region known as the "TRAF domain" containing a potential leucine zipper region extending between amino acids 264-358 (called N-TRAF). An additional domain towards the carboxy end of the molecule between amino acids 359-501 (called C-TRAF) is responsible for TRAF binding to the receptors and to other TRAF molecules to form homo- or heterodimers.

Recruitment of TRAF adapter proteins to the cytoplasmic domains of receptor molecules can lead to the assembly of larger signaling complexes that consist of distinct TRAF adapter molecules and other effector proteins with enzymatic functions. Numerous reports have examined the activation of intracellular kinases in response to TRAF-dependent signal transduction. In particular, kinases of the mitogen-activated protein kinase (MAPK) family have been shown to be key players for signaling pathways that are triggered by TRAF-containing complexes. These pathways appear to culminate in c-Jun amino-(N)-terminal kinase (JNK) activation (Reinhard et al. 1997; Song et al. 1997). TRAF proteins can thus serve to modulate the ability of receptors to trigger distinct signaling pathways that lead to phosphorylation and activation of protein kinases and, subsequently, to the activation of transcription factors of the Rel and AP-1 family.

The c-Jun transcription factor is phosphorylated at its amino terminus by JNK, the most downstream member of one MAPK signaling pathway (Hibi et al. 1993). To be activated JNK needs to be phosphorylated by a MAPK kinase (MAPKK, SEK, MEK).

This kinase itself is phosphorylated by a MAPKKK (MEKK1), which can be activated through phosphorylation by GCKR (germinal center kinase related) protein, the most upstream kinase described in this pathway (Minden et al. 1994; Lin et al. 1995; Shi and Kehrl 1997). Dominant-negative mutants of either of these proteins that lack kinase activity block TRAF-mediated JNK activation that is induced by members of the TNF/NGFR superfamily. Thus, TRAF proteins appear to regulate the JNK activation pathway at a very proximal step (Liu et al. 1996; Lee et al. 1997; Reinhard et al. 1997). Cells from TRAF2-deficient mice failed to activate JNK in response to TNFα (Yeh et al. 1997). JNK has been demonstrated to mediate the integration of a co-stimulatory signal by CD28 during activation of T lymphocytes (Su et al. 1994). Taken together, these results suggest that co-stimulation by CD28 and TRAF-mediated co-stimulation, after ligation of TNFR-related molecules, utilize the same distal signaling components.

TRAF proteins also appear to play an important role in modulating an early step in receptor-induced activation of NF-κB (Rothe et al. 1995b; Cao et al. 1996; Nakano et al. 1996). NF-κB comprises members of a family of dimer-forming proteins with homology to the Rel oncogene which, in their dimeric form, act as transcription factors. These factors are ubiquitous and participate in regulation of the expression of multiple genes. Although initially identified as a factor that is constitutively present in B cells at the stage of Igκ light chain expression, NF-κB is known primarily for its action as an inducible transcriptional activator. In most known cases NF-κB behaves as a primary factor, namely the induction of its activity is by activation of pre-existing molecules present in the cell in their inactive form, rather than its de-novo synthesis which in turn relies on inducible transcription factors that turn-on the NF-κB gene. The effects of NF-κB are highly pleiotropic. Most of these numerous effects share the common features of being quickly induced in response to an extracellular stimulus. The majority of the NF-κB-activating agents are inducers of immune defense, including components of viruses and bacteria, cytokines that regulate immune response, UV light and others. Accordingly, many of the genes regulated by NF-κB contribute to immune defense (see Blank et al., 1992; Grilli et al., 1993; Baeuerle and Henkel, 1994, for reviews).

One major feature of NF-κB-regulation is that this factor can be found in a cytoplasmic non-DNA binding form which can be induced to translocate to the nucleus, bind DNA and activate transcription. This dual form of the NF-κB proteins is regulated by I-κB—a family of proteins that contain repeats of a domain that was initially identified in the erythrocyte protein ankyrin (Gilmore and Morin, 1993). In the unstimulated form, the NF-κB dimer occurs in association with an I-κB molecule which imposes its cytoplasmic localization preventing its interaction with the NF-κB-binding DNA sequence, and activation of transcription. The dissociation of I-κB from the NF-κB dimer constitutes its critical activation step by many of its inducing agents (DiDonato et al., 1995). There is so far little understanding of the way in which cell specificity is determined in terms of responsiveness to the various NF-κB-inducing agents.

Evidence that TRAF proteins can influence receptor-mediated activation of NF-κB came from the demonstration that dominant-negative forms of TRAF2 can inhibit NF-κB activation in response to oligomerization of several TNFR-related molecules, including TNFRII, CD40, CD30, 4-1BB, and Ox40 (Rothe et al. 1994, 1995b; Duckett et al. 1997; Arch and Thompson 1998). However, gene elimination studies in mice have failed to implicate a required role for a specific TRAF in NF-κB activation by any of these receptors (Lee et al. 1997; Yeh et al. 1997). This suggests that receptor engagement may activate NF-κB by more than one pathway.

One of the most potent inducing agents of NF-κB is the cytokine tumor necrosis factor (TNF). There are two different TNF receptors: the p55 and p75 receptors. Their expression levels vary independently among different cells (Vandenabeele et al., 1995). The p75 receptor responds preferentially to the cell-bound form of TNF (TNF is expressed both as a type II-transmembrane protein and as a soluble protein) while the p55 receptor responds just as effectively to soluble TNF molecules (Grell et al., 1995). The intracellular domains of the two receptors are structurally unrelated and bind different cytoplasmic proteins. Nevertheless, at least part of the effects of TNF, including the cytocidal effect of TNF and the induction of NF-κB, can be induced by both receptors. This feature is cell specific. The p55 receptor is capable of inducing a cytocidal effect or activation of NF-κB in all cells that exhibit such effects in response to TNF. The p75-R can have such effects only in some cells. Others, although expressing the p75-R at high levels, show induction of the effects only in response to stimulation of the p55-R (Vandenabeele et al., 1995). Apart from the TNF receptors, various other receptors of the TNF/NGF receptor family: CD30 (McDonald et al., 1995), CD40 (Berberich et al., 1994; Lalmanach-Girard et al., 1993), the lymphotoxin beta receptor and, in a few types of cells, Fas/APO1 (Rensing-Ehl et al., 1995) are also capable of inducing activation of NF-κB. The IL-1 type-I receptor, also effectively triggering NF-κB activation, shares most of the effects of the TNF receptors despite the fact that it has no structural similarity to them. Novel receptor subunits of the IL-18 receptor complex have been recently cloned and shown to trigger NF-κB translocation and activation in response to IL-18 (Born et al. 1998). The IL-1Rrp as well as a novel protein of the IL-1 receptor family, designated AcPL (Accessory Protein Like) are both required for IL-18 signaling.

The activation of NF-κB upon triggering of these various receptors results from induced phosphorylation of its associated I-κB molecules. Several components of a specific signal transduction cascade, activated in response to the proinflammatory cytokines TNF-α or IL-1β, have recently been identified. A novel protein kinase designated NIK for NF-κB Inducing Kinase was the first to be identified (see co-pending co-owned Patent Application WO 97/37016, Malinin et al. 1996). NIK was found to bind to TRAF2 and to stimulate NF-κB activation. NIK shares sequence similarity with MAP3K kinases and participates in the NF-κB inducing signaling cascade common to receptors of the TNF/NGF family and to the IL-1 type 1 receptor. TNF-α and IL-1β, initiate a signaling cascade leading to activation of two IκB kinases, IKK-1 [IKK-α] and IKK-2 [IKK-β], which phosphorylate IκB at specific N-terminal serine residues [S32 and S36 for IκBα S19 and S23 for IκBβ] (for review see Mercurio F and Manning A M, 1999). These kinases were identified as the components of a high molecular weight protein complex designated the IKK signalsome.

Phosphorylated IκB is selectively ubiquitinated by an E3 ubiquitin ligase, the terminal member of a cascade of ubiquitin conjugating enzymes. In the last step of this signaling cascade, phosphorylated and ubiquitinated IκB, which is still associated with NF-κB in the cytoplasm, is selectively degraded by the 26S proteasome. This process exposes the NLS, therefore freeing NF-κB to interact with the nuclear import machinery and translocate to the nucleus, where it binds its target genes to initiate transcription.

The identification of several additional components of the IKK signalsome has given a clue to the potential mechanisms by which receptor activation might be linked to IKK activation. One of these is an NF-κB essential modulator designated NEMO. This murine protein was found to be essential for the activation of NF-κB in a flat cellular variant of HTLV-1 Tax transformed fibroblasts which is unresponsive to all tested NF-κB stimuli (Yamaoka et al. 1998). NEMO was shown to homodimerize and to directly interact with IKK2. The same protein was independently cloned by Kovalenko et al. (see co-pending co-owned Israel Patent Application Nos. 123758 and 126024) as a RIP-binding protein and designated RAP-2. NEMO was later independently cloned by two other groups as a non-kinase component of the IKK signalsome and designated IKKAP-1 (Mercurio F et al 1999b, Rothwarf D M et al 1998). The same protein was also cloned as an E3 interacting protein, which is an adenoviral protein, encoded by the early transcription region and functions to inhibit the cytolytic effects of TNF and was shown to interact with RIP kinase (Li Y et al 1998). These studies provide evidence that NEMO mediates an essential step of the NF-κB signal transduction pathway. Three receptor-associated proteins appear to take part in initiation of the phosphorylation cascade (see diagrammatic illustration in FIG. 2). TRAF2, which when expressed at high levels can by itself trigger NF-κB activation, binds to activated p75 TNF-R (Rothe et al., 1994), lymphotoxin beta receptor (Mosialos et al., 1995), CD40 (Rothe et al., 1995a) and CD-30 (unpublished data) and mediates the induction of NF-κB by them. TRAF2 does not bind to the p55 TNF receptor nor to Fas/APO1, however, it can bind to the p55 receptor-associated protein called TRADD and TRADD has the ability to bind to a Fas/APO1-associated protein called MORT1 (or FADD—see Boldin et al. 1995b and 1996). Another death domain containing serine/threonine kinase receptor-interacting protein, designated RIP (see Stanger et al., 1995) is also capable of interacting with TRAF2 as well as with FAS/APO1, TRADD, the p55 TNF receptor and MORT-1. Thus, while RIP was initially associated with cell cytotoxicity induction (cell death), its ability to interact with TRAF2 also implicates it in NF-κB activation.

TRAF molecules appear to be involved in the pathway leading to NF-κB activation. These associations apparently allow the p55 TNF receptor and Fas/APO1 to trigger NF-κB activation (Hsu et al., 1995; Boldin et al., 1995; Chinnaiyan et al., 1995; Varfolomeev et al., 1996; Hsu et al., 1996). The triggering of NF-κB activation by the IL-1 receptor occurs independently of TRAF2 and may involve a TRAF2 homologue—TRAF6 and a recently-cloned IL-1 receptor-associated protein-kinase called IRAK (Croston et al., 1995). TRAF6 and IRAK have been also shown to play an important role in IL-18-induced signaling and function (Kanarakaraj et al. 1999).

The signaling cascades that are initiated by receptor recruitment of either TRAF molecules or death domain containing adapter proteins are regulated by proteins that can interfere with specific steps by modifying the composition of the multiprotein complexes and/or by blocking protein-protein interactions and downstream effector functions. Several cytoplasmic molecules that bind to TRAFs have been identified. Among them A20, c-IAPs (cellular Inhibitors of Apoptosis), TRIP (TRAF interacting protein) and I-TRAF/TANK (TRAF interacting protein, TRAF family members-associated NF-κB activator). (Rothe et al., 1994; Rothe et al., 1995b; Cheng and Baltimore 1996; Lee et al. 1997; Roy et al. 1997) and two others, one of which is designated clone 9, which shows some sequence homology to the proteins of the present invention, and another designated clone 15 (see co-pending co-owned Patent Application WO 97/37016). Each of these proteins has been shown to be capable at least of binding, and some also of interacting with members of the TRAF family. Yet, the functional roles of these interactions have been demonstrated to be quite distinct. These proteins may be an important link in the ability of TRAF-dependent signal transduction to modulate cell survival. In fact it is not yet clear how TRAFs, trigger the phosphorylation of I-κB. There is also no information yet as to the mechanisms that dictate cell-specific pattern of activation of TRAFs by different receptors, such as observed for the induction of NF-κB by the two TNF receptors. The crystal structure of the TRAF domain of human TRAF has been recently solved (Park, Y. C. et al. 1999). The structure reveals a trimeric self-association of the TRAF domain, which provides an avidity-based explanation for the dependence of TRAF recruitment on the oligomerization of the receptors by their trimeric extracellular ligands.

Accordingly, as regards NF-κB activation and its importance in maintaining cell viability, the various intracellular pathways involved in this activation have heretofore not been clearly elucidated, for example, how the various TRAF proteins, are involved directly or indirectly.

Furthermore, as is now known regarding various members of the TNF/NGF receptor family and their associated intracellular signaling pathways inclusive of various adapter, mediator/modulator proteins (see brief reviews and references in, for example, co-pending co-owned Israel Patent Application Nos. 114615, 114986, 115319, 116588), TNF and the FAS/APO1 ligand, for example, can have both beneficial and deleterious effects on cells. TNF, for example, contributes to the defense of the organism against tumors and infectious agents and contributes to recovery from injury by inducing the killing of tumor cells and virus-infected cells, augmenting antibacterial activities of granulocytes, and thus in these cases the TNF-induced cell killing is desirable. However, excess TNF can be deleterious and as such TNF is known to play a major pathogenic role in a number of diseases such as septic shock, anorexia, rheumatic diseases, inflammation and graft-vs-host reactions. In such cases TNF-induced cell killing is not desirable. The FAS/APO1 ligand, for example, also has desirable and deleterious effects. This FAS/APO1 ligand induces via its receptor the killing of autoreactive T cells during maturation of T cells, i.e. the killing of T cells which recognize self-antigens, during their development and thereby preventing autoimmune diseases. Further, various malignant cells and HIV-infected cells carry the FAS/APO1 receptor on their surface and can thus be destroyed by activation of this receptor by its ligand or by antibodies specific thereto, and thereby activation of cell death (apoptosis) intracellular pathways mediated by this receptor. However, the FAS/APO1 receptor may mediate deleterious effects, for example, uncontrolled killing of tissue which is observed in certain diseases such as acute hepatitis that is accompanied by the destruction of liver cells.

In view of the above, i.e. that receptors of the TNF/NGF family can induce cell death pathways on the one hand and can induce cell survival pathways (via NF-κB induction) on the other hand, there apparently exists a fine balance, intracellularly between these two opposing pathways. For example, when it is desired to achieve maximal destruction of cancer cells or other infected or diseased cells, it would be desired to have TNF and/or the FAS/APO1 ligand inducing only the cell death pathway without inducing NF-κB. Conversely, when it is desired to protect cells such as in, for example, inflammation, graft-vs-host reactions, acute hepatitis, it would be desirable to block the cell killing induction of TNF and/or FAS/APO1 ligand and enhance, instead, their induction of NF-κB. Likewise, in certain pathological circumstances it would be desirable to block the intracellular signaling pathways mediated by the p75 TNF receptor and the IL-1 receptor, while in others it would be desirable to enhance these intracellular pathways.

SUMMARY OF THE INVENTION

It is an object of the present invention to provide a biologically active protein, isoforms, analogs, fragments or derivatives thereof capable of binding to the tumor necrosis factor receptor-associated factor (TRAF) proteins. As the TRAF binding proteins are involved in the modulation or mediation of the activation of the transcription factor NF-κB, which is initiated by some of the TNF/NGF receptors, as well as others as noted above, the protein according to the present invention by binding to TRAF proteins may therefore be capable of modulating or mediating the intracellular signaling processes initiated by various ligands binding to their receptors. Such ligands are e.g. TNF, CD40 ligand, FAS ligand and others and modulation/mediation may be e.g. NF-κB activation, via interaction directly or indirectly with TRAF protein (e.g. induction of NF-κB activation by TRAF2 and TRAF6 and inhibition of NF-κB activation, by TRAF3).

The biologically active protein of the invention and its isoforms, analogs, fragments or derivatives may likewise be indirect modulators/mediators of the intracellular biological activity of a variety of other proteins which are capable of interacting with TRAF proteins directly or indirectly (e.g. FAS/APO1 receptor, p55 TNF receptor, p75 TNF receptor, IL-1 receptor and their associated proteins, such as, for example, MORT-1, TRADD, RIP).

Another object of the invention is to provide antagonists (e.g. antibodies, peptides, organic compounds, or even some isoforms) to the above novel TRAF-binding protein, isoforms, analogs, fragments and derivatives thereof, which may be used to inhibit the signaling process, or, more specifically, to inhibit the activation of NF-κB and its associated involvement in cell-survival processes, when desired. Likewise, when the TRAF-binding protein of the invention or the TRAF protein to which they bind (e.g. TRAF3) are themselves inhibitory for NF-κB activation (either directly, or through modulation of the trafficking or stability of the proteins to which they bind), then it is an object to provide antagonists to the TRAF-binding protein to activate the signaling process or more specifically, to block the inhibition of NF-κB activation and hence bring about enhanced NF-κB activation, when desired.

A further object of the invention is to use the above novel TRAF-binding protein, isoforms, analogs, fragments and derivatives thereof, to isolate and characterize additional proteins or factors, which may be involved in regulation of TRAF protein activity and/or the above noted receptor activity, e.g. other proteins which may bind to TRAF proteins and influence their activity, and/or to isolate and identify other receptors or other cellular proteins further upstream or downstream in the signaling process(es) to which these novel proteins, analogs, fragments and derivatives bind, and hence, in whose function they are also involved.

A still further object of the invention is to provide inhibitors which can be introduced into cells to bind or interact with the novel TRAF-binding protein and possible isoforms thereof, which inhibitors may act to inhibit TRAF protein-associated activity in, for example, NF-κB activation and hence, when desired, to inhibit NF-κB activation; or which may act to inhibit inhibitory TRAF-associated activity (e.g. TRAF3) in NF-κB activation and hence, when desired, to enhance NF-κB activation.

Moreover, it is an object of the present invention to use the above-mentioned TRAF-binding protein, isoforms and analogs, fragments and derivatives as antigens for the preparation of polyclonal and/or monoclonal antibodies thereto. The antibodies, in turn, may be used, for example, for the purification of the new proteins from different sources, such as cell extracts or transformed cell lines.

Furthermore, these antibodies may be used for diagnostic purposes, e.g. for identifying disorders related to abnormal functioning of cellular effects mediated directly by TRAF proteins or mediated by the p55 TNF receptor, FAS/APO1 receptor, or other related receptors and their associated cellular proteins (e.g. MORT-1, TRADD, RIP), which act directly or indirectly to modulate/mediate intracellular processes via interaction with TRAF proteins.

A further object of the invention is to provide pharmaceutical compositions comprising the above novel IREN protein, isoforms, or analogs, fragments or derivatives, as well as pharmaceutical compositions comprising the above noted antibodies or other antagonists.

The present invention thus provides a novel IREN protein binding to at least TRAF2 and having a high specificity of binding to TRAF2. Hence is a modulator or mediator of TRAF2 intracellular activity. TRAF2 is involved in the modulation or mediation of at least one intracellular signaling pathway being the cell survival- or viability-related pathway in which TRAF2 is directly involved in activation of NF-κB which plays a central role in cell survival.

In fact, this protein, designated IREN (for IκB REgulator) binds to TRAF2 and apparently acts in the NF-κB signalling pathway downstream to NIK but upstream to NEMO and IKK1 and enhances IKK1 phosphorylation of IκB. Further, TRAF2 by being capable of interaction directly or indirectly with the above noted p55 TNF receptor, p75 TNF receptor, FAS/APO1 receptors and their associated proteins MORT-1. TRADD and RIP, also is a mediator or modulator of the NF-κB induction or activation activity attributed to these receptors. TRAF2 is therefore a modulator/mediator of the cell survival pathways (as opposed to the cell death pathways) mediated by these receptors and their associated proteins and as such the extent of interaction between these receptors and/or proteins with TRAF2 is an important factor in the outcome of the activity of these receptors (once activated by their ligands), namely, whether the cells will survive or die. Accordingly, the proteins of the invention, play a key role in this interaction between TRAF2 and the other proteins/receptors with which TRAF2 interacts, as proteins such as IREN by binding specifically to TRAF2 will modulate its activity and/or will have their activity modulated by interaction with TRAF2.

As will be used herein throughout, TRAF protein activity, for example TRAF2 activity, is meant to include its activity in modulation/mediation in the cell survival pathway, such as NF-κB induction/activation. Likewise, as used herein throughout TRAF-binding protein, in particular TRAF2-binding protein, activity is meant to include modulation/mediation of TRAFs, in particular, TRAF2 activity by virtue of specific binding to TRAFs, especially TRAF2 proteins, this modulation/mediation including modulation/mediation of cell survival pathways, in particular, those relating to NF-κB activation/induction in which TRAF proteins, especially TRAF2 is involved directly or indirectly. Thus IREN may be considered as an indirect modulator/mediators of all the above mentioned proteins and possibly a number of others which are involved in cell survival, such as NF-κB activation/induction and to which TRAF2 (or other TRAF proteins) binds, or with which TRAF2 (or other TRAF proteins) interacts in a direct or indirect fashion. Likewise TRAF2 is involved in the regulation of AP1 transcription factor through activation of the Jun kinase cascade and thus IREN may have a role in the Jun kinase activation pathway or in the control of other gene activation pathways e.g.—the p38 kinase pathway. It thus may have an important role in the control of inflammation and other non-apoptotic effects of TNF as well as in the control of apoptosis.

More specifically, the present invention provides a DNA sequence encoding a protein capable of binding to TRAF selected from:
(a) a cDNA sequence of the herein designated IREN comprising the nucleotide sequence depicted in FIG. 3;
(b) a cDNA sequence of the herein designated isoform IREN-10B comprising the nucleotide sequence depicted in FIG. 4;
(c) a cDNA sequence of the herein designated isoform IREN-E comprising the nucleotide sequence depicted in FIG. 5;
(d) a fragment of a sequence (a)-(c) which encodes a biologically active protein capable of binding to at least the residues 225-501 of the amino acid sequence of TRAF2;
(e) A DNA sequence capable of hybridization to a sequence of (a)-(d) under moderately stringent conditions and which encodes a biologically active protein capable of binding to at least the residues 225-501 of the amino acid sequence of TRAF2; and
(f) A DNA sequence, which is degenerate as a result of the genetic code to the DNA sequences, defined in (a)-(e) and which encodes a biologically active protein capable of binding to at least the residues 225-501 of the amino acid sequence of TRAF2.

Embodiments of the above DNA sequence of the invention encoding the protein encoded by IREN include:
(i) A DNA sequence encoding the protein IREN, its biologically active isoforms, fragments or analogs thereof, capable of binding to TRAF2 and capable of modulating the activity of NF-κB and IREN isoforms, fragments or analogs thereof;
(ii) A DNA sequence as in (i) above, selected from the group consisting of:
a) A cDNA sequence derived from the coding region of a native IREN protein;
b) DNA sequences capable of hybridization to a sequence of (a) under moderately stringent conditions and which encode a biologically active IREN; and
c) DNA sequences, which are degenerate as a result of the genetic code to the sequences, defined in (a) and (b) and which encode a biologically active IREN protein;
(iii) A DNA sequence as in (i) or (ii) above comprising at least part of the sequence depicted in FIG. 3 and encoding at least one active IREN protein, isoform, analog or fragment;
(iv) A DNA sequence as in (iii) above encoding an IREN protein, isoform, analog, or fragment having at least part of the amino acid sequence depicted in FIG. 3.

In another aspect, the invention provides proteins or polypeptides encoded by the above noted DNA, provided that they are capable of binding to TRAF2, preferably to at least the 225-501 amino acid sequence of TRAF2 and the isoforms, analogs, fragments and derivatives of said protein and polypeptides. Embodiments of these proteins/polypeptides, according to the invention include:
  (a) A protein being the protein herein designated IREN;
  (b) Isoforms, fragments, analogs and derivatives thereof; and
  (c) An IREN protein, isoforms, analogs, fragments and derivatives thereof having at least part of the amino acid sequence depicted in FIG. 6.

In yet another aspect, the invention provides a vector comprising any of the above DNA sequences according to the invention which are capable of being expressed in host cells selected from prokaryotic and eukaryotic cells; as well as transformed prokaryotic and eukaryotic cells containing said vector.

The invention also provides a method for producing a protein, isoform, analog, fragment or derivative encoded by any of the above DNA sequences according to the invention which comprises growing the above mentioned transformed host cells under conditions suitable for the expression of said protein, isoforms, analogs, fragments or derivatives, effecting post-translational modification, as necessary, for obtaining said protein, isoform, analogs, fragments or derivatives and isolating said expressed protein, isoforms, analogs, fragments or derivatives.

In a further aspect, the invention provides antibodies or active fragments or derivatives thereof, specific for the above TRAF-binding proteins, analogs, isoforms, fragments or derivatives thereof or specific for the IREN protein, isoform, analog, fragment or derivative thereof noted above.

In a different aspect, the invention provides the following screening methods:

(i) A method for screening of a ligand capable of binding to a protein according to the invention, as noted above, including isoforms, analogs, fragments or derivatives thereof, comprising contacting an affinity chromatography matrix to which said protein, isoform, analog, fragment or derivative is attached with a cell extract whereby the ligand is bound to said matrix, and eluting, isolating and analyzing said ligand.

(ii) A method for screening of a DNA sequence coding for a ligand capable of binding to a protein, isoform, analog, fragment or derivative according to the invention as noted above, comprising applying the yeast two-hybrid procedure in which a sequence encoding said protein, isoform analog, derivative or fragment is carried by one hybrid vector and sequences from a cDNA or genomic DNA library are carried by the second hybrid vector, transforming yeast host cells with said vectors, isolating the positively transformed cells, and extracting said second hybrid vector to obtain a sequence encoding said ligand.

Similarly, there is also provided a method for isolating and identifying proteins, isoforms, analogs, fragments according to the invention noted above, capable of binding directly to TRAF2, comprising applying the yeast two-hybrid procedure in which a sequence encoding said TRAF2 is carried by one hybrid vector and sequence from a cDNA or genomic DNA library is carried by the second hybrid vector, the vectors then being used to transform yeast host cells and the positive transformed cells being isolated, followed by extraction of the said second hybrid vector to obtain a sequence encoding a protein which binds to said TRAF2.

In yet another aspect of the invention there is provided a method for the modulation or mediation in cells of the activity of NF-κB or any other intracellular signaling activity modulated or mediated by TRAF2 or by other molecules to which a protein, isoform, analog, fragment or derivative thereof of the invention as noted above, said method comprising treating said cells by introducing into said cells one or more of said protein, isoform, analog, fragment or derivative thereof in a form suitable for intracellular introduction thereof, or introducing into said cells a DNA sequence encoding said one or more protein, isoform, analog, fragment or derivative thereof in the form of a suitable vector carrying said sequence, said vector being capable of effecting the insertion of said sequence into said cells in a way that said sequence is expressed in said cells.

Embodiments of this above method for modulation/mediation in cells of the activity of NF-κB or any other intracellular signaling activity modulated or mediated by TRAF2 or other molecules include:

(i) A method as above, wherein said treating of cells comprises introducing into said cells a DNA sequence encoding said IREN protein, isoform, fragment, analog or derivative in the form of a suitable vector carrying said sequence, said vector being capable of effecting the insertion of said sequence into said cells in a way that said sequence is expressed in said cells.

(ii) A method as above wherein said treating of said cells is by transfection of said cells with a recombinant animal virus vector comprising the steps of:
    (a) constructing a recombinant animal virus vector carrying a sequence encoding a viral surface protein (ligand) that is capable of binding to a specific cell surface receptor on the surface of said cells to be treated and a second sequence encoding said IREN protein isoforms, analogs, fragments and derivatives according to the invention, that when expressed in said cells is capable of modulating/mediating the activity of NF-κB or any other intracellular signaling activity modulated/mediated by TRAF2 or other said molecules; and
    (b) infecting said cells with said vector of (a).

Likewise, the present invention also provides a method for modulating TRAF2 modulated/mediated effect on cells comprising treating said cells with the antibodies or active fragments or derivatives thereof, according to the invention as noted above, said treating being by application of a suitable composition containing said antibodies, active fragments or derivatives thereof to said cells, wherein when the IREN protein or portions thereof of said cells are exposed on the extracellular surface, said composition is formulated for extracellular application, and when said IREN protein is intracellular said composition is formulated for intracellular application.

Other methods of the invention for modulating the TRAF2 modulated/mediated effect on cells include:

(i) A method comprising treating said cells with an oligonucleotide sequence encoding an antisense sequence for at least part of the DNA sequence encoding said IREN protein, this DNA sequence being any of the above mentioned ones of the invention, said oligonucleotide sequence being capable of blocking the expression of said IREN protein.

(ii) A method as in (i) above wherein said oligonucleotide sequence is introduced to said cells via a recombinant virus as noted above, wherein said second sequence of said virus encodes said oligonucleotide sequence.

(iii) A method comprising applying the ribozyme procedure in which a vector encoding a ribozyme sequence capable of interacting with a cellular mRNA sequence encoding said IREN protein, isoform, analog, fragment or derivative of the invention noted above, is introduced into said cells in a form that permits expression of said ribozyme sequence in said cells, and wherein when said ribozyme sequence is expressed in said cells it interacts with said cellular mRNA sequence and cleaves said mRNA sequence resulting in the inhibition of expression of said IREN protein in said cells.

In the above methods and embodiments thereof of the invention there is included also a method for the prevention or treatment of a pathological condition associated with NF-κB induction or with any other activity mediated by TRAF2 or by other molecules to which a protein, isoform, analog, fragment or derivative, according to the invention, binds, said method comprising administering to a patient in need an effective amount of a protein, isoform, analog, fragment or derivative, according to the invention, or a DNA molecule coding therefor, or a molecule capable of disrupting the interaction of said protein, isoform, analog, fragment or derivative, with TRAF2 or any other molecule to which said protein, isoform, analog, fragment or derivative binds. In this method of the invention, said protein of the invention administered to the patient in need can be specifically the protein encoded by IREN, or a DNA molecule coding therefor. The protein encoded by IREN is believed at present to modulate NF-κB induction by IKK-1 and NIK. In an additional aspect of the invention there is provided a pharmaceutical composition for the modulation of the TRAF2 modulated/mediated effect on cells comprising, as active ingredient IREN its biologically active fragments, analogs, derivatives or mixtures thereof.

Other pharmaceutical compositions or embodiments thereof according to the invention include:

(i) A pharmaceutical composition for modulating the TRAF2 modulated/mediated effect on cells comprising, as active ingredient, a recombinant animal virus vector encoding a protein capable of binding a cell surface receptor and IREN, its biologically active isoforms, active fragments or analogs, according to the invention.

(ii) A pharmaceutical composition for modulating the TRAF2 modulated/mediated effect on cells comprising as active ingredient, an oligonucleotide sequence encoding an anti-sense sequence of the IREN mRNA sequence according to the invention.

A further embodiment of the above pharmaceutical composition is specifically a pharmaceutical composition for the prevention or treatment of a pathological condition associated with NF-κB induction or with any other activity mediated by TRAF2 or by other molecules to which a protein, analog, isoform, fragment or derivative, according to the invention binds, said composition comprising an effective amount of a protein, analog, isoform, fragment or derivative, according to the invention or a DNA molecule coding therefor, or a molecule capable of disrupting the interaction of said protein, analog, isoform, fragment or derivative, with TRAF2 or any other molecule to which said protein, analog, isoform, fragment or derivative, binds. In a yet further specific embodiment said pharmaceutical composition comprising an effective amount of the protein encoded by IREN, an isoform, analog, derivative or fragment of IREN, or a DNA molecule coding therefor.

In yet another specific embodiment, the invention provides a pharmaceutical composition for the prevention or treatment of a pathological condition associated with NF-κB induction or with any other activity mediated by TRAF2 or by other molecules to which the protein IREN binds, said composition comprising a molecule capable of interfering with the activity of IREN. In this composition, the interfering molecule may be an effective amount of IREN mutated in active site residues, this mutated IREN serving to interfere with native IREN.

One known condition associated with NF-κB induction (abnormal) is AIDS, others are e.g. autoimmune diseases, as well as tumors.

Still further aspects and embodiments of the invention are:

(i) A method for identifying and producing a ligand capable of modulating the cellular activity modulated/mediated by a protein, isoform, analog, fragment or derivative, according to the invention, comprising:
  a) Screening for a ligand capable of binding to a polypeptide comprising at least a portion of the IREN sequence depicted in FIG. 6.
  b) Identifying and characterizing a ligand, other than TRAF2 or portions of a receptor of the TNF/NGF receptor family, found by said screening step to be capable of said binding; and
  c) Producing said ligand in substantially isolated and purified form.

(ii) A method for identifying and producing a ligand capable of modulating the cellular activity modulated/mediated by IREN comprising:
  a) Screening for a ligand capable of binding to a polypeptide comprising at least a portion of the IREN sequence depicted in FIG. 6.
  b) Identifying and characterizing a ligand, other than TRAF2 or portions of a receptor of the TNF/NGF receptor family, found by said screening step to be capable of said binding; and
  c) Producing said ligand in substantially isolated and purified form.

(iii) A method for identifying and producing a ligand capable of directly or indirectly modulating the cellular activity modulated/mediated by IREN comprising:
  a) Screening for a molecule capable of modulating activities modulated/mediated by IREN;
  b) Identifying and characterizing said molecule; and
  c) Producing said molecule in substantially isolated and purified form.

(iv) A method for identifying and producing a molecule capable of directly or indirectly modulating the cellular activity modulated/mediated by a protein, isoform, analog, fragment or derivative of the invention, comprising:
  a) Screening for a molecule capable of modulating activities modulated/mediated by an IREN protein, isoform, analog, fragment or derivative according to the invention;
  b) Identifying and characterizing said molecule; and
  c) Producing said molecule in substantially isolated and purified form.

Other aspects and embodiments of the present invention are also provided as arising from the following detailed description of the invention.

It should be noted that, where used throughout, the following terms: "modulation/mediation of the TRAF (or TRAF2) effect on cells" and any other such "modulation/mediation" mentioned in the specification are understood to encompass in vitro as well as in vivo treatment and, in addition, also to encompass inhibition or enhancement/augmentation.

DESCRIPTION OF FIGURES

FIG. 3A shows the nucleotide sequence of IREN's 5-prime UTR (from the beginning of the sequence until ATG with Kozak sequence) which is identical in all 3 IREN splice isoforms (SEQ ID NO:3).

FIG. 3B: shows the nucleotide sequence of IREN (SEQ ID NO:4).

FIG. 4: shows the nucleotide sequence of IREN-10B (SEQ ID NO:5).

FIG. 5: shows the nucleotide sequence of IREN-E (SEQ ID NO:6).

FIG. 6: shows the amino acid sequence of IREN (SEQ ID NO:7).

FIG. 7: shows the amino acid sequence of IREN-10B (SEQ ID NO:8).

Figure 8:
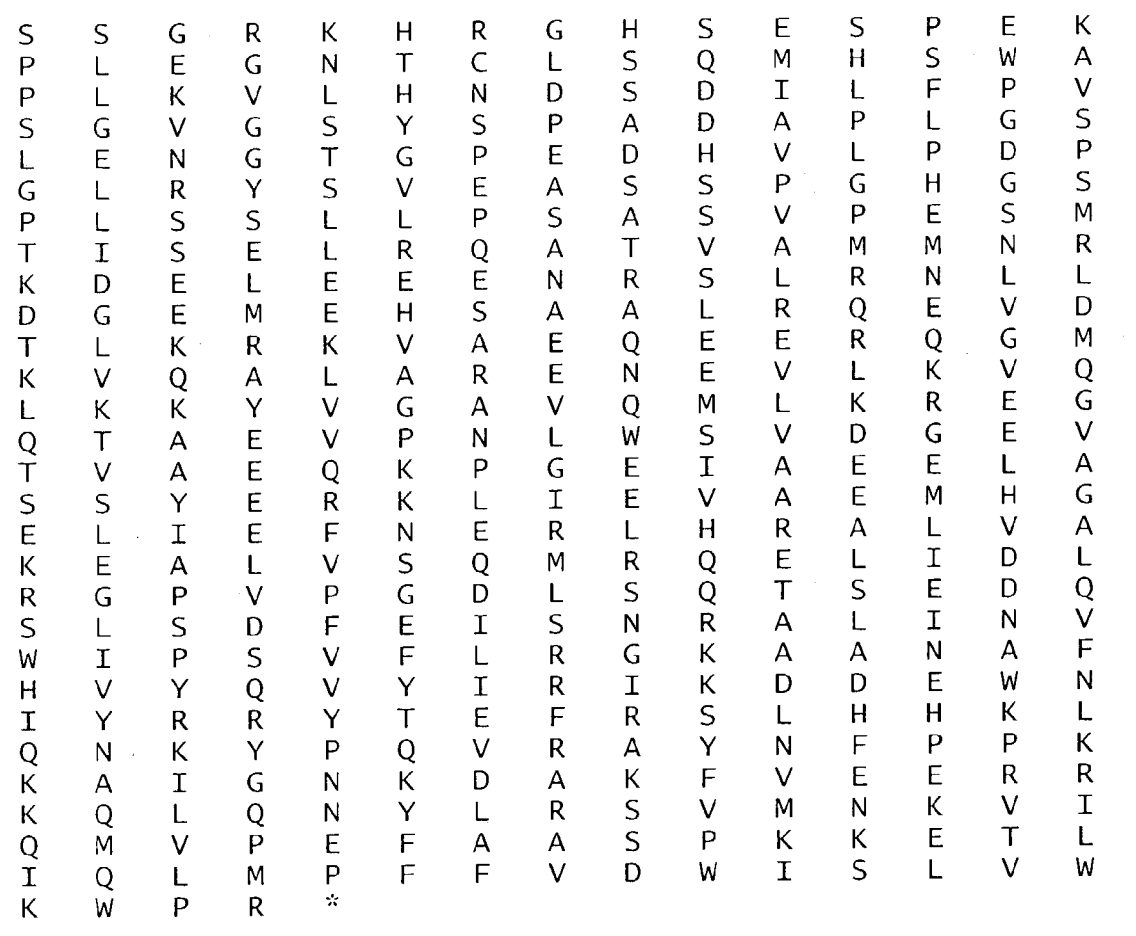

FIG. 8: shows the amino acid sequence of IREN-E (SEQ ID NO:9).

FIG. 10: shows in a diagrammatic fashion results of induction of NF-κB activation by IKK-1, by wild type IREN, NIK and NEMO and mutants thereof.

FIGS. 13A-13H present the results of gene databank analyses suggesting that genes closely related to IREN exist on several of the human chromosomes. FIG. 13A shows nine analysis against the htgs databank. FIG. 13B shows five analysis against the est databank. The query (top strand) in each of the homology analyses of FIGS. 13A and 13B is nucleotides 498-699 of SEQ ID NO:4. The SEQ ID NOs for the strands designated "sbjct" (bottom strand) in the different homology analyses are as follows:

FIG. 13A, first and second analysis, nucleotides 498-699 of SEQ ID NO:4;
FIG. 13A, third through seventh analysis, SEQ ID NO:10;
FIG. 13A, eight analysis, SEQ ID NO:11;
FIG. 13A, ninth analysis, SEQ ID NO:12;
FIG. 13B, first analysis, nucleotides 498-699 of SEQ ID NO:4; and
FIG. 13B, second through fifth analysis, SEQ ID NO:10.

DETAILED DESCRIPTION OF THE INVENTION

The present invention concerns a cDNA sequence herein designated IREN, (depicted in FIG. 3), which encodes for a protein capable of binding to TRAF2, and the proteins encoded by this DNA sequences. The invention also concerns cDNA sequences of IREN isoforms IREN-10B and IREN-E (depicted in FIGS. 4 and 5, respectively).

The DNA and the deduced amino acid sequences mentioned above do not appear in the 'GENEBANK' or 'PROTEIN BANK' data banks of DNA or amino acid sequences, they thus represent hitherto unknown sequences.

Within the scope of the present invention are also fragments of the above mentioned DNA sequences and DNA sequences capable of hybridization to those sequences or part of them, under moderately stringent conditions, provided they encode a biologically active protein or polypeptide capable of binding to at least the 225-501 amino acid sequence of TRAF2.

The present invention also concerns a DNA sequence which is degenerate as a result of the genetic code to the above mentioned DNA sequences and which encodes a biologically active protein or polypeptide capable of binding to at least the 225-501 amino acid sequence of TRAF2.

Figure 1:
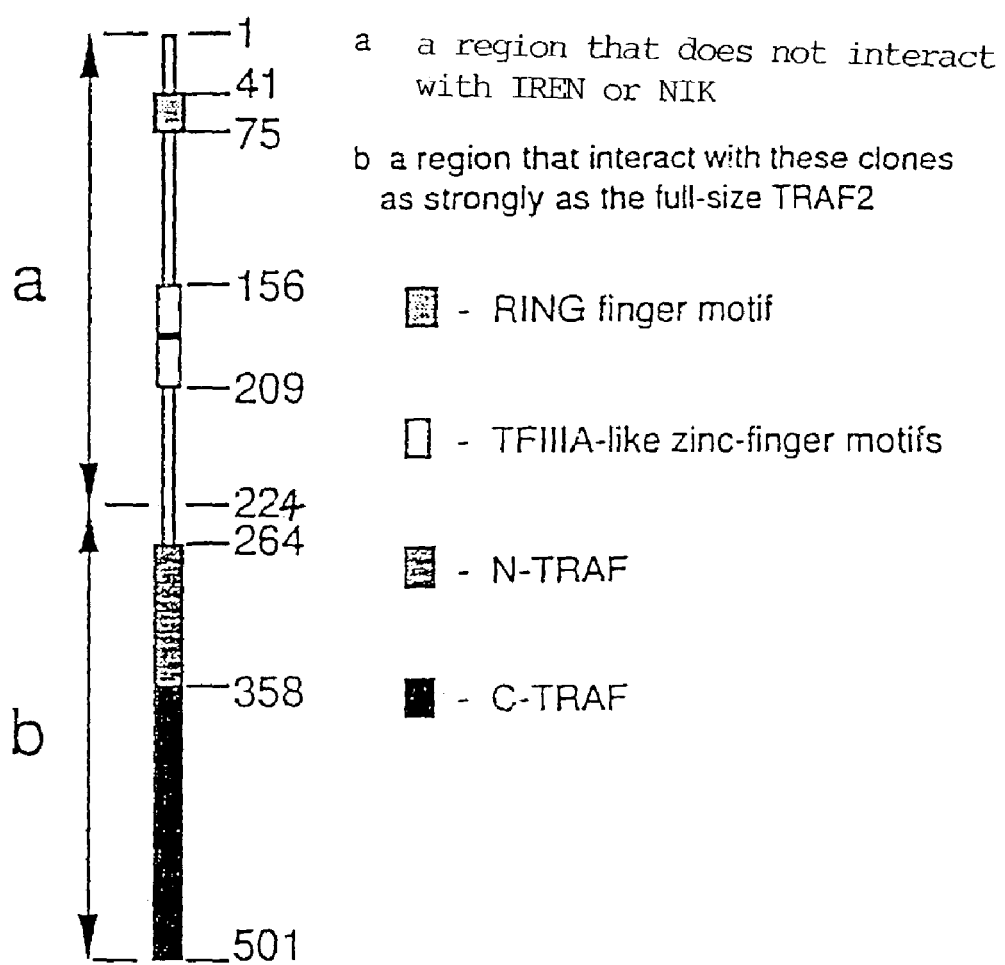
FIG. 1: shows a diagrammatic illustration of the structure of the TRAF2 molecule.
Figure 2:
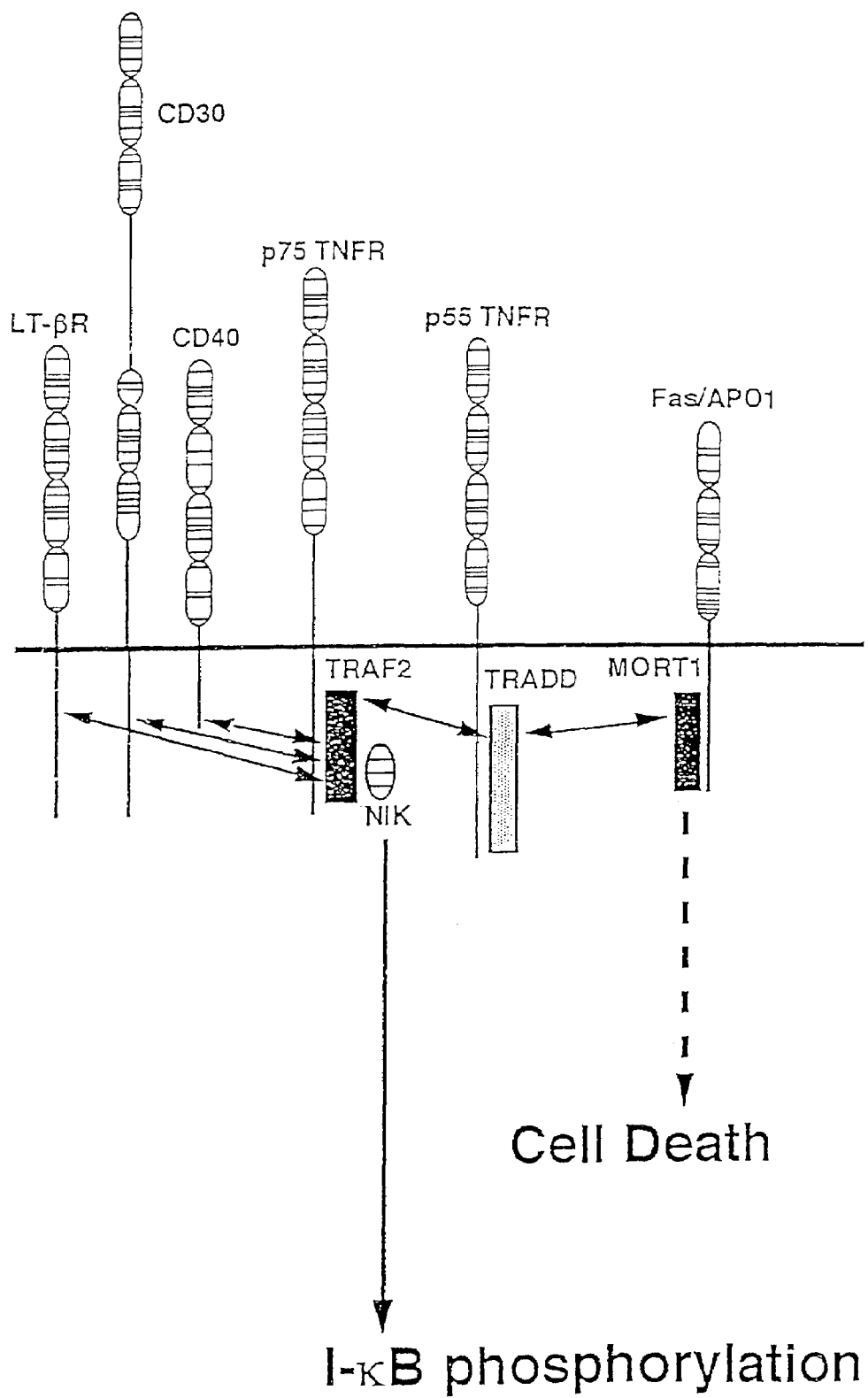
FIG. 2: shows a schematic diagram illustrating some of the proteins involved in NF-κB activation.

As regards TRAF2, it should be noted that several members of the TNF/NGF receptor family activate the transcription factor NF-κB by direct or indirect association with TRAF2, which is thus an adapter protein for these receptors and may thus also be considered as a modulator/mediator of the induction of NF-κB activation activity of these TNF/NGF receptors (see the scheme in FIG. 2). Another receptor, the IL-1 receptor activates NF-κB independently of TRAF2. IREN analogs or muteins produced in accordance with the present invention (see Examples) otherwise modulate NF-κB activation, when these analogs/muteins are expressed in cells.

Thus, the present invention concerns the IREN protein, as well as the biologically active isoforms, analogs, fragments and derivatives thereof, and the isoforms, analogs, fragments and derivatives of the proteins encoded thereby. The preparation of such analogs, fragments and derivatives is by standard procedures (see for example, Sambrook et al., 1989) in which in the DNA encoding sequences, one or more codons may be deleted, added or substituted by another, to yield encoded analogs having at least a one amino acid residue change with respect to the native protein. Acceptable analogs are those which retain at least the capability of binding to TRAF2 with or without mediating any other binding or enzymatic activity, e.g. analogs which bind TRAF2 but do not signal, i.e. do not bind to a further downstream protein or other factor, or do not catalyze a signal-dependent reaction. In such a way analogs can be produced which have a so-called dominant-negative effect, namely, an analog, which is defective either in binding to TRAF2 or in subsequent signaling following such binding as, noted above. Such analogs can be used, for example, to inhibit the CD40, p55 TNF and p75 TNF (FAS/APO1 and other related receptor effects, as well as effected mediated by various receptor associated proteins (adapters) as noted above, by competing with the natural IREN proteins. Likewise, so-called dominant-positive analogs may be produced which would serve to enhance the TRAF2 effect. These would have the same or better TRAF2-binding properties and the same or better signaling properties than natural TRAF2-binding proteins. In an analogous fashion, biologically active fragments of the clones of the invention may be prepared as noted above with respect to the preparation of the analogs. Suitable fragments of the DNA sequences of the invention are those that encode a protein or polypeptide retaining the TRAF2 binding capability or which can mediate any other binding or enzymatic activity as noted above. Accordingly, fragments of the encoded proteins of the invention can be prepared which have a dominant-negative or a dominant-positive effect as noted above with respect to the analogs. Similarly, derivatives may be prepared by standard modifications of the side groups of one or more amino acid residues of the proteins, their analogs or fragments, or by conjugation of the proteins, their analogs or fragments, to another molecule e.g. an antibody, enzyme, receptor, etc., as are well known in the art.

Of the above DNA sequences of the invention which encode the TRAF2-binding protein IREN, biologically active isoforms, analogs, fragments or derivatives, there is also included, as an embodiment of the invention, DNA sequences capable of hybridizing with a cDNA sequence derived from the coding region of a native TRAF-binding protein, in which such hybridization is performed under moderately stringent conditions, and which hybridizable DNA sequences encode a biologically active TRAF-binding protein. These hybridizable DNA sequences therefore include DNA sequences which have a relatively high homology to the native IREN cDNA sequence and as such represent TRAF-binding protein-like sequences which may be, for example, naturally-derived sequences encoding the various IREN isoforms, or naturally-occurring sequences encoding proteins belonging to a group of TRAF-binding protein-like sequences encoding IREN. Further, these sequences may also, for example, include non-naturally occurring, synthetically produced sequences, that are similar to the native IREN cDNA sequence but incorporate a number of desired modifications. Such synthetic sequences therefore include all of the possible sequences encoding analogs, fragments and derivatives of IREN, all of which have the activity of TRAF-binding proteins.

As used herein, stringency conditions are a function of the temperature used in the hybridization experiment, the molarity of the monovalent cations and the percentage of formamide in the hybridization solution. To determine the degree of stringency involved with any given set of conditions, one first uses the equation of Meinkoth et al. (1984) for determining the stability of hybrids of 100% identity expressed as melting temperature Tm of the DNA-DNA hybrid:

$$Tm = 81.5° C. + 16.6(\log M) + 0.41(\% \ GC) - 0.61(\% \ form) - 500/L$$

where M is the molarity of monovalent cations, % GC is the percentage of G and C nucleotides in the DNA, % form is the percentage of formamide in the hybridization solution, and L is the length of the hybrid in base pairs. For each 1° C. that the Tm is reduced from that calculated for a 100% identity hybrid, the amount of mismatch permitted is increased by about 1%. Thus, if the Tm used for any given hybridization experiment at the specified salt and formamide concentrations is 10° C. below the Tm calculated for a 100% hybrid according to the equation of Meinkoth, hybridization will occur even if there is up to about 10% mismatch.

Thus "highly stringent conditions" are those which provide a Tm which is not more than 10° C. below the Tm that would exist for a perfect duplex with the target sequence, either as calculated by the above formula or as actually measured. "Moderately stringent conditions" are those which provide a Tm which is not more than 20° C. below the Tm that would exist for a perfect duplex with the target sequence, either as calculated by the above formula or as actually measured. Without limitation, examples of highly stringent (5-10° C. below the calculated or measured Tm of the hybrid) and moderately stringent (15-20° C. below the calculated or measured Tm of the hybrid) conditions use a wash solution of 2×SSC (standard saline citrate) and 0.5% SDS (sodium dodecyl sulfate) at the appropriate temperature below the calculated Tm of the hybrid. The ultimate stringency of the conditions is primarily due to the washing conditions, particularly if the hybridization conditions used are those which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE (standard saline-phosphate-EDTA)), 5×Denhardt's reagent, 0.5% SDS, 100 µg/ml denatured, fragmented salmon sperm DNA at a temperature approximately 20 to 25 C below the Tm. If mixed probes are used, it is preferable to use tetramethyl ammonium chloride (TMAC) instead of SSC (Ausubel, 1987, 1999).

To obtain the various above noted naturally occurring IREN-like sequences, standard procedures of screening and isolation of naturally-derived DNA or RNA samples from various tissues may be employed using the natural IREN cDNA or portion thereof as probe (see for example standard procedures set forth in Sambrook et al., 1989).

Likewise, to prepare the above noted various synthetic TRAF-binding protein-like sequences encoding analogs, fragments or derivatives of IREN, a number of standard procedures may be used as are detailed herein below concerning the preparation of such analogs, fragments and derivatives.

A polypeptide or protein "substantially corresponding" to IREN includes not only IREN itself but also polypeptides or proteins that are analogs of IREN.

Analogs that substantially correspond to IREN are those polypeptides in which one or more amino acid of IREN's amino acid sequence has been replaced with another amino acid, deleted and/or inserted, provided that the resulting protein exhibits substantially the same or higher biological activity as IREN.

In order to substantially correspond to IREN, the changes in the sequence of the proteins, such as isoforms are generally relatively minor. Although the number of changes may be more than ten, preferably there are no more than ten changes, more preferably no more than five, and most preferably no more than three such changes. While any technique can be used to find potentially biologically active proteins, which substantially correspond to IREN, one such technique is the use of conventional mutagenesis techniques on the DNA encoding the protein, resulting in a few modifications. The proteins expressed by such clones can then be screened for their ability to bind to TRAF proteins (e.g. TRAF2) and to modulate TRAF protein (e.g. TRAF2) activity in modulation/mediation of the intracellular pathways noted above.

"Conservative" changes are those changes which would not be expected to change the activity of the protein and are usually the first to be screened as these would not be expected to substantially change the size, charge or configuration of the protein and thus would not be expected to change the biological properties thereof.

Conservative substitutions of IREN include an analog wherein at least one amino acid residue in the polypeptide has been conservatively replaced by a different amino acid. Such substitutions preferably are made in accordance with the following list as presented in Table IA, which substitutions may be determined by routine experimentation to provide modified structural and functional properties of a synthesized polypeptide molecule while maintaining the biological activity characteristic of IREN.

TABLE IA

| Original Residue | Exemplary Substitution |
|---|---|
| Ala | Gly; Ser |
| Arg | Lys |
| Asn | Gln; His |
| Asp | Glu |
| Cys | Ser |

TABLE IA-continued

| Original Residue | Exemplary Substitution |
| --- | --- |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Alternatively, another group of substitutions of IREN are those in which at least one amino acid residue in the polypeptide has been removed and a different residue inserted in its place according to the following Table IB. The types of substitutions which may be made in the polypeptide may be based on analysis of the frequencies of amino acid changes between a homologous protein of different species, such as those presented in Table 1-2 of Schulz et al., G. E., Principles of Protein Structure Springer-Verlag, New York, N.Y., 1798, and FIGS. 3-9 of Creighton, T E., Proteins: Structure and Molecular Properties, W.H. Freeman & Co., San Francisco, Calif. 1983. Based on such an analysis, alternative conservative substitutions are defined herein as exchanges within one of the following five groups:

TABLE IB

1. Small aliphatic, nonpolar or slightly polar residues: Ala, Ser, Thr (Pro, Gly);
2. Polar negatively charged residues and their amides: Asp, Asn, Glu, Gln;
3. Polar, positively charged residues: His, Arg, Lys;
4. Large aliphatic nonpolar residues: Met, Leu, Ile, Val (Cys); and
5. Large aromatic residues: Phe, Tyr, Trp.

The three amino acid residues in parentheses above have special roles in protein architecture. Gly is the only residue lacking any side chain and thus imparts flexibility to the chain. This however tends to promote the formation of secondary structures other than α-helical. Pro, because of its unusual geometry, tightly constrains the chain and generally tends to promote β-turn-like structures, although in some cases Cys can be capable of participating in disulfide bond formation, which is important in protein folding. Note that Schulz et al., supra, would merge Groups 1 and 2, above. Note also that Tyr, because of its hydrogen bonding potential, has significant kinship with Ser, and Thr, etc.

Conservative amino acid substitutions according to the present invention, e.g., as presented above, are known in the art and would be expected to maintain biological and structural properties of the polypeptide after amino acid substitution. Most deletions and substitutions according to the present invention are those which do not produce radical changes in the characteristics of the protein or polypeptide molecule. "Characteristics" is defined in a non-inclusive manner to define both changes in secondary structure, e.g. α-helix or β-sheet, as well as changes in biological activity, e.g., binding to TRAF proteins and/or mediation of TRAF proteins' effect on cell death.

Examples of production of amino acid substitutions in proteins which can be used for obtaining analogs of IRENs for use in the present invention include any known method steps, such as presented in U.S. Pat. Nos. RE 33,653, 4,959,314, 4,588,585 and 4,737,462, to Mark et al.; U.S. Pat. No. 5,116,943 to Koths et al., U.S. Pat. No. 4,965,195 to Namen et al.; U.S. Pat. No. 4,879,111 to Chong et al.; and U.S. Pat. No. 5,017,691 to Lee et al.; and lySine substituted proteins presented in U.S. Pat. No. 4,904,584 (Shaw et al.).

Besides conservative substitutions discussed above which would not significantly change the activity of IREN, either conservative substitutions or less conservative and more random changes, which lead to an increase in biological activity of the analogs of IRENs, are intended to be within the scope of the invention.

When the exact effect of the substitution or deletion is to be confirmed, one skilled in the art will appreciate that the effect of the substitution(s), deletion(s), etc., will be evaluated by routine binding and cell death assays. Screening using such a standard test does not involve undue experimentation.

At the genetic level, these analogs are generally prepared by site-directed mutagenesis of nucleotides in the DNA encoding the IREN, thereby producing DNA encoding the analog, and thereafter synthesizing the DNA and expressing the polypeptide in recombinant cell culture. The analogs typically exhibit the same or increased qualitative biological activity as the naturally occurring protein, Ausubel et al., Current Protocols in Molecular Biology, Greene Publications and Wiley Interscience, New York, N.Y., 1987-1995; Sambrook et al., Molecular Cloning: A Laboratory Manual, Cold Spring Harbor Laboratory, Cold Spring Harbor, N.Y., 1989.

Preparation of an IREN mutein in accordance herewith, or an alternative nucleotide sequence encoding the same polypeptide but differing from the natural sequence due to changes permitted by the known degeneracy of the genetic code, can be achieved by site-specific mutagenesis of DNA that encodes an earlier prepared analog or a native version of an IREN. Site-specific mutagenesis allows the production of analogs through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 complementing nucleotides on each side of the sequence being altered. In general, the technique of site-specific mutagenesis is well known in the art, as exemplified by publications such as Adelman et al., *DNA* 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phages are readily available commercially and their use is generally well known to those skilled in the art. Alternatively, plasmid vectors that contain a single-stranded phage origin of replication (Veira et al., *Meth. Enzymol.* 153:3, 1987) may be employed to obtain single-stranded DNA.

In general, site-directed mutagenesis in accordance herewith is performed by first obtaining a single-stranded vector that includes within its sequence a DNA sequence that encodes the relevant polypeptide. An oligonucleotide primer bearing the desired mutated sequence is prepared synthetically by automated DNA/oligonucleotide synthesis. This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells, such as *E. coli* JM101 cells, and clones are selected that include recombinant vectors bearing the mutated sequence arrangement.

After such a clone is selected, the mutated IREN sequence may be removed and placed in an appropriate vector, generally a transfer or expression vector of the type that may be employed for transfection of an appropriate host.

Accordingly, a gene or nucleic acid coding for an IREN protein can also be detected, obtained and/or modified, in vitro, in situ and/or in vivo, by the use of known DNA or RNA amplification techniques, such as PCR and chemical oligonucleotide synthesis. PCR allows for the amplification (increase in number) of specific DNA sequences by repeated DNA polymerase reactions. This reaction can be used as a replacement for cloning; all that is required is knowledge of the nucleic acid sequence. In order to carry Out PCR, primers are designed which are complementary to the sequence of interest. The primers are then generated by automated DNA synthesis. Because primers can be designed to hybridize to any part of the gene, conditions can be created such that mismatches in complementary base pairing can be tolerated. Amplification of these mismatched regions can lead to the synthesis of a mutagenized product resulting in the generation of a peptide with new properties (i.e., site directed mutagenesis). See also, e.g., Ausubel, supra, Ch. 16. Also, by coupling complementary DNA (cDNA) synthesis, using reverse transcriptase, with PCR, RNA can be used as the starting material for the synthesis of the extracellular domain of a prolactin receptor without cloning.

Furthermore, PCR primers can be designed to incorporate new restriction sites or other features such as termination codons at the ends of the gene segment to be amplified. This placement of restriction sites at the 5' and 3' ends of the amplified gene sequence allows for gene segments encoding an IREN protein or a fragment thereof to be custom designed for ligation other sequences and/or cloning sites in vectors.

PCR and other methods of amplification of RNA and/or DNA are well known in the art and can be used according to the present invention without undue experimentation, based on the teaching and guidance presented herein. Known methods of DNA or RNA amplification include, but are not limited to polymerase chain reaction (PCR) and related amplification processes (see, e.g., U.S. Pat. Nos. 4,683,195, 4,683,202, 4,800,159, 4,965,188, to Mullis et al.; 4,795,699 and 4,921,794 to Tabor et al.; 5,142,033 to Innis; 5,122,464 to Wilson et al.; 5,091,310 to Innis; 5,066,584 to Gyllensten et al.; 4,889,818 to Gelfand et al.; 4,994,370 to Silver et al.; 4,766,067 to Biswas; 4,656,134 to Ringold; and Innis et al., eds, *PCR Protocols: A Guide to Method and Applications*) and RNA mediated amplification which uses anti-sense RNA to the target sequence as a template for double stranded DNA synthesis (U.S. Pat. No. 5,130,238 to Malek et al. with the trade name NASBA); and immuno-PCR which combines the use of DNA amplification with antibody labeling (Ruzicka et al., *Science* 260:487 (1993); Sano et al., *Science* 258:120 (1992); Sano et al., *Biotechniques* 9:1378 (1991)), the entire contents of which patents and reference are entirely incorporated herein by reference.

In an analogous fashion, biologically active fragments of IREN or its isoforms may be prepared as noted above with respect to the analogs of TRAF-binding proteins. Suitable fragments of TRAF-binding proteins are those which retain the TRAF-binding protein capability and which can mediate the biological activity of TRAF proteins or other proteins associated with TRAF proteins directly or indirectly. Accordingly, IREN fragments can be prepared which have a dominant-negative or a dominant-positive effect as noted above with respect to the analogs. It should be noted that these fragments represent a special class of the analogs of the invention, namely, they are defined portions of IREN derived from the full IREN sequence or its isoforms, each such portion or fragment having any of the above-noted desired activities. Such fragment may be, e.g., a peptide.

Similarly, derivatives may be prepared by standard modifications of the side groups of one or more amino acid residues of IREN, its analogs or fragments, or by conjugation of the IREN, its analogs or fragments, to another molecule e.g. an antibody, enzyme, receptor, etc., as are well known in the art. Accordingly, "derivatives" as used herein covers derivatives which may be prepared from the functional groups which occur as side chains on the residues or the N- or C-terminal groups, by means known in the art, and are included in the invention. Derivatives may have chemical moieties such as carbohydrate or phosphate residues, provided such a fraction has the same or higher biological activity than IREN proteins.

For example, derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (for example that of seryl or threonyl residues) formed with acyl moieties.

The term "derivatives" is intended to include only those derivatives that do not change one amino acid to another of the twenty commonly occurring natural amino acids.

An IREN protein is a protein or polypeptide, i.e. a sequence of amino acid residues. A polypeptide consisting of a larger sequence which includes the entire sequence of an IREN protein, in accordance with the definitions herein, is intended to be included within the scope of such a polypeptide as long as the additions do not affect the basic and novel characteristics of the invention, i.e., if they either retain or increase the biological activity of IREN or can be cleaved to leave a protein or polypeptide having the biological activity of IREN. Thus, for example, the present invention is intended to include fusion proteins of IREN with other amino acids or peptides.

As mentioned above, it should be understood that the above IREN, isoforms, fragments, derivatives, muteins etc. of the invention are any proteins which may bind and/or mediate/modulate the activity of any TRAF protein intracellularly. In particular, examples are those proteins which can modulate or mediate the TRAF2-associated intracellular signaling activity, as mentioned above, especially as concerns TRAF2's involvement in modulating NF-κB activity, in particular, following the interaction between TRAF2 and various members of the TNF/NGF receptor family and/or their associated adapter proteins as detailed above and below. IREN according to the invention and its various isoforms analogs, fragments, etc. (see Examples) which appear to bind TRAF2 very specifically and to have an action in modulating NF-κB activity, with IREN dominant-negative analogs/muteins modulating this activity, do so.

All the above mentioned modifications are in the scope of the invention provided they preserved the ability of the encoded proteins or polypeptides or their analogs and derivatives thereof, to bind at least the 225-501 amino acid sequence of TRAF2.

All the proteins and polypeptides of the invention by virtue of their capability to bind to TRAF2, are considered as mediators or modulators of TRAF2 signaling. As such, said molecules of the invention have a role in, for example, the signaling process in which the binding of TRAF2 ligand to CD30, CD40, lymphotoxin beta (LT-β) receptor, p55 or p75 TNF receptors, as well as the other receptors and adaptor proteins noted herein above, leads to activation of the transcription factor NF-κB. Particularly interesting is protein IREN and its isoforms of the invention.

The new clones, proteins, their analogs, fragments and derivatives have a number of possible uses, for example:

(i) They may be used to modulate NFκB activity, the function of TRAF2 and the receptors to which they bind, in situations where a modulation of function is desired such as in anti-tumor or immuno-stimulatory applications where the TRAF2-induced effects are desired. In this case the proteins of the invention, their analogs, fragments or derivatives, which modulate the TRAF2 or receptors effects, may be introduced to the cells by standard procedures known per se. For example, as the proteins encoded by the DNA clones of the invention are intracellular and they should be introduced only into the cells where the TRAF2 effect is desired, a system for specific introduction of these proteins into the cells is necessary. One way of doing this is by creating a recombinant animal virus e.g. one derived from Vaccinia, to the DNA of which the following two genes will be introduced: the gene encoding a ligand that binds to cell surface proteins specifically expressed by the cells e.g. ones such as the AIDs (HIV) virus gp120 protein which binds specifically to some cells (CD4 lymphocytes and related leukemias) or any other ligand that binds specifically to cells carrying a receptor that binds TRAF2, such that the recombinant virus vector will be capable of binding such cells; and the gene encoding the proteins of the invention. Thus, expression of the cell-surface-binding protein on the surface of the virus will target the virus specifically to the tumor cell or other receptor-carrying cell, following which the proteins encoding sequences will be introduced into the cells via the virus, and once expressed in the cells will result in enhancement of the receptor or TRAF2 effect leading to a desired immuno-stimulatory effect in these cells. Construction of such recombinant animal virus is by standard procedures (see for example, Sambrook et al., 1989). Another possibility is to introduce the sequences of the encoded proteins in the form of oligonucleotides, which can be absorbed by the cells and expressed therein.

(ii) They may be used to modulate the NFκB activity, the effects of TRAF2 or of the receptor that binds it, e.g. in cases such as tissue damage as in AIDS, septic shock or graft-vs.-host rejection, in which it is desired to block the induced intracellular signaling. In this situation it is possible, for example, to introduce into the cells, by standard procedures, oligonucleotides having the anti-sense coding sequence for the proteins of the invention, which would effectively block the translation of mRNAs encoding the proteins and thereby block their expression and lead to the inhibition of the undesired effect. Alternatively, other oligonucleotides may be used; oligonucleotides that preserved their ability to bind to TRAF2 in a way that interferes with the binding of other molecules to this protein, while at the same time do not mediate any activation or modulation of this molecule. Having these characteristics, said molecules can disrupt the interaction of TRAF2 with its natural ligand, therefor acting as inhibitors capable of abolishing effects mediated by TRAF2, such as NF-κB activation, for example. Such oligonucleotides may be introduced into the cells using the above recombinant virus approach, the second sequence carried by the virus being the oligonucleotide sequence.

Another possibility is to use antibodies specific for the proteins of the invention to inhibit their intracellular signaling activity.

Yet another way of inhibiting the undesired effect is by the recently developed ribozyme approach. Ribozymes are catalytic RNA molecules that specifically cleave RNAs. Ribozymes may be engineered to cleave target RNAs of choice, e.g. the mRNAs encoding the proteins of the invention. Such ribozymes would have a sequence specific for the mRNA of the proteins and would be capable of interacting therewith (complementary binding) followed by cleavage of the mRNA, resulting in a decrease (or complete loss) in the expression of the proteins, the level of decreased expression being dependent upon the level of ribozyme expression in the target cell. To introduce ribozymes into the cells of choice (e.g. those carrying the IREN proteins) any suitable vector may be used, e.g. plasmid, animal virus (retrovirus) vectors, that are usually used for this purpose (see also (i) above, where the virus has, as second sequence, a cDNA encoding the ribozyme sequence of choice). (For reviews, methods etc. concerning ribozymes see Chen et al., 1992; Zhao and Pick, 1993).

(iii) They may be used to isolate, identify and clone other proteins which are capable of binding to them, e.g. other proteins involved in the intracellular signaling process that are downstream of TRAF2. For example, the DNA sequences encoding the proteins of the invention may be used in the yeast two-hybrid system in which the encoded proteins will be used as "bait" to isolate, clone and identify from cDNA or genomic DNA libraries other sequences ("preys") encoding proteins which can bind to the cloned proteins. In the same way, it may also be determined whether the proteins of the present invention can bind to other cellular proteins, e.g. other receptors of the TNF/NGF superfamily of receptors.

(iv) The encoded proteins, their analogs, fragments or derivatives may also be used to isolate, identify and clone other proteins of the same class i.e. those binding to TRAF2 or to functionally related proteins, and involved in the intracellular signaling process. In this application the above noted yeast two-hybrid system may be used, or there may be used a recently developed system employing non-stringent Southern hybridization followed by PCR cloning (Wilks et al. 1989).

(v) Yet another approach to utilize the encoded proteins of the invention, their isoforms analogs, fragments or derivatives is to use them in methods of affinity chromatography to isolate and identify other proteins or factors to which they are capable of binding, e.g., proteins related to TRAF2 or other proteins or factors involved in the intracellular signaling process. In this application, the protein, its isoforms analogs, fragments or derivatives of the present invention, may be individually attached to affinity chromatography matrices and then brought into contact with cell extracts or isolated proteins or factors suspected of being involved in the intracellular signaling process. Following the affinity chromatography procedure, the other proteins or factors which bind to the proteins, their analogs, fragments or derivatives of the invention, can be eluted, isolated and characterized.

(vi) As noted above, the proteins, their analogs, fragments or derivatives of the invention may also be used as immunogens (antigens) to produce specific antibodies thereto. These antibodies may also be used for the purposes of purification of the protein of the invention either from cell extracts or from transformed cell lines producing them, their analogs or fragments. Further, these antibodies may be used for diagnostic purposes for identifying disorders related to abnormal functioning of the receptor system in which they function, e.g., overactive or under active TRAF2-induced cellular effects. Thus, should such disorders be related to a malfunctioning intracellular signaling system involving the proteins of the invention, such antibodies would serve as an important diagnostic tool. The term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments thereof, such as, for example, Fab and $F(ab')_2$-fragments lacking the Fc fragment of intact antibody, which are capable of binding antigen.

(vii) The antibodies, including fragments of antibodies, useful in the present invention may be used to quantitatively or qualitatively detect the clones of the invention in a sample, or to detect presence of cells which express the clones of the present invention. This can be accomplished by immunofluorescence techniques employing a fluorescently labeled antibody coupled with light microscopic, flow cytometric, or fluorometric detection.

The antibodies (or fragments thereof) useful in the present invention may be employed histologically, as in immunofluorescence or immunoelectron microscopy, for in situ detection of the clones of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the clones, but also its distribution on the examined tissue. Using the present invention, those of ordinary skill will readily perceive that any of wide variety of histological methods (such as staining procedures) can be modified in order to achieve such in situ detection.

Such assays for the clones of the present invention typically comprise incubating a biological sample, such as a biological fluid, a tissue extract, freshly harvested cells Such as lymphocytes or leukocytes, or cells which have been incubated in tissue culture, in the presence of a labeled antibody capably of identifying the encoded proteins, and detecting the antibody by any of a number of techniques well known in the art.

(viii) The encoded proteins of the invention may also be used as indirect modulators of a number of other proteins by virtue of their capability of binding to other intracellular proteins, which other intracellular proteins directly bind yet other intracellular proteins or an intracellular domain of a transmembrane protein.

For the purposes of modulating these other intracellular proteins or the intracellular domains of transmembranal proteins, the proteins of the invention may be introduced into cells in a number of ways as mentioned hereinabove in (ii).

It should also be noted that the isolation, identification and characterization of the proteins of the invention might be performed using any of the well-known standard screening procedures. For example, one of these screening procedures, the yeast two-hybrid procedure which was used to identify the proteins of the invention. Likewise other procedures may be employed such as affinity chromatography, DNA hybridization procedures, etc. as are well known in the art, to isolate, identify and characterize the proteins of the invention or to isolate, identify and characterize additional proteins, factors, receptors, etc. which are capable of binding to the proteins of the invention.

Moreover, the proteins found to bind to the proteins of the invention may themselves be employed, in an analogous fashion to the way in which the proteins of the invention were used as noted above and below, to isolate, identify and characterize other proteins, factors, etc. which are capable of binding to the proteins of the invention-binding proteins and which may represent factors involved further downstream in the associated signaling process, or which may have signaling activities of their and hence would represent proteins involved in a distinct signaling process.

The DNA sequences and the encoded proteins of the invention may be produced by any standard recombinant DNA procedure (see for example, Sambrook, et al., 1989) in which suitable eukaryotic or prokaryotic host cells are transformed by appropriate eukaryotic or prokaryotic vectors containing the sequences encoding for the proteins. Accordingly, the present invention also concerns such expression vectors and transformed hosts for the production of the proteins of the invention. As mentioned above, these proteins also include their biologically active analogs, fragments and derivatives, and thus the vectors encoding them also include vectors encoding analogs and fragments of these proteins, and the transformed hosts include those producing such analogs and fragments. The derivatives of these proteins are the derivatives produced by standard modification of the proteins or their analogs or fragments, produced by the transformed hosts.

The present invention also relates to pharmaceutical compositions for modulation of the effects mediated by TRAF2. The pharmaceutical compositions comprising, as an active ingredient, any one or more of the following: (i) one or more of the DNA sequences of the invention, or parts of them, subcloned into an appropriate expression vector; (ii) a protein according to the invention, its biologically active fragments, analogs, derivatives or a mixture thereof, (iii) a recombinant animal virus vector encoding for a protein according to the invention, its biologically active fragments, analogs or derivatives.

The pharmaceutical compositions are applied according to the disease to be treated and in amounts beneficial to the patent, depending on body weight and other considerations, as determined by the physician.

As noted above, one of the specific embodiments of the TRAF-binding proteins of the present invention is the TRAF2-binding protein IREN. Based on the findings in accordance with the present invention that IREN binds specifically to TRAF2 and as such is a mediator/modulator of TRAF2 and can thus mediate/modulate TRAF2's activity in NF-κB activation and hence its possible role in cell survival pathways in ways that TRAF2 functions independently or in conjunction with other proteins (e.g. p55 TNF and p75 TNF receptors, FAS/APO1 receptor, MORT-1, RIP and TRADD) it is of importance to design drugs which may enhance or inhibit the TRAF2-IREN interaction, as desired. For example, when it is desired to modulate the cell cytotoxicity induced by TNF it would be desired to modulate NF-κB induction, by modulating the TRAF2-IREN interaction or by modulating TRAF2 and/or IREN specifically. Likewise, for example, when it is desired to modulate the cell cytotoxicity induced by TNF it would be desired to modulate NF-κB induction by modulating the TRAF2-IREN interaction or by modulating TRAF2- and/or IREN specific NF-κB modulation. There are many diseases in which such drugs can be of great help. Amongst others, (see above discussion as well)

acute hepatitis in which the acute damage to the liver seems to reflect FAS/APO1 receptor-mediated death of the liver cells following induction by the Fas ligand; autoimmune-induced cell death such as the death of the 3 Langerhans cells of the pancreas, that results in diabetes; the death of cells in graft rejection (e.g., kidney, heart and liver); the death of oligodendrocytes in the brain in multiple sclerosis; and AIDS-inhibited T cell suicide which causes proliferation of the AIDS virus and hence the AIDS disease.

It is possible that IREN or one or more of its possible biologically active isoforms, analogs or fragments may serve as "natural" inhibitors of IREN itself or of the IREN-TRAF2 interaction, and as such serve as modulators of NF-κB activation. Such modulators may thus be employed as the specific modulators noted above, for example, those modulators to be used when it is desired to modulate the cell cytotoxic effects of TNF. In fact, as exemplified herein below, various IREN analogs and muteins have been isolated in accordance with the present invention, which are capable of modulating the induction of NF-κB activation mediated by NIK, NEMO, IKK-1 or fragments thereof. And also as mediated by bacterial endotoxin (LPS), phorbol myristate acetate, and the HTLV-1 protein TAX. Likewise, other substances such as peptides, organic compounds, antibodies, etc. may also be screened to obtain specific drugs, which are capable of inhibiting the TRAF2-IREN interaction or the activity of IREN.

In a similar fashion, when it is desired to modulate the NF-κB activation in various situations as noted above it is possible, for example, to modulate the amount of IREN and/or TRAF2 in cells by various standard methods noted herein above (e.g. introducing DNA encoding IREN and/or TRAF2 into cells to modulate expression, or preparing suitable formulations containing IREN and/or TRAF2 for direct introduction into cells, or any other way known to those of skill in the art). Likewise, other substances such as peptides, organic compounds, etc. may also be screened to obtain specific drugs, which are capable of enhancing the activity of IREN or of enhancing the TRAF2-IREN interaction.

A non-limiting example of how peptide modulators of the IREN-TRAF2 interaction would be designed and screened is based on previous studies on peptide inhibitors of ICE or ICE-like proteases, the substrate specificity of ICE and strategies for epitope analysis using peptide synthesis. The minimum requirement for efficient cleavage of a peptide by ICE was found to involve four amino acids to the left of the cleavage site with a strong preference for aspartic acid in the $P_1$ position and with methylamine being sufficient to the right of the $P_1$ position (Sleath et al., 1990; Howard et al., 1991; Thronberry et al., 1992). Furthermore, the fluorogenic substrate peptide (a tetrapeptide), aceptyl-Asp-Glu-Val-Asp-a-(4-methyl-coumaryl-7-amide) (SEQ ID NO:13) abbreviated Ac-DEVD-AMC, corresponds to a sequence in poly (ADP-ribose) polymerase (PARP) found to be cleaved in cells shortly after FAS-R stimulation, as well as other apoptopic processes (Kaufmann, 1989; Kaufmann et al., 1993; Lazebnik et al., 1994), and is cleaved effectively by CPP32 (a member of the CED3/ICE protease family) and MACH proteases.

As Asp in the $P_1$ position of the substrate appears to be important, tetrapeptides having Asp as the fourth amino acid residue and various combinations of amino acids in the first three residue positions can be rapidly screened for binding to the active site of the proteases using, for example, the method developed by Geysen (Geysen, 1985; Geysen et al., 1987) where a large number of peptides on solid supports were screened for specific interactions with antibodies. The binding of MACH proteases to specific peptides can be detected by a variety of well known detection methods within the skill of those in the art, such as radiolabeling, etc. This method of Geysen's was shown to be capable of testing at least 4000 peptides each working day.

In a similar way the exact binding region or region of homology which determines the interaction between TRAF2 and IREN (or any other TRAF protein and TRAF-binding protein) can be elucidated and then peptides may be screened which can serve to block this interaction, e.g. peptides synthesized having a sequence similar to that of the binding region or complementary thereto which can compete with natural IREN (or TRAF-binding protein) for binding to TRAF2 (or TRAF).

Since it may be advantageous to design peptide inhibitors that selectively inhibit TRAF2-IREN (or TRAF-TRAF binding protein) interactions without interfering with physiological cell death processes in which other Members of the intracellular signaling pathway are involved, e.g. MACH proteases of the cell death pathway, which are members of the CED3/ICE family of proteases, the pool of peptides binding to TRAF2 (or TRAF) or IREN (or TRAF-binding proteins) in an assay such as the one described above can be further synthesized as a fluorogenic substrate peptide to test for selective binding to such other proteins to select only those specific for TRAF2/IREN (or TRAF/TRAF-binding protein). Peptides, which are determined to be specific for, for example, TRAF2/IREN, can then be modified to enhance cell permeability and inhibit the activity of TRAF2 and/or IREN either reversibly or irreversibly. Thornberry et al. (1994) reported that a tetrapeptide (acyloxy) methyl ketone Ac-Tyr-Val-Ala-Asp-$CH_2OC(O)$-[2,6-$(CF_3)_2$] Ph (SEQ ID NO:14) was a potent inactivator of ICE. Similarly, Milligan et al. (1995) reported that tetrapeptide inhibitors having a chloromethylketone (irreversibly) or aldehyde (reversibly) groups inhibited ICE. In addition, a benzyloxycarboxyl-Asp-$CH_2OC(\pm)$-2,6-dichlorobenzene (DCB) was shown to inhibit ICE (Mashima et al., 1995). Accordingly, in an analogous way, tetrapeptides that selectively bind to, for example, TRAF2 or IREN, can be modified with, for example, an aldelyde group, chloromethylketone, (acyloxy) methyl ketone or a CH2OC (0)-DCB group to create a peptide inhibitor of TRAF2/IREN activity. Further, to improve permeability, peptides can be, for example, chemically modified or derivatized to enhance their permeability across the cell membrane and facilitate the transport of such peptides through the membrane and into the cytoplasm. Muranishi et al. (1991) reported derivatizing thyrotropin-releasing hormone with lauric acid to form a lipophilic lauroyl derivative with good penetration characteristics across cell membranes. Zacharia et al. (1991) also reported the oxidation of methionine to sulfoxide and the replacement of the peptide bond with its ketomethylene isoester ($COCH_2$) to facilitate transport of peptides through the cell membrane. These are just some of the known modifications and derivatives that are well within the skill of those in the art.

Furthermore, drug or peptide inhibitors, which are capable of inhibiting the activity of, for example, IREN by inhibiting the IREN-TRAF2 interaction and likewise, the interaction between TRAF proteins and TRAF-binding proteins can be conjugated or complexed with molecules that facilitate entry into the cell.

U.S. Pat. No. 5,149,782 discloses conjugating a molecule to be transported across the cell membrane with a membrane blending agent such as fusogenic polypeptides, ion-channel forming polypeptides, other membrane polypeptides, and long chain fatty acids, e.g. myristic acid, palmitic acid. These membrane blending agents insert the molecular conjugates into the lipid bilayer of cellular membranes and facilitate their entry into the cytoplasm.

Low et al., U.S. Pat. No. 5,108,921, reviews available methods for transmembrane delivery of molecules such as, but not limited to, proteins and nucleic acids by the mechanism of receptor mediated endocytotic activity. These receptor systems include those recognizing galactose, mannose, mannose 6-phosphate, transferrin, asialoglycoprotein, transcobalamin (vitamin $B_{12}$), α-2 macroglobulins, insulin and other peptide growth factors such as epidermal growth factor (EGF). Low et al. teaches that nutrient receptors, such as receptors for biotin and folate, can be advantageously used to enhance transport across the cell membrane due to the location and multiplicity of biotin and folate receptors on the membrane surfaces of most cells and the associated receptor mediated transmembrane transport processes. Thus, a complex formed between a compound to be delivered into the cytoplasm and a ligand, such as biotin or folate, is contacted with a cell membrane bearing biotin or folate receptors to initiate the receptor mediated trans-membrane transport mechanism and thereby permit entry of the desired compound into the cell.

ICE is known to have the ability to tolerate liberal substitutions in the $P_2$ position and this tolerance to liberal substitutions was exploited to develop a potent and highly selective affinity label containing a biotin tag (Thornberry et al., 1994). Consequently, the $P_2$ position as well as possibly the N-terminus of the tetrapeptide inhibitor can be modified or derivatized, such as to with the addition of a biotin molecule, to enhance the permeability of these peptide inhibitors across the cell membrane.

In addition, it is known in the art that fusing a desired peptide sequence with a leader/signal peptide sequence to create a "chimeric peptide" will enable such a "chimeric peptide" to be transported across the cell membrane into the cytoplasm.

As will be appreciated by those of skill in the art of peptides, the peptide inhibitors of the TRAF-TRAF-binding protein interaction, for example, the TRAF2-IREN interaction according to the present invention is meant to include peptidomimetic drugs or inhibitors, which can also be rapidly screened for binding to, for example TRAF2/IREN to design perhaps more stable inhibitors.

It will also be appreciated that the same means for facilitating or enhancing the transport of peptide inhibitors across cell membranes as discussed above are also applicable to the TRAF-binding proteins, for example, IREN, its analogs, fragments or its isoforms themselves as well as other peptides and proteins which exert their effects intracellularly.

As regards the antibodies mentioned herein throughout, the term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments thereof provided by any known technique, such as, but not limited to enzymatic cleavage, peptide synthesis or recombinant techniques.

Polyclonal antibodies are heterogeneous populations of antibody molecules derived from the sera of animals immunized with an antigen. A monoclonal antibody contains a substantially homogeneous population of antibodies specific to antigens, which populations contains substantially similar epitope binding sites. MAbs may be obtained by methods known to those skilled in the art. See, for example Kohler and Milstein, Nature, 256:495-497 (1975); U.S. Pat. No. 4,376,110; Ausubel et al., eds., Harlow and Lane ANTIBODIES: A LABORATORY MANUAL, Cold Spring Harbor Laboratory (1988); and Colligan et al., eds., Current Protocols in Immunology, Greene Publishing Assoc. and Wiley Interscience N.Y., (1992-1996), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of mAbs in vivo or in situ makes this the presently preferred method of production.

Chimeric antibodies are molecules of which different portions are derived from different animal species, such as those having the variable region derived from a murine mAb and a human immunoglobulin constant region. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al., *Proc. Natl. Acid. Sci. USA* 81:3273-3277 (1984); Morrison et al., *Proc. Natl. Acad. Sci. USA* 81:6851-6855 (1984); Boulianne et al., *Nature* 312:643-646 (1984); Cabilly et al., European Patent Application 125023 (published Nov. 14, 1984); Neuberger et al., *Nature* 314:268-270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Sahagan et al., *J. Immunol.* 137:1066-1074 (1986); Robinson et al., International Patent Application No. WO8702671 (published May 7, 1987); Liu et al., *Proc. Natl. Acad. Sci USA* 84:3439-3443 (1987); Sun et al., *Proc. Natl. Acad. Sci USA* 84:214-218 (1987); Better et al., *Science* 240:1041-1043 (1988); and Harlow and Lane, ANTIBODIES: A LABORATORY MANUAL, supra. These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g. mouse strain) as the source of the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb, which induced the anti-Id. Thus, by using antibodies to the idiotypic determinants of a mAb, it is possible to identify other clones expressing antibodies of identical specificity.

Accordingly, mAbs generated against IREN, its isoforms, analogs, fragments or derivatives of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an epitope of the above IREN protein, or analogs, fragments and derivatives thereof.

The anti-Id mAbs thus have their own idiotypic epitopes, or "idiotopes" structurally similar to the epitope being evaluated, such as GRB protein-a.

The term "antibody" is also meant to include both intact molecules as well as fragments thereof, such as, for example, Fab and F(ab')2, which are capable of binding antigen. Fab and F(ab')2 fragments lack the Fc fragment of intact antibody, clear more rapidly from the circulation, and may have less non-specific tissue binding than an intact antibody (Wahl et al., *J. Nucl. Med.* 24:316-325 (1983)).

It will be appreciated that Fab and F(ab')2 and other fragments of the antibodies useful in the present invention may be used for the detection and quantitation of the IREN protein according to the methods disclosed herein for intact antibody molecules. Such fragments are typically produced by proteolytic cleavage, using enzymes such as papain (to produce Fab fragments) or pepsin (to produce F(ab')2 fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody, which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody, which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies, including fragments of antibodies, useful in the present invention may be used to quantitatively or qualitatively detect the IREN proteins in a sample or to detect presence of cells that express the IREN proteins of the present invention. This can be accomplished by immunofluorescence techniques employing a fluorescently labeled antibody (see below) coupled with light microscopic, flow cytometric, or fluorometric detection.

The antibodies (or fragments thereof) useful in the present invention may be employed histologically, as in immunofluorescence or immunoelectron microscopy, for in situ detection of the IREN proteins of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the IREN proteins but also its distribution on the examined tissue. Using the present invention, those of ordinary skill will readily perceive that any of a wide variety of histological methods (such as staining procedures) can be modified in order to achieve such in situ detection.

Such assays for the IREN proteins of the present invention typically comprises incubating a biological sample, such as a biological fluid, a tissue extract, freshly harvested cells such as lymphocytes or leukocytes, or cells which have been incubated in tissue culture, in the presence of a labeled antibody capable of identifying the IREN proteins, and detecting the antibody by any of a number of techniques well known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know may other suitable carriers for binding antibody or antigen, or will be able to ascertain the same by use of routine experimentation.

The binding activity of a given lot of antibody, of the invention as noted above, may be determined according to well-known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be labeled is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomeras, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactive labeling the antibodies or antibody fragments, it is possible to detect R-PTPase through the use of a radioimmunoassay (RIA). A good description of RIA may be found in Laboratory Techniques and Biochemistry in Molecular Biology, by Work, T.

S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a g counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, pycocyanin, allophycocyanin, o-phthaldehyde and fluorescamine.

The antibody can also be detectably labeled using fluorescence emitting metals such as $^{152}$E, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined, as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

As mentioned above, the present invention also relates to pharmaceutical compositions comprising recombinant animal virus vectors encoding the IREN protein, which vector also encodes a virus surface protein capable of binding specific target cell (e.g., cancer cells) surface proteins to direct the insertion of the IREN protein sequences into the cells. Further pharmaceutical compositions of the invention comprises as the active ingredient (a) an oligonucleotide sequence encoding an anti-sense sequence of the IREN protein sequence, or (b) drugs that block the IREN protein-TRAF interaction.

Pharmaceutical compositions according to the present invention include a sufficient amount of the active ingredient to achieve its intended purpose. In addition, the pharmaceutical compositions may contain suitable pharmaceutically acceptable carriers comprising excipients and auxiliaries which facilitate processing of the active compounds into preparations which can be used pharmaceutically and which can stabilize such preparations for administration to the subject in need thereof as are well known to those of skill in the art.

The IREN protein and its isoforms or isotypes are suspected to be expressed in different tissues at markedly different levels and apparently also with different patterns of isotypes in an analogous fashion to the expression of various other proteins involved in the intracellular signaling pathways as indicated in the above listed co-owned co-pending patent applications. These differences may possibly contribute to the tissue-specific features of response to the Fas/APO1-ligand and TNF. As in the case of other CED3/ICE homologs (Wang et al., 1994; Alnemri et al., 1995), the present inventors have previously shown (in the above mentioned patent applications) that MACH isoforms that contain incomplete CED3/ICE regions (e.g., MACHα3) are found to have an inhibitory effect on the activity of co-expressed MACHα1 or MACHα2 molecules; they are also found to block death induction by Fas/APO1 and p55-R. Expression of such inhibitory isoforms in cells may constitute a mechanism of cellular self-protection against Fas/APO1- and TNF-mediated cytotoxicity. The wide heterogeneity of MACH isoforms, which greatly exceeds that observed for any of the other proteases of the CED3/ICE family, should allow a particularly fine-tuning of the function of the active MACH isoforms.

In accordance with the present invention there have also been isolated analogs/muteins of the TRAF2-binding protein IREN. Some of these IREN analogs/muteins (see above and see Examples below), such as deletion muteins of IREN modulate NF-κB activation. Hence, as noted above, the IREN proteins or possible isoforms may have varying effects in different tissues as regards their interaction with TRAF proteins and their influence thereby on the activity of the TRAF proteins, or intracellular signaling mediated by the TRAF proteins.

It is also possible that some of the possible IREN isoforms serve other functions. For example, IREN or some IREN analogs, or isoforms may also act as docking sites for molecules that are involved in other, non-cytotoxic effects of, for example, Fas/APO1 and TNF receptors via interaction with TRAF2 or even independently of TRAF2.

Due to the unique ability of Fas/APO1 and TNF receptors to cause cell death, as well as the ability of the TNF receptors to trigger other tissue-damaging activities, aberrations in the function of these receptors could be particularly deleterious to the organism. Indeed, both excessive and deficient functioning of these receptors have been shown to contribute to pathological manifestations of various diseases (Vassalli, 1992; Nagata and Golstein, 1995). Identifying the molecules that participate in the signaling activity of the receptors, and finding ways to modulate the activity of these molecules, could direct new therapeutic approaches. In view of the suspected important role of TRAF proteins, e.g. TRAF2 and hence the TRAF2-IREN interaction in modulation of NF-κB activation, it seems particularly important to design drugs that can modulate the TRAF2-IREN interaction when it is desired to kill cells (by inhibiting NF-κB activation), and conversely, when it is desired to preserve cells (by enhancement of NF-κB activation).

The present invention also concerns proteins or other ligands which can bind to the IREN proteins of the invention and thereby modulate/mediate the activity of the IREN proteins. Such proteins or ligands may be screened, isolated and produced by any of the above mentioned methods. For example, there may be isolated a number of new ligands, including proteins, capable of binding to the IREN proteins of the invention (such new proteins/ligands excluding the known TRAF2 and TRAF1).

As detailed above, such new IREN protein-binding proteins/ligands, e.g. IREN-binding proteins, may serve as, for example, inhibitors or enhancers of IREN-mediated activity or the activity mediated by the, for example, TRAF2-IREN interaction, and as such will have important roles in various pathological and other situations as detailed above. Another function of such IREN protein-binding proteins/ligands would be to serve as specific agents for the purification of the IREN proteins by, for example, affinity chromatography, these new binding proteins/ligands being attached to the suitable chromatography matrices to form the solid or affinity support/matrix through which a solution, extract or the like, containing e.g. IREN, will be passed and in this way to facilitate the purification thereof. Such methods of affinity chromatography are now well known and generally standard procedures of the art.

Likewise, all of the above mentioned IREN proteins, analogs, fragments, isoforms and derivatives of the present invention may be used to purify by affinity chromatography the various TRAF proteins to which they bind. For example IREN, and analogs, fragments and muteins of IREN (see examples below) may be used for the affinity chromatography purification of TRAF2.

The invention will now be described in more detail in the following non-limiting examples and the accompanying drawings:

It should also be noted that the procedures of:

i) two-hybrid screen and two-hybrid β-galactosidase expression test; (ii) induced expression, metabolic labeling and immunoprecipitation of proteins; (iii) in vitro binding; (iv) assessment of the cytotoxicity; and (v) Northern and sequence analyses, as well as other procedures used in the following Examples have been detailed in previous publications by the present inventors in respect of other intracellular signaling proteins and pathways (see, for example, Boldin et al., 1995a, 1995b, and Boldin et al. 1996). These procedures also appear in detail in the co-owned co-pending Israel Application Nos. 114615, 114986, 115319, 116588, 117932, and 120367 as well as the corresponding PCT application No. PCT/US96/10521). Accordingly, the full disclosures of all these publications and patent applications are included herein in their entirety and at least as far as the detailed experimental procedures are concerned.

EXAMPLES

Materials and Methods i) cDNA Libraries a) B-Cell cDNA Library

Oligo dT primed library constructed from human B cells was used (Durfee et al., 1993). The cDNAs of the library were inserted into the XhoI site of the pACT based vector pSE1107 in fusion with GAL4 activation domain.

b) λgt10 Testis cDNA library

A cDNA library from human testis was used. The library is a random hexanucleotide primed library with an average insert size of 200 to 400 bp.

ii) Yeast Strains

Two yeast stains were used as host strains for transformation and screening: HF7c strain that was used in the two hybrid screen and SFY526 strain that was used in the β-galactosidase assays. Both strains carry the auxotrophic markers trp1 and leu2, namely these yeast strains cannot grow in minimal synthetic medium lacking tryptophan and leucine, unless they are transformed by a plasmid carrying the wild-type versions of these genes (TRP1, LEU2). The two yeast strains carry deletion mutations in their GAL4 and GAL80 genes (gal4-542 and gal80-538 mutations, respectively).

SFY526 and HF7c stains carry the lacZ reporter in their genotypes; in SFY526 strain fused to the UAS and the TATA portion of GAL1 promoter, and in HF7c three copies of the GAL4 17-mer consensus sequence and the TATA portion of the CYC1 promoter are fused to lacZ. Both GAL1 UAS and the GAL4 17-mers are responsive to the GAL4 transcriptional activator. In addition, HF7c strain carries the HIS3 reporter fused to the UAS and the TATA portion of GAL1 promoter.

iii) Cloning of Human TRAF2

The human TRAF2 was cloned by PCR from an HL60 cDNA library (for TRAF2 sequence and other details see Rothe et al., 1994; Rothe et al., 1995a; Cheng et al., 1996; Hsu et al., 1996; and Wallach, 1996). The primers used were: a) 30-mer forward primer CAGGATCCTC ATGGCTGCAGCTAGCGTGAC (SEQ ID NO:1) corresponding to the coding sequence of hTRAF2 starting from the codon for the first Methionine (underlined) and including a linker with BamHI site. b) 32-mer reverse primer GGTCGAC TTAGAGCCCTGTCAGGTCCACAATG (SEQ ID NO:2) that includes hTRAF2 gene stop codon (underlined) and a SalI restriction site in its linker. PCR program comprised of an initial denaturation step 2 min. at 94° C. followed by 30 cycles of 1 min. at 94° C., 1 min. at 64° C., 1 min. and 40 sec. at 72° C. The amplified human TRAF2 was then inserted into the BamHI-SalI sites of pGBT9 vector in conjunction with GAL 4 DNA Binding domain.

iv) Two Hybrid Screen of B-Cell Library

The two hybrid screen is a technique (see details in above mentioned publications and patent applications) used in order to identify factors that are associated with a particular molecule that serves as a "bait". In the present invention TRAF2 that was cloned into the vector pGBT9, served as the bait. TRAF2 was co-expressed together with the screened B-cell cDNA library in the yeast strain HF7c. The PCR-cloned TRAF2 was a recombinant fusion with the CAL4 DNA-binding domain and the screened cDNA library was fused to the GAL4 activation domain in the pSE1107 vector. The reporter gene in HF7c was HIS3 fused to the upstream activating sequence (UAS) of the GAL1 promoter which is responsive to GAL4 transcriptional activator. Transformants that contained both pGBT9 and pSE1107 plasmids were selected for growth on plates without tryptophan and leucine. In a second step positive clones which expressed two hybrid proteins that interact with each other, and therefore activated GAL1-HIS3, were picked up from plates devoid of tryptophan, leucine and histidine and contained 50 mM 3-amino-triazol (3AT).

v) β-Galactosidase Assay

Positive clones picked up in the two hybrid screen were subjected to lacZ color development test in SFY526 yeast cells, following Clontech Laboratories' manual (for details see above mentioned publications and patent applications). In brief, transformants were allowed to grow at 30° C. for 2-4 days until reaching about 2 mm in diameter, then were transferred onto Whatman filters. The filters went through a freeze/thaw treatment in order to permeabilize the cells, then soaked in a buffer (16.1 mg/ml $Na_2HPO_4.7H_2O$; 5.5 mg/ml $NaH_2PO_4.H_2O$; 0.75 mg/ml KCl; 0.75 mg/ml $MgSO_4.7H_2O$, pH=7) containing 0.33 mg/ml X-gal and 0.35 mM β-mercaptoethanol. Colonies were monitored for development of blue color which is an indication for induction of β-galactosidase.

vi) Expression of Cloned cDNAs

Two kinds of expression vectors were constructed:

a) A pUHD10-3 based vectors containing the open reading frame (ORF) of IREN in fusion with the Hemaglutinin (HA) epitope.

b) A pUHD10-3 based vector into which FLAG octapeptide sequence was introduced just in front of cloned TPAF2, hereby named FLAG/B6/TRAF2.

The constructs containing an ORF of IREN were transfected into the HtTA1 clone of the HeLa cells (for these cells see Gossen, M. and Bujard, M. (1992)) either alone or cotransfected with FLAG/B6/TRAF2 using standard calcium-phosphate method (Method in, for example, Current Protocols in Molecular Biology, eds. Ausubel, F. M et al.)

vii) Luciferase Assay

Typically $5 \times 10^5$ transfected cells were harvested by washing three times with cold PBS and resuspending in 400 μl extraction buffer (0.1 M $K_2HPO_4/KH_2PO_4$ pH=7.8; 1 mM DTT). Lysis of the cells was achieved by three times freezing in liquid nitrogen and thawing. Cell debris was removed by centrifugation (5 min. at 10,000×g). For the luciferase assay, 200 μl of luciferase buffer (25 mM glycylglycine, 15 mM $K_xHPO_4/KH_2PO_4$ pH=7.8, 15 mM $MgSO_4$, 4 mM EGTA, 2 mM ATP, 1 mM DTT) were added to 50 μl of the lysate. Subsequently, 100 μl of 0.2 mM D-luciferine, 25 mM glycylglycine, 1 mM DTT were added to the reaction. Luciferase activity was determined by readind light emission using a Lumitron luminometer set on 10 seconds integration (see above publications and patent applications for additional details).

Example 1

Cloning of IREN and Two Hybrid Test

A cDNA library prepared from B-cells was screened for proteins that associate with TRAF2, using the two-hybrid technique as described in Materials and Methods (iv). Only in transformants that expressed both TRAF2 and a protein capable of interacting with it, the GAL4 DNA-binding domain and the transcriptional activation domain were brought together. The result was the activation and expression of the reporter gene, in this case HIS3 fused to the UAS and the TATA portion of the GAL1 promoter.

The screen yielded approximately 2000 clones, which were able to grow on Trp-, Leu-, His-3AT plates. DNA prepared from 165 randomly selected positive clones served for transient co-transfection of SFY526 yeast strain together with TRAF2 cloned into pGBT9 vector. Assay for β-galactosidase activity was performed on the transformed SFY526 yeast colonies as described in Materials and Methods (v). The blue color that developed was an indication for yeast colonies that contain cDNA encoding a protein or polypeptide that binds to TRAF2.

6 independent clones were identified that encoded the novel protein IREN by their ability to grow on 3AT plates and to induce LacZ as measured in the color test. Of all the positive clones checked, two were cDNAs coding for known proteins; TRAF2 itself that is capable of self-associating and forming homodimers, and the lymphotoxin beta receptor whose intracellular domains were shown to bind TRAF2.

The positive clones were further analysed in a binding specificity test, namely analysed for their interaction with irrelevant baits. As shown in Table II, IREN reacted only with TRAF2 and TRAF1 and did not bind to any one of a number of irrelevant proteins analysed such as lamin, and Cyclin D. IREN did not bind the intracellular domain of the p55 and p75 TNF receptors, MORT, NIK, $NIK mutant_{1-400}$, nor A20.

In order to narrow down the region on the TRAF2 molecule which interacts with IREN two additional constructs were made. One construct comprising the N-terminal part of the TRAF2 molecule, amino acids 1 to 224 designated $RING_{1-224}$ comprising the Ring finger and the zinc finger motifs. The second construct included only the C-terminal part of TRAF2, amino acids 225 to 501, covering the "TRAF-domain" as well as an additional 42 amino acids. These two constructs were used as baits in two hybrid tests. The results clearly show that IREN did not interact with the construct comprising amino acids 1 to 224 of the TRAF2 molecule, they did however bind to the C-terminal construct comprising the "TRAF domain" with the same efficiency as they bound to the full length TRAF2 (Table II). Deletion analysis demonstrated that the TRAF2 binding region in IREN and its isoforms is confined to the region between amino acids 198 and 388 thereof (Table II).

TABLE II

Yeast 2 hybrid test for IREN interactions

| Bait | Prey | Interaction |
|---|---|---|
| TRAF2 | IREN | +++ |
| $TRAF2_{225-501}$ | IREN | +++ |
| $RING_{1-224}$ | IREN | − |
| TRAF2 | $IREN_{1-197}$ | − |
| Lamin | $IREN_{1-197}$ | − |
| TRAF2 | $IREN_{198-388}$ | +++ |
| Lamin | $IREN_{198-388}$ | − |

TABLE II-continued

Yeast 2 hybrid test for IREN interactions

| Bait | Prey | Interaction |
| --- | --- | --- |
| TRAF2 | IREN$_{398-541}$ | +/− |
| Lamin | IREN$_{398-541}$ | +/− |
| TRAF2 | IREN$_{198-541}$ | +++ |
| Lamin | IREN$_{198-541}$ | − |
| TRAF2 | IREN 10B | ++ |
| IREN 10B | IREN 10B | ++ |
| IREN 10B | IREN | − |
| Lamin | IREN 10B | − |
| Lamin | IREN | − |
| CycD | IREN | − |
| p75IC | IREN | − |
| p55IC | IREN | − |
| MORT | IREN | − |
| TRAF3 | IREN | − |
| NIK | IREN | − |
| NIK 1-400 | IREN | − |
| TRAF1 | IREN | +++ |
| A20 | IREN | − |
| TRAF6 | IREN | − |

The open reading frame of IREN cDNA encodes a protein of 541 amino acid. The cDNA also contains a short 3'UTR as well as poly(A) (FIGS. 3A and 3B).

The 5' domain of IREN open reading frame (ORF) was found to contain a region which is homologous to one other known protein (ID: U73941, cloned in a 2-hybrid screen for Rap2 binding proteins (Janoueix-Lerosey I et al 1998) as well as to additional unknown proteins found in the databases: two human gene (KIAA0871, KIAA0842) and one *C. Elegans* gene (ID CAA21666).

The sequence of IREN was found to contain a peptide sequence [IDSLSL 326-331] which is also present within the 51 amino acid domain spanning amino acids 769 to 820 of NIK which is essential for IKK-1 binding to NIK in a 2-hybrid assay and NF-kB activation by NIK overexpression (data not shown).

Example 2

Further Studies and Functional Characteristics of IREN

IREN cDNA fused to an HA epitope was expressed in the 293 human kidney cell lines using a pcDNA3 based vector containing the ORF of IREN in fusion with the Hemagglutinin (HA) epitope. IREN was then immunoprecipitated with anti HA antibodies. Cells were transfected with the IREN-HA fusion protein using a standard calcium-phosphate method (Method in, for example, Current Protocols in Molecular Biology, eds. Ausubel, F. M et al.). Cells were then grown for 24 hrs. in Dulbecco's Modified Eagle's Medium (DMEM) plus 10% calf serum. At the end of the incubation time, cells were lysed in radioimmune precipitation buffer (10 mM Tris-HCl, pH 7.5, 150 mM NaCl, 1% Nonident P-40, 1% deoxycholate, 0.1% SDS, and 1 mM EDTA; 1 ml/5×10$^5$ cells), and the lysate was precleared by incubation with irrelevant rabbit antiserum and Protein G-Sepharose beads (Pharmacia, Sweden). Immunoprecipitation was performed by I-hour incubation at 4° C. of aliquots of the lysate with anti-HA (clone 12CA5 (Field, J. et al., 1988) monoclonal antibodies. The expressed proteins were analysed on an SDS-PAGE gel followed by Western Blot with anti HA antibodies. The protein encoded by IREN thus appears as a band of approximately 60 kDa.

Studies of IREN effect on NF-κB activation were performed using the reporter gene assay. 293 EBNA cells were co-transfected with the pcDNA3 vector containing HIV LTR linked to the luciferase reporter gene, together with either the pcDNA3 plasmid containing IREN cDNA alone, or with a pcDNA3 plasmid containing the cDNA encoding the following proteins: IKK-1, full length NEMO, C-terminal deletion of NEMO, NIK, kinase deficient mutant of NIK (NIKmut), a C terminal deletion mutant of IREN (IREN$_{1-197}$) or an N-terminal deletion mutant of IREN (IREN$_{198-541}$).

Transfection was done using a standard calcium-phosphate method (Method in, for example, Current Protocols in Molecular Biology, eds. Ausubel, F. M et al.) as described in the above Material and methods (vii).

In co-transfection with murine IKK-1, a known substrate for NIK enzymatic activity (Regnier C H, et al 1997), human IREN was found to efficiently induce NF-κB in 293 cells as determined by the luciferase assay (see FIG. 10).

Co-transfection of a C-terminal deletion mutant of NEMO (CΔNEMO amino acids 1-309) which is reportedly able to block enzymatic activity of IKKs (Rothwarf D M, et al. 1998], was found to inhibit NF-κB induced by IREN and IKK1 co-transfection (FIG. 10).

The activity of NF-κB induced by IREN and IKK1 co-transfection was comparable to that induced by co-expression of full size NEMO and IKK1. NEMO was not able to further potentiate NF-κB induced by IREN and IKK1 (FIG. 10).

Unlike CΔNEMO, cotransfection of a kinase-deficient mutant of NIK (NIKmut, amino acids (see co-pending co-owned Patent Application WO 97/37016, Malinin et al. 1996) was not able to block NF-kB induction by cotransfection of IREN and IKK1 (FIG. 10).

IREN co-expressed at a 2:1 fold ratio with NIK DNA effectively potentiates induction of NF-κB. Co-expression of full-size NEMO with NIK blocks NF-κB induced by the latter. This inhibition could be reversed by expression of IREN (FIG. 10). As it was shown earlier (see co-pending co-owned Patent Application WO 97/37016, Malinin et al. 1996) NIKmut effectively blocks NF-κB induced by CD120a overexpression. This effect was not altered by co-expression of IREN (FIG. 10).

Taken together the abovementioned data lead to the suggestion that IREN acts within the NF-κB signalling pathway, acting downstream to NIK but upstream to NEMO and IKK1 and could be a modulator of the interaction between NIK and IKK-1.

It was therefore hypothesized that some deletion mutant of IREN might interfere with the signal flow from NIK kinase to the NEMO-IKK complex. The C terminal deletion mutant IREN$_{1-197}$ did not have any effect on NIK-induced NF-kB activation (data not shown). However an N-terminal deletion mutant of IREN (IRENΔN; IREN$_{198-541}$) profoundly inhibited NIK-induced NF-κB, to the extent comparable to that of NEMO (FIG. 10).

Example 3

Kinase Assay

293-T cells (2×10$^6$) were transfected with pcFLAG CHUK (encoding murine IKK1) alone or in combination with pcNIK, pc20.4 (encoding the NEMO protein) or pcHIS-IREN (encoding His tagged-IREN), or pcHIS-IRENΔN (pcHIS-IREN$_{198-541}$ encoding a His tagged N terminal deletion mutant of IREN that acts as a dominant negative). 24 h post transfection cells were harvested, lysed in lysis buffer containing 1% NP-40, 50 mM Hepes pH-7.5, 100 mM NaCl, 10% glycerol, 1 mM EDTA, 20 mM b-glycerophosphate, 20 mM PNPP, 1 mM Na3VaO4, 1 mM NaF, 1 mM Na-Metabisulfite, 1 mM Bezamidine, 1 mM DTT, "Complete" protease inhibitors (Boehringer).

Cell debris was then removed by centrifugation. Following addition of NaCl to up to 250 mM, proteins were immunoprecipitated with monoclonal anti FLAG antibodies, washed thoroughly in washing buffer containing lysis buffer with 0.1% NP-40 and 250 mM NaCl, and eluted with 30 µl wash buffer containing 1 mg/ml FLAG peptide. Aliquots of the eluates were used for an in-vitro kinase reactions with *E. coli* produced GST-IκB as substrate, in the presence of $^{32}$P-gamma ATP in kinase buffer containing 50 mM β-glycerophosphate, 2 mM DTT, 20 mM MgCl$_2$, 1 mM Na$_3$VaO$_4$, 1 mM EDTA/EGTA. The reactions were separated by SDS-PAGE and phosphorylation of proteins was detected after exposure to X-Ray film. As control, amount of protein in the lysate was determined by western blot with anti FLAG antibody.

The N terminal deletion mutant of IREN was found to act as a dominant negative molecule and to block IKK-1 activity in the kinase assay when IREN and IKK-1 were coexpressed with NEMO.

Figure 11:
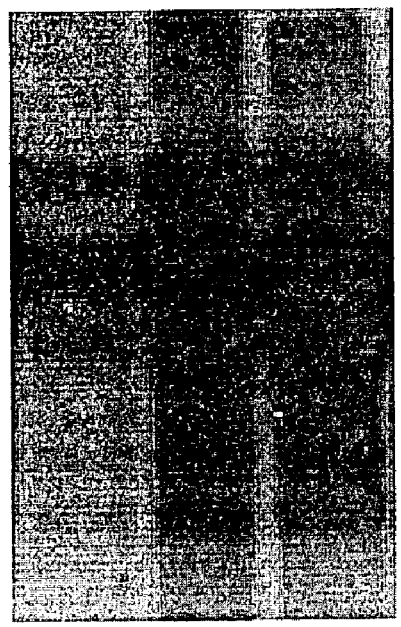
FIG. 11: shows an autoradiogram of FLAG-IKK1, GST-IkappaB and NEMO, obtained after transfection of 293 cells with pcFLAG CHUK (encoding murine IKK1) and pc20.4 (encoding the NEMO protein), together with pcHIS-IRENΔN (pcHIS-IREN$_{198-541}$, left lane), pcHIS-IREN (middle lane), or the empty pcDNA3 vector (right lane) as control. Immunoprecipitation and kinase assays were carried out as described in Example 3. The sizes of the visible bands correspond to the molecular weights determined for FLAG-IKK1, GST-IkappaB and NEMO.

Overexpression of IKK1 and NEMO, but not of IKK1 alone, induces robust kinase activity of IKK1 (as assessed by autophosphorylation and by phosphorylation of *E. coli* produced GST-IkappaB fusion protein). Coexpression of IREN$_{198-541}$ with IKK1 and NEMO results in a significant decrease in activity (FIG. 11) without affecting the IKK1 and NEMO expression level. Full size IREN did not have such an effect (FIG. 11, middle lane).

Example 4

Cloning and Sequencing of IREN-10B and IREN-E

In order to identify splice variants of IREN, a phage cDNA library derived from the abovementioned MCF7 cell line was screened with the first 600 bp of IREN as probe. Two independent clones were identified which appeared to be two different variants of IREN. These two clones are identical to IREN in their first 5' 1595 bp and have additional coding sequences at the 3-prime end. This region contains a PX domain—a conservative domain of unknown function (presumably a protein-protein interaction domain) that is also found in some signalling molecules, including PI3-kinase. In clone 10B and clone E the PX domain is flanked by two short identical regions. The region downstream to these regions is different in the two clones. For a comparison of the two splice variants to IREN see FIG. 9.

Provisional sequencing of the 5-prime UTR (from the beginning of the sequence up to the first ATG with Kozak sequence) indicated these sequences were identical in IREN and in IREN-10B and IREN-E isoforms.

Figure 9:
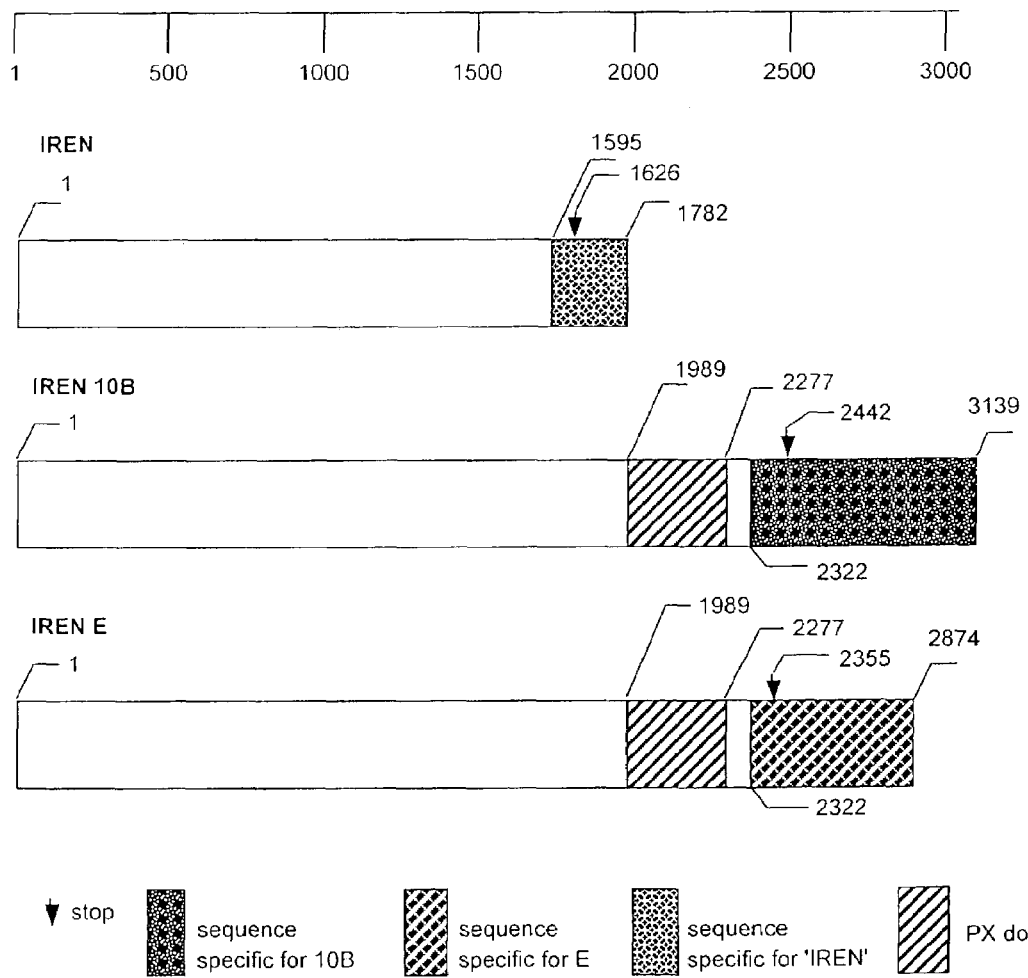
FIG. 9: shows a comparison between the sequence of IREN and its isoforms IREN-10B and IREN-E.

The region of TRAF2 binding is mapped to IREN$_{198-388}$, which is identical in all three splice isoforms shown (FIG. 9). Accordingly, IREN 10B also interacted with TRAF2 in the two-hybrid assay. Although no self-association of IREN was observed, IREN 10B did self-associate in the two-hybrid test, whereas, it did not interact with IREN (Table II).

A deletion mutant of IREN 10B lacking the PX domain, but including a coiled coil motiv not present in IREN, was also able to self associate. This indicates that this coiled coil domain is responsible for self interaction of IREN 10B.

Example 5

Proteins Interacting with IREN 10B and IREN

A B cell library was screened with IREN 10B using the yeast two hybrid system as described above to identify additional proteins interacting with IREN 10B. Three such proteins were identified that interacted strongly and specifically with IREN 10B:

1) The mu 1 subunit of the clathrin assembly protein 2 (AP50, CLAPM1; gene bank accession numbers U36188), which interacted strongly with IREN 10B, but only weakly with IREN.

2) The FBI or Amida gene, which interacted strongly and specifically both with IREN 10B as well as with IREN. This gene was initially identified as a sequence fused to the E2A gene in childhood pre-B leukemia cells (Brambillasca et al, Leukemia 13 (3), 369-375, 1999). It was recently shown to induce apoptosis upon overexpression. It is localized in the nucleus and is involved in nuclear translocation of a neuron specific immediate early gene called Arc (Irie et al, J. Biol. Chem 275, (2000) 2647-2653).

3) The TRAX gene, which interacted strongly with IREN 10B, but only very weakly with IREN. This gene is highly homologous to the DNA binding protein Translin and may be involved in nuclear localisation of Translin (Aoki et al, FEBS Lett 401, 109-112, 1997).

In view of the fact that IREN 10B interacts strongly and specifically with the above proteins, IREN may thus also be active in controlling trafficking of signal proteins, e.g. TRAF-2.

Example 6

Figure 12:
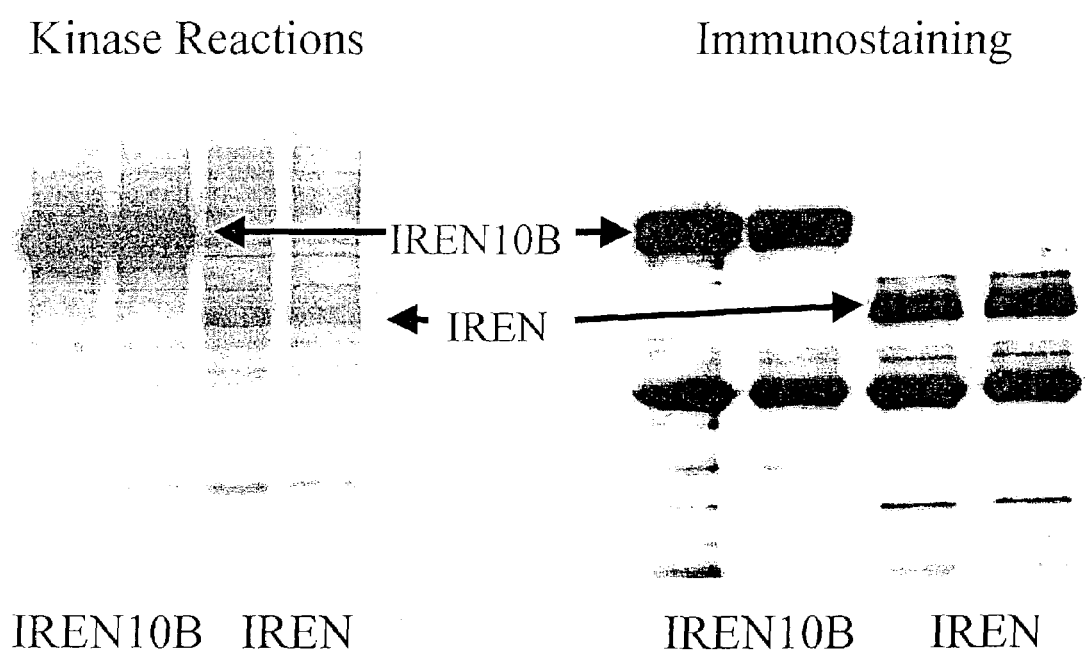
FIG. 12: shows an autoradiogram (left) and immunostaining (right) of SDS-PAGE analysis of IREN 10B and IREN that were immunoprecipitated from transfected cells and then subjected to an in vitro kinase test. The figure demonstrates that IREN 10B associates in cells with a protein kinase that can phosphorylate this IREN splice variant.

IREN 10B Strongly Interacts with an Unidentified Kinase that Phosphorylates IREN 10B IREN 10B as well as IREN, fused to N-terminal 6-His tag were expressed in 293T cells by transient transfection. The proteins were purified 24 hours after transfection by immunoprecipitation. The immunoprecipitates were subject to PAGE and immunostaining with anti-His antibodies showing that both proteins were expressed to a similar extent. Kinase reactions were performed with both immunoprecipitates. The IREN 10B protein underwent strong phosphorylation showing that this protein was associated with an unidentified kinase whose substrate is IREN 10B. IREN itself was only weakly phosphorylated, possibly by unspecifically bound kinases. This indicates that the above kinase interacts with the C-terminal sequences of IREN 10B, possibly its PX domain (FIG. 12).

Example 7

IREN Seems to be a Member of a Gene Family

BLAST search of the newly available genebank containing most of the nearly completed human genome sequence revealed that at least partial copies of the IREN gene as well as a very closely related isoform with 97-98% identity at the nucleotide level occur in several locations on 5 chromosomes, with conserved exon structure. Exons 4-7 of either of the two isoforms, encoding amino acids 113-406 (corresponds to nucleotides 559-759 of the sequences in FIGS. 3B, 4, and 5 [SEQ ID NO:4, SEQ ID NO:5, and SEQ ID NO:6, respectively]) and thus the TRAF 2 binding domains, were found conserved on 4 different chromosomes, while additional exons were detected on only one or two of those chromosomes. These data could indicate that IREN variants are expressed in various sizes with different N- and C-terminal extensions as molecules that regulate TRAF1 or TRAF2 dependent signalling pathways (FIG. 13 A).

Examination of the EST databank by BLAST revealed that the at least parts of IREN are expressed in highly conserved form in mouse and beef. ESTs corresponding to both isoforms of the IREN gene, the one described in this patent as well as the one found in other chromosomal locations mentioned above are found in the EST databank, demonstrating that both closely related isoforms are active genes (FIG. 13 B).

REFERENCES

1. Adelman et al., (1983) DNA 2, 183.
2. Alnemri, E. S. et al. (1995) J. Biol. Chem. 270, 4312-4317.
3. Arch R H et al (1998). Genes Dev. September 15; 12(18): 2821-30
4. Arch, R. H. and C. B. Thompson. (1998) B. *Mol. Cell. Biol.* 18, 558-565.
5. Ausubel, F. M. et al. eds., Current Protocols in Molecular Biology.
6. Baeuerle, P. A., and Henkel, T. (1994) Annu Rev Immunol.
7. Bazan, J. F. (1993). Current Biology 3, 603-606.
8. Berberich, I., Shu, G. L., and Clark, E. A. (1994). J Immunol 153, 4357-66.
9. Beutler, B., and van Huffel, C. (1994). Science 264, 667-8.
10. Blank, V., Kourilsky, P., and Israel, A. (1992). Trends Biochem. Sci 17, 135-40.
11. Boldin, M. P. et al. (1995a) J. Biol. Chem. 270, 337-341.
12. Boldin, M. P., Varfolomeev, E. E., Pancer, Z., Mett, I. L., Camonis, J. H., and Wallach, D. (1995b). J. Biol. Chem. 270, 7795-7798.
13. Boldin, M. P. et al. (1996) Cell 85, 803-815.
14. Born T L et al. (1998) J Biol Chem. 273, 29445-50.
15. Cao, Z. et al. (1996a) Nature 383, 443-446.
16. Cao, Z. et al. (1996b) Science 271, 1128-1131.
17. Chen, C. J. et al. (1992) Ann. N.Y. Acad. Sci. 660:271-273.
18. Cheng, G., Cleary, A. M., Ye, Z-s., Hong, D. I., Lederman, S, and Baltimore, D. (1995) Science 267:1494-1498.
19. Cheng, G. and Baltimore, D. (1996) Genes Dev. 10, 963-973.
20. Chinnalyan, A. M., O'Rourke, K., Tewari, M., and Dixit, V. M. (1995) Cell 81, 505-512.
21. Creighton, T. E., Proteins: Structure and Molecular Properties, W.H. Freeman & Co., San Francisco, Calif. 1983.
22. Croston, G. E., Cao, Z., and Goeddel, D. V. (1995). J Biol Chem 270, 16514-7.
23. DiDonato, J. A., Mercurio, F., and Karin, M. (1995). Mol Cell Biol 15, 1302-11.
24. Duckett, C. S., R. W. Gedrich, M. C. Gilfillan, and C. B. Thompson. (1997) *Mol. Cell. Biol.* 17, 1535-1542
25. Durfee, T. et al. (1993) Genes Dev. 7:555-569.
26. Field, J. et al. (1988) Mol. Cell Biol. 8:2159-2165.
27. Geysen, H. M. (1985) Immunol. Today 6, 364-369.
28. Geysen, H. M. et al. (1987) J. Immunol. Meth. 102, 259-274.
29. Gilmore, T. D., and Morin, P. J. (1993). Trends Genet 9, 427-33.
30. Gossen, M. and Bujard, M. (1992) PNAS 89:5547-5551.
31. Grell, M., Douni, E., Wajant, H., Lohden, M., Clauss, M., Baxeiner, B., Georgopoulos, S., Lesslauer, W., Kollias, G., Pfizenmaier, K., and Scheurich, P. (1995). Cell 83, 793-802.
32. Grilli, M., Chiu, J. J., and Lenardo, M. J. (1993). Int RevCytol.
33. Hanks, S. K., Quinn, A. M., and Hunter, T. (1988). Science 241, 42-52.
34. Hibi, M., Lin, A. Smeal, T. Minden, A. and Karin M. (1993) Genes & Dev. 7, 2135-2148
35. Howard, A. D. et al. (1991) J. Immunol. 147, 2964-2969.
36. Hsu, H., Shu, H.-B., Pan, M.-G., and Goeddel, D. V. (1996). Cell 84, 299-308.
37. Hsu, H., Xiong, J., and Goeddel, D. V. (1995). Cell 81, 495-504.
38. Ishida T et al. (1996a) Proc Natl Acad Sci USA. 93, 9437-42.
39. Ishida T et al. (1996b) J Biol Chem. 271, 28745-8.
40. Janoueix-Lerosey I et al Eur J Biochem (1998) March 1; 252(2):290-8
41. Kanakaraj P et al (1999) J Exp Med 189, 1129-38
42. Kaufmann, S. H. (1989) Cancer Res. 49, 5870-5878.
43. Kaufmann, S. H. (1993) Cancer Res. 53, 3976-3985.
44. Lalmanach-Girard, A. C., Chiles, T. C., Parker, D. C., and Rothstein, T. L. (1993). J Exp Med 177, 1215-1219.
45. Lazebnik, Y. A. et al. (1994) Nature 371, 346-347
46. Lee, S. Y., C. G. Park, and Y. Choi. 1996 J. Exp. Med. 183, 669-674.
47. Lee, S. Y., A. Reichlin, A. Santana, K. A. Sokol, M. C. Nussenzweig, and Y. Choi. (1997) Immunity 7, 703-713.
48. Li Y et al (1998) Mol Cell Biol. 18, 1601-10.
49. Lin, A., A. Minden, H. Martinetto, F. X. Claret, C. Lange-Carter, F. Mercurio, G. L. Johnson, and M. Karin. (1995) Science 268, 286-290.
50. Liu, Z.-G., Hsu, H. Goeddel D. V., and Karin M. 1996. *Cell* 87, 565-576
51. Mashima, T. et al. (1995) Biochem. Biophys. Res. Commun. 209, 907-915.
52. McDonald, P. P., Cassatella, M. A., Bald, A., Maggi, E., Romagnani, S., Gruss, H. J., and Pizzolo, G. (1995). Eur J Immunol 25, 2870-6.
53. Mercurio F and Manning A M (1999a) Curr Opin Cell Biol. 1999 11, 226-32
54. Mercurio F et al (1999b) Mol Cell Biol. 19, 1526-38.
55. Messing et al., Third Cleveland Symposium on Macromolecules and Recombinant DNA, Ed. A. Walton, Elsevier, Amsterdam (1981)
56. Minden, A., Lin A., McMahon M., Lange-Carter C., Derijard B., Davis R. J., Johnson, G. L. and. Karin M. 1994. *Science* 266, 1719-1723.
57. Milligan, C. E. et al. (1995) Neuron 15, 385-393.
58. Mosialos, G., Birkenbach, M., Yalamanchili, R., VanArsdale, T., Ware, C., and Kieff, E. (1995). Cell 80, 389-399.
59. Muranishi, S. et al. (1991) Pharm. Research 8, 649.
60. Nagata, S, and Golstein, P. (1995) Science 267, 1449-1456.
61. Nakano H (1996) J Biol Chem. 271, 14661-4.
62. Park, Y. C. (1999) Nature. 398, 533-8
63. Reinhard C., Shamoon, B. Shyamala, V. and Williams. L. T. 1997. *EMBO J.* 16, 1080-1092
64. Regnier C H (1995) J. Biol. Chem. 270, 25715-21.
65. Regnier C H, Song H Y, Gao X, Goeddel D V, Cao Z, Rothe M (1997) Cell 90, 373-383
66. Rensing-Ehl, A., Hess, S., Ziegler-Heitbrock, H. W. L., Riethmüller, G., and Engelmann, H. (1995). J. Inlamm. 45, 161-174.
67. Rothe, M., Pan, M-G, Henzel, W. J., Ayres, T. M., and Goeddel, D. V. (1995b). Cell 83, 1243-1252.
68. Rothe, M., Sarma, V., Dixit, V. M., and Goeddel, D. V. (1995a). Science 269, 1424-1427.

69. Rothe, M., Wong, S. C., Henzel, W. J., and Goeddel, D. V. (1994). Cell 78, 681-692.
70. Rothe, M. et al. (1996) Proc. Natl. Acad. Sci. U.S.A. 93, 8241-8246.
71. Rothwarf D M et al (1998) Nature. 395, 297-300.
72. Roy, N., Q. L. Deveraux, R. Takahashi, G. S. Salvesen, and J. C. Reed. (1997). EMBO J. 16, 6914-6925.
73. Ruzicka et al., (1993) Science 260, 487.
74. Sambrook et al. (1989) Molecular cloning: a laboratory manual, Cold Spring Harbor Laboratory Press, Cold Spring Harbor, N.Y.
75. Sano et al., (1992) Science 258, 120.
76. Sano et al., (1991) Biotechniques 9, 1378.
77. Schreiber, E., Matthias, P., Muller, M. M. and Schaffner, W. (1989), Nuc. Acids Res. 17:6419.
78. Schulz et al., G. E., Principles of Protein Structure, Springer-Verlag, New York, N.Y. 1798.
79. Sleath, P. R. et al. (1990) J. Biol. Chem. 265, 14526-14528.
80. Shi, C.-S, and J. H. Kehrl. (1997) *J. Biol. Chem.* 272, 32102-32107.
81. Smith, C. A., Farrah, T., and Goodwin, R. G. (1994). Cell 76, 959-962.
82. Song, H. Y., C. H. Regnier, C. J. Kirschning, D. V. Goeddel, and M. Rothe. (1997). Proc. Natl. Acad. Sci. 9, 9792-9796
83. Stanger, B. Z. et al. (1995) Cell 81, 513-523.
84. Su, B., E. Jacinto, M. Hibi, T. Kallunki, M. Karin, and Y. Ben-Neriah. (1994) *Cell* 77, 727-736
85. Thornberry, N. A. et al. (1992) Nature 356, 768-774.
86. Thornberry, N. A. et al. (1994) Biochemistry 33, 3934-3940.
87. Vandenabeele, P., Declercq, W., Beyaert, R., and Fiers, W. (1995). Trends Cell Boil. 5, 392-400.
88. Varfolomeev, E. E., Boldin, M. P., Goncharov, T. M., and Wallach, D. (1996). J. Exp. Med. 183, 1271-5.
89. Vassalli, P. (1992) Ann. Rev. Immunol. 10, 411-452.
90. Veira et al., (1987) Meth. Enzymol. 153, 3.
91. Wallach, D. (1996) Eur. Cytokine Net. 7, 713-724.
92. Wang, L. et al. (1994) Cell 78, 739-750.
93. Wilks, A. F. et al. (1989) Proc. Natl. Acad. Sci. USA, 86:1603-1607.
94. Yamaoka S et al. (1998) Cell. 93, 1231-40.
95. Yeh, W.-C., A. Shahinian, D. Speiser, J. Kraunus, F. Billia, A. Wakeham, J. L. de la Pompa, D. Ferrick, B. Hum, N. Iscove, P. Ohashi, M. Rothe, D. V. Goeddel, and T. W. Mak. (1997) *Immunity* 7, 715-725
96. Zaccharia, S. et al. (1991) Eur. J. Pharmacol. 203, 353-357.
97. Zhao, J. J. and Pick, L. (1993) Nature 365:448-451.

The invention claimed is:

1. An isolated DNA sequence encoding a protein capable of binding to TRAF, consisting of the nucleotide sequence of SEQ ID NO:4.

2. A vector comprising a DNA sequence encoding a protein encoded by SEQ ID NO:4.

3. A vector according to claim 2 capable of being expressed in a eukaryotic host cell.

4. A vector according to claim 2 capable of being expressed in a prokaryotic host cell.

5. Isolated transformed eukaryotic or prokaryotic host cells containing a vector according to claim 2.

* * * * *